United States Patent
Belanoff

(10) Patent No.: US 12,097,210 B2
(45) Date of Patent: *Sep. 24, 2024

(54) CONCOMITANT ADMINISTRATION OF GLUCOCORTICOID RECEPTOR MODULATORS AND CYP3A INHIBITORS

(71) Applicant: Corcept Therapeutics, Inc., Menlo Park, CA (US)

(72) Inventor: Joseph K. Belanoff, Menlo Park, CA (US)

(73) Assignee: Corcept Therapeutics, Inc., Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/241,364

(22) Filed: Sep. 1, 2023

(65) Prior Publication Data

US 2023/0414635 A1    Dec. 28, 2023

Related U.S. Application Data

(63) Continuation of application No. 17/544,859, filed on Dec. 7, 2021, now Pat. No. 11,969,435, which is a continuation of application No. 16/482,656, filed as application No. PCT/US2018/020336 on Feb. 28, 2018, now abandoned.

(60) Provisional application No. 62/466,867, filed on Mar. 3, 2017, provisional application No. 62/465,772, filed on Mar. 1, 2017.

(51) Int. Cl.
| | | |
|---|---|---|
| A61K 31/575 | (2006.01) | |
| A61K 9/00 | (2006.01) | |
| A61K 31/496 | (2006.01) | |
| A61K 31/7048 | (2006.01) | |
| A61K 45/06 | (2006.01) | |
| A61P 3/10 | (2006.01) | |

(52) U.S. Cl.
CPC .......... *A61K 31/575* (2013.01); *A61K 9/0056* (2013.01); *A61K 31/496* (2013.01); *A61K 31/7048* (2013.01); *A61K 45/06* (2013.01); *A61P 3/10* (2018.01)

(58) Field of Classification Search
CPC ................ A61K 31/575; A61K 31/496; A61K 31/7048; A61P 3/10
See application file for complete search history.

(56) References Cited

U.S. PATENT DOCUMENTS

| | | |
|---|---|---|
| 8,598,149 B2 | 12/2013 | Belanoff |
| 8,921,348 B2 | 12/2014 | Belanoff |
| 9,216,221 B2 | 12/2015 | Newell-Price |
| 9,943,526 B2 | 4/2018 | Belanoff et al. |
| 10,195,214 B2 | 2/2019 | Belanoff |
| 10,842,800 B2 | 11/2020 | Belanoff |
| 2004/0029848 A1 | 2/2004 | Belanoff |
| 2007/0254025 A1 | 11/2007 | Cronk |
| 2010/0135956 A1 | 6/2010 | Gant et al. |
| 2010/0261693 A1 | 10/2010 | Ulmann et al. |
| 2016/0067264 A1 | 3/2016 | Newell-Price |
| 2017/0281651 A1 | 10/2017 | Belanoff |
| 2017/0326157 A1 | 11/2017 | Belanoff |

FOREIGN PATENT DOCUMENTS

| | | |
|---|---|---|
| EP | 1886695 A1 | 2/2008 |
| JP | 2011515444 A | 5/2011 |
| JP | 2013509394 A | 3/2013 |
| TW | 201629098 A | 8/2016 |
| WO | 0180896 A2 | 11/2001 |
| WO | 2008060391 A2 | 5/2008 |
| WO | 2009050136 A2 | 4/2009 |
| WO | 2010052445 A1 | 5/2010 |
| WO | 2010138758 A1 | 12/2010 |
| WO | 2016187347 A1 | 11/2016 |

OTHER PUBLICATIONS

"A Guide to Drug Safety Terms at FDA", FDA Consumer Health Information, U.S. Food and Drug Administration, Available Online at: www.tinyurl.com/y60ao2sj, Nov. 2012, pp. 1-3.
"A Study of the Efficacy and Safety of CORLUX in the Treatment of Endogenous Cushing's Syndrome (SEISMIC)", U.S. National Library of Medicine, Accessed from Internet at Dec. 13, 2018, pp. 1-10.
"An Extension Study of CORLUX in the Treatment of Endogenous Cushing's Syndrome", Archive History for NCT00936741, U.S. National Library of Medicine, Jul. 9, 2009, pp. 1-7.
"Approval Letter", Center For Drug Evaluation and Research, Application No. 202107orig1s000, Available Online at: http://www.accessdata.fda.gov/drugsatfda_docs/nda/2012/202107Orig1s000Approv.pdf, Feb. 17, 2017, pp. 1-7.
"BIAXIN (Clarithromycin)", May 2016, pp. 1-52.

(Continued)

*Primary Examiner* — Sahar Javanmard
(74) *Attorney, Agent, or Firm* — Kilpatrick Townsend & Stockton LLP

(57) ABSTRACT

Applicant provides methods of treating diseases including Cushing's syndrome and hormone-sensitive cancers by concomitant administration of a glucocorticoid receptor modulator (GRM) and steroidogenesis inhibitors, and by concomitant administration of a GRM and CYP3A inhibitors. The GRM may be, e.g., mifepristone; the CYP3A inhibitors or steroidogenesis inhibitors (collectively "inhibitors") may be, e.g., ketoconazole or itraconazole. Inhibitors may cause toxicity or other serious adverse reactions; concomitant administration of inhibitors with other drugs may increase the risk of such toxicity and adverse reactions due to the inhibitors and/or the other drugs. Applicant has surprisingly found that GRMs may be administered to subjects receiving inhibitors without increasing the risk of adverse reactions; for example, Applicant has found that mifepristone may be concomitantly administered with ketoconazole or itraconazole, providing safe concomitant administration of the GRM and ketoconazole or itraconazole. In embodiments, the GRM dose may be reduced during concomitant administration of the GRM with inhibitors.

20 Claims, 2 Drawing Sheets

(56) References Cited

OTHER PUBLICATIONS

"Case PGR2019-00048", Arguments Made by Petitioner in PGR2019-00048 and in the District Court Litigation, *Teva Pharmaceuticals USA, Inc. v. Corcept Therapeutics, Inc.*, U.S. Pat. No. 10,195,214, 2002, 2 pages.
"Case PGR2019-00048", Patent 10, 195,214 B2, File History -- Part 2, *Teva Pharmaceuticals USA, Inc. v. Concept Therapeutics, Inc.*, Document No. 50, Exhibit/Paper No. 1035, Mar. 7, 2019, 427 pages.
"Case PGR2019-00048", Petitioner's Reply in Support of Petition for Post-Grant Review, *Teva Pharmaceuticals USA, Inc. v. Corcept Therapeutics, Inc.*, U.S. Pat. No. 10,195,214, Sep. 23, 2019, 6 pages.
"Case PGR2019-00048", Patent Owner's Authorized Sur-Reply in Further Support of Its Preliminary Response, *Teva Pharmaceuticals USA, Inc. v. Corcept Therapeutics, Inc.*, U.S. Pat. No. 10,195,214, Oct. 3, 2019, 7 pages.
"Case PGR2019-00048", Patent Owner's Exhibit List, *Teva Pharmaceuticals USA, Inc. v. Corcept Therapeutics, Inc.*, U.S. Pat. No. 10,195,214, Oct. 3, 2019, 7 pages.
"Case PGR2019-00048", Patent Owner Preliminary Response, *Teva Pharmaceuticals USA, Inc. v. Corcept Therapeutics, Inc*, U.S. Pat. No. 10,195,214, Aug. 23, 2019, 86 pages.
"Case PGR2019-00048", Petitioner's Exhibit List, *Teva Pharmaceuticals USA, Inc. v. Corcept Therapeutics, Inc.*, U.S. Pat. No. 10,195,214, Sep. 23, 2019, 9 pages.
"Case PGR2019-00048", Opinion, *Teva Pharmaceuticals USA, Inc. v. Corcept Therapeutics, Inc.*, Corcept Ex. 2004, Oct. 23, 2018, pp. 1-7.
"Certification and Request for Prioritized Examination Under 37 CFR 1.102(e)", Doc Code: TRACK1.REQ, Document Description: TrackOne RequestTEVA1035, pt. 1, Jun. 19, 2017, 428 pages.
"Clinical Drug Interaction Studies—Study Design, Data Analysis, and Clinical Implications Guidance for Industry", U.S. Department of Health and Human Services Food and Drug Administration Center for Drug Evaluation and Research, Oct. 2017, 32 pages.
"Clinical Pharmacology and Biopharmaceutics Review(S)", Center For Drug Evaluation and Research, Application No. 202107Orig1s000, Available Online at: http://www.accessdata.fda.gov/drugsatfda_docs/nda/2012/2021070rig1 s000ClinPharmR.pdf, Feb. 18, 2017, pp. 1-120.
"Concomitant Administration of Glucocorticoid Receptor Modulators and CYP3A Inhibitors", Petition for Post-Grant Review Under 35 U.S.C. §§ 321-328 and 37 C.F.R. § 42.200 et seq., Case No. PGR2019-00048, U.S. Pat. No. 10,195,214, May 7, 2019, 78 pages.
"Corcept Therapeutics Incorporated Announces FDA Approval of Korlym(™) (Mifepristone): First and Only Approved Medication for Cushing's Syndrome Patients", Corcept Therapeutics Press Release, Available Online at: https://www.sec.gov/Archives/edgar/data/1088856/000119312512347804/d357533d10q.htm, Accessed from Internet on Apr. 25, 2019, 5 pages.
"CRIXIVAN (Indinavir Sulfate)", Merck & Co., Inc., Sep. 2016, pp. 1-29.
"Cross Discipline Team Leader Review", Center for Drug Evaluation and Research, Application No. 202107Orig1s000, *Teva Pharmaceuticals USA, Inc. v. Corcept Therapeutics, Inc.*, PGR2019-00048, Corcept Ex. 2055, Feb. 13, 2012, pp. 1-32.
"Decision", Case PGR2019-00048, Nov. 20, 2019, pp. 1-37.
"Declaration of Dr. Adrian Dobs, M.D.", Case PGR2019-00048, including Exhibits A (Curriculum Vitae) and B, U.S. Pat. No. 10,195,214 B2, *Teva Pharmaceuticals USA, Inc. v. Concept Therapeutics, Inc.*, Document No. 169, Exhibit/Paper No. 1068, Jun. 4, 2020, 52 pages.
"Declaration of F. Peter Guengerich, Ph.D.", Case PGR2019-00048, *Teva Pharmaceuticals USA, Inc. v. Corcept Therapeutics, Inc.*, Corcept Ex. 2056, 2019, 232 pages.
"Declaration of J.C. Rozendaal in Support of Petitioner's Motion for Pro Hac Vice Admission", Case PGR2019-00048, Sep. 11, 2019, 6 pages.

"Declaration of Laurence Katznelson, M.D.", Case PGR2019-00048, *Teva Pharmaceuticals USA, Inc. v. Corcept Therapeutics, Inc.*, Corcept Ex. 2058, 2019, 83 pages.
"Declaration of Nicholas A. Locastro", Case PGR2019-00048, *Teva Pharmaceuticals USA, Inc. v. Corcept Therapeutics, Inc.*, Corcept Ex. 2048, Dec. 17, 2019, pp. 1-3.
"Declaration of Ty Carroll, M.D.", Case PGR2019-00048, *Teva Pharmaceuticals USA, Inc. v. Corcept Therapeutics, Inc.*, Corcept Ex. 2057, 2019, 59 pages.
"Declaration of Uma N. Everett in Support of Petitioner's Motion for Pro Hac Vice Admission", Case PGR2019-00048, Sep. 11, 2019, 5 pages.
"Declaration of William H. Milliken in Support of Petitioner's Motion for Pro Hac Vice Admission", Case PGR2019-00048, Teva1062, Sep. 11, 2019, 6 pages.
"Defendant Teva Pharmaceuticals USA, Inc.'s Preliminary Invalidity Contentions", *Corcept Therapeutics, Inc.*, Plaintiff, v. *Teva Pharmaceuticals USA, Inc.*, Civil Action No. 2:18-cv-03632 (SDW)(CLW) (Consolidated), May 13, 2019, 138 pages.
"Deposition of Adrian Dobs, M.D.", Case PGR2019-00048, U.S. Pat. No. 10,195,214 B2, *Teva Pharmaceuticals USA, Inc. v. Concept Therapeutics, Inc.*, Document No. 186, Exhibit/Paper No. 2071, Jun. 24, 2020, 193 pages.
"Drug Development and Drug Interactions: Table of Substrates, Inhibitors and Inducers", FDA website (cached), Available Online at: https://www.fda.gov/Drugs/DevelopmentApprovaiProcess/DevelopmentResources/DrugInteractionslabeling/ucm093664.html, Dec. 8, 2017, pp. 1-16.
"Drugs@FDA: FDA Approved Drug Products", Available Online at: https://www.accessdata.fda.gov/scripts/cder/daf/, Accessed from Internet at May 6, 2019, pp. 1-3.
"European Medicines Agency Recommends Suspension of Marketing Authorisations for Oral Ketoconazole", European Medicines Agency, Jul. 26, 2013, pp. 1-3.
"Excerpts of Physician's Desk Reference", 58th Edition, 2004, pp. 1-3.
"FDA Advises Against Using Oral Ketoconazole in Drug Interaction Studies Due to Serious Potential Side Effects", Drugs, Home Drugs, Drug Safety and Availability, Available Online at: http://www.fda.gov/Drugs/DrugSafety/ucm371017.htm, Accessed from Internet on Feb. 11, 2020, pp. 1-2.
"FDA Guidance Documents", Regulatory Information, Available Online at: https://www.fda.gov/regulatoryinformation/guidances/, Accessed from Internet at May 6, 2019, pp. 1-3.
"FDA Label for KORLYM®", Available Online at: https://www.accessdata.fda.gov/drugsatfda_docs/label/2012/202107s000lbl.pdf, Oct. 25, 2016, 23 pages.
"File History for U.S. Pat. No. 9,943,526", Optimizing Mifepristone Levels for Cushing's Patients, Apr. 17, 2018, 257 pages.
"Final Written Decision", Case PGR2019-00048, U.S. Pat. No. 10,195,214 B2, *Teva Pharmaceuticals USA, Inc. v. Concept Therapeutics, Inc.*, Paper No. 51, Nov. 18, 2020, 54 pages.
"Food and Drug Administration Approval Letter for Korlym (Mifepristone) Tablets", NDA 20217, Feb. 17, 2012, pp. 1-6.
"Food-Effect Bioavailability and Fed Bioequivalence Studies", FDA Guidance for Industry, U.S. Department of Health and Human Services Food and Drug Administration Center for Drug Evaluation and Research (CDER), Dec. 2002, pp. 1-12.
"Form 10-Q", Available Online at: https://www.sec.gov/Archives/edgar/data/1088856/000110262412000138/corcept-therapeuticsincorpora.htm, Jun. 30, 2012, pp. 1-76.
"Form 8-K Current Report", Corcept Therapeutics Incorporated, Available Online at: https://www.sec.gov/Archives/edgar/data/1088856/000110262412000138/corcepttherapeutics8k.htm, Feb. 17, 2012, pp. 1-2.
"Full Prescribing Information for KorlymTM(Mifepristone) 300 Mg Tablets", Available Online at: https://www.accessdata.fda.gov/drugsatfda_docs/label/2012/202107s000lbl.pdf., Feb. 29, 2012, 23 pages.
"Guidance for Industry—Drug Interaction Studies—Study Design, Data Analysis, and Implications for Dosing and Labeling", Draft Guidance, Clinical Pharmacology, TEVA1052, Sep. 2006, 55 pages.

(56) References Cited

OTHER PUBLICATIONS

"Guidance for Industry—Drug Interaction Studies—Study Design, Data Analysis, and Implications for Dosing and Labeling", Draft Guidance, Clinical Pharmacology, TEVA1041, Sep. 2006, pp. 1-55.
"Hyperglycemia in Diabetes", The Mayo Clinic, Available Online at: https://www.mayoclinic.org/diseasesconditions/hyperglycemia/symptoms-causes/syc-20373631, Nov. 3, 2018, 6 pages.
"INCIVEK (Telaprevir)", *Teva Pharmaceuticals USA, Inc. v. Corcept Therapeutics, Inc.*, Oct. 2013, pp. 1-28.
"INVIRASE (Saquinavir Mesylate)", *Teva Pharmaceuticals USA, Inc. v. Corcept Therapeutics, Inc.*, Sep. 2016, pp. 1-31.
"KALETRA (Lopinavir and Ritonavir)", *Teva Pharmaceuticals USA, Inc. v. Corcept Therapeutics, Inc.*, Nov. 2016, pp. 1-64.
"KORLYM (Mifepristone)", Prescribing Information, May 2017, pp. 1-21.
"Korlym (Mifepristone) Tablets", Drug Approval Package, Application No. 202107, Available Online at: www.accessdata.fda.gov/drugsatfda_docs/nda/2012/202107_korlym toc.cfm], Accessed from Internet at May 7, 2019, pp. 1-2.
"Korlym Label", Available Online at: https://web.archive.org/web/20120304133653/www.corcept.com/prescribinginfo.pdf, Mar. 4, 2012, pp. 1-17.
"Korlym Label", Feb. 2012, pp. 1-23.
"Korlym Label Revised", May 2017, pp. 1-7.
"Korlym™ (Mifepristone) 300 mg Tablets", Reference ID: 3089791, TEVA1004, Feb. 17, 2012, pp. 1-23.
"Labeling", Korlym™ ((mifepristone) [package insert]; Center for Drug Evaluation and Research, Corcept Therapeutics, Inc., Feb. 2012, 26 pages.
"Letter Order", Case PGR2019-00048, *Teva Pharmaceuticals USA, Inc. v. Corcept Therapeutics, Inc.*, Corcept Ex. 2005, Jun. 4, 2019, pp. 1-2.
"Medical Encyclopedia", Medline Plus, Available Online at: http://www.nlm.nih.gov/medlineplus/ency/article/003430.htm, Oct. 2005, pp. 1-4.
"National Court-Reporting Coverage", *Teva Pharmaceuticals USA, Inc. v. Corcept Therapeutics, Inc.*, PGR2019-00048 Corcept Ex. 2059, Feb. 14, 2020, pp. 1-81.
"Nefazodone Hydrochloride Tablets", *Teva Pharmaceuticals USA, Inc. v. Corcept Therapeutics, Inc.*, May 2014, pp. 1-4.
"NIZORAL (ketoconazole)", Janssen Pharmaceuticals, Jul. 2013, pp. 1-22.
"NORVIR (Ritonavir)", Full Prescribing Information, *Teva Pharmaceuticals USA, Inc. v. Corcept Therapeutics, Inc.*, Dec. 2016, pp. 1-42.
"Notice Concerning Alternative Dispute Resolution", Case PGR2019-00048, May 24, 2019, pp. 1-6.
"Notice of Accepting Corrected Exhibit", Case PGR2019-00048, May 30, 2019, 2 pages.
"Notice of Deposition of Dr. David J. Greenblatt, M.D.", Case PGR2019-00048, Jan. 17, 2020, 4 pages.
"Notice of Joint Stipulation to Modify Trial Due Dates 1, 2 and 3", Case PGR2019-00048, Jan. 6, 2020, 4 pages.
"NOXAFIL (Posaconazole)", Full Prescribing Information, *Teva Pharmaceuticals USA, Inc. v. Corcept Therapeutics, Inc.*, Sep. 2016, pp. 1-37.
"Objections to Evidence", Case PGR2019-00048, Teva Pharmaceuticals USA, Inc.'s, Mar. 5, 2020, 5 pages.
"Order", Case PGR2019-00048, Oct. 3, 2019, pp. 1-3.
"Order", Case PGR2019-00048, Paper 24, Nov. 20, 2019, pp. 1-5.
"Order, Paper 22", Case PGR2019-00048, Nov. 20, 2019, 5 pages.
"Order, Paper 23", Case PGR2019-00048, Nov. 20, 2019, pp. 1-5.
"Patent Owner Mandatory Notices", Case PGR2019-00048, May 28, 2019, 5 pages.
"Patent Owner Response", Case PGR2019-00048, Feb. 27, 2020, 92 pages.
"Patent Owner's Objections to Evidence", Case PGR2019-00048, Dec. 5, 2019, 5 pages.

"Petitioner's Motion for Pro Hac Vice Admission of J.C. Rozendaal Under 37 C.F.R. § 42.10(C)", Case PGR2019-00048, Sep. 11, 2019, pp. 1-8.
"Petitioner's Motion for Pro Hac Vice Admission of Uma N. Everett Under 37 C.F.R. § 42.10(C)", Case PGR2019-00048, Sep. 11, 2019, pp. 1-7.
"Petitioner's Motion for Pro Hac Vice Admission of William H. Milliken Under 37 C.F.R. § 42.10(C)", Case PGR2019-00048, Sep. 11, 2019, pp. 1-8.
"Power of Attorney", Case PGR2019-00048, Teva Pharmaceuticals USA, Inc.'s, May 7, 2019, 3 pages.
"Power of Attorney for Proceedings Before the Patent Trial and Appeal Board", May 28, 2019, 1 page.
"Pretrial Scheduling Order", Civil Action No. 18-3632 (SDW)(CLW), United States District Court, District of New Jersey, Feb. 11, 2019, pp. 1-3.
"Scheduling Order, Paper 20", Case PGR2019-00048, Nov. 20, 2019, pp. 1-5.
"Second Declaration of Dr. David J. Greenblatt, M.D.", Case PGR2019-00048, U.S. Pat. No. 10,195,214 B2, *Teva Pharmaceuticals USA, Inc. v. Concept Therapeutics, Inc.*, Document No. 168, ExhibiUPaper No. 1067, Jun. 4, 2020, 15 pages.
"SPORANOX (Itraconazole)", Apr. 2015, 71 pages.
"TECHNIVIE (Ombitasvir, Paritaprevir and Ritonavir)", Feb. 2017, pp. 1-35.
"The Hazards of Seldane", The New York Times, Jan. 17, 1997, pp. 1-2.
"Transmittal Letter Accompanying Submission of Replacement Exhibit 1056", Case PGR2019-00048, May 28, 2019, 3 pages.
"Treatment for Aspergillosis", Centers for Disease Control and Prevention, Available Online at: https://www.cdc.gov/fungal/diseases/aspergillosis/treatment.html, Jan. 2, 2019, 1 page.
"Trial Practice Guide Update", *Teva Pharmaceuticals USA, Inc. v. Corcept Therapeutics, Inc.*, PGR2019-00048 Concept Ex. 2001, Aug. 2018, pp. 1-31.
"TYBOST (Cobicistat)", Jun. 2016, pp. 1-32.
"Updated Mandatory Notices", Case PGR2019-00048, Teva Pharmaceuticals USA, Inc.'s, Sep. 11, 2019, 3 pages.
"VAPRISOL (Conivaptan Hydrochloride)", Oct. 2016, pp. 1-14.
"VFEND (Voriconazole)", Feb. 2013, pp. 1-42.
"VICTRELIS (Boceprevir)", Jan. 2017, pp. 1-38.
"VIRACEPT (Nelfinavir Mesylate)", Sep. 2016, pp. 1-28.
"Virtual Deposition of F. Peter Guengerich", Case PGR2019-00048, U.S. Pat. No. 10,195,214 B2, *Teva Pharmaceuticals USA, Inc. v. Concept Therapeutics, Inc.*, Document No. 171, Exhibit/Paper No. 1070, Jun. 4, 2020, 208 pages.
U.S. Appl. No. 15/627,359, Final Office Action, Mailed On Jun. 12, 2018, 13 pages.
U.S. Appl. No. 15/627,359, Non-Final Office Action, Mailed On Oct. 20, 2017, 11 pages.
U.S. Appl. No. 15/627,359, Notice of Allowance, Mailed On Dec. 12, 2018, 10 pages.
U.S. Appl. No. 15/627,359, "Preliminary Invalidity Contentions", Defendant Teva Pharmaceuticals, Corcept Therapeutics, Civil Action No. 2: 18-cv-03632, May 13, 2019, 143 pages.
U.S. Appl. No. 15/627,359, "Rule 132 Declaration by Dr. Hanford K.S. Yau and CV", Jun. 28, 2018, 27 pages.
U.S. Appl. No. 15/627,359, "Rule 132 Declaration by Dr. Paul G. Pearson and CV", Jun. 28, 2018, 36 pages.
U.S. Appl. No. 15/627,359, "Rule 132 Declaration of Dr. Andreas Moraitis and CV", Jun. 28, 2018, 32 pages.
U.S. Appl. No. 15/627,359, "Rule 132, Declaration of Joseph K. Belanoff and CV", Dec. 15, 2017, 15 pages.
U.S. Appl. No. 15/627,368, Advisory Action, Mailed On Feb. 20, 2018, 3 pages.
U.S. Appl. No. 15/627,368, Advisory Action, Mailed On Mar. 2, 2018, 3 pages.
U.S. Appl. No. 15/627,368, Final Office Action, Mailed On Dec. 5, 2017, 10 pages.
U.S. Appl. No. 15/627,368, Final Office Action, Mailed On Jul. 5, 2019, 10 pages.
U.S. Appl. No. 15/627,368, Final Office Action, Mailed On Oct. 22, 2018, 8 pages.

(56) References Cited

OTHER PUBLICATIONS

U.S. Appl. No. 15/627,368, Non-Final Office Action, Mailed On Aug. 8, 2017, 11 pages.
U.S. Appl. No. 15/627,368, Non-Final Office Action, Mailed On Mar. 16, 2018, 13 pages.
U.S. Appl. No. 15/627,368, Non-Final Office Action, Mailed On Dec. 17, 2018, 14 pages.
U.S. Appl. No. 16/219,564, Notice of Allowance, Mailed On Oct. 19, 2020, 5 pages.
Aanderud et al., "Plasma Cortisol Concentrations After Oral Substitution of Cortisone in the Fasting and Non-Fasting State", Acta Medica Scandinavica, vol. 210, No. 3, Jan.-Dec. 1981, pp. 157-161.
Albertson et al., "Effect of the Antiglucocorticoid RU486 on Adrenal Steroidogenic Enzyme Activity and Steroidogenesis", European Journal of Endocrinology, vol. 130, No. 2, Feb. 1994, pp. 195-200.
Asser et al., "Autocrine Positive Regulatory Feedback of Glucocorticoid Secretion: Glucocorticoid Receptor Directly Impacts H295R Human Adrenocortical Cell Function", Molecular and Cellular Endocrinology, vol. 395, Nos. 1-2, Sep. 2014, pp. 1-9.
Bagchus et al., "Important Effect of Food on the Bioavailability of Oral Testosterone Undecanoate", Pharmacotherapy, vol. 23, No. 3, Mar. 2003, pp. 319-325.
Bailey et al., "Grapefruit-Medication Interactions: Forbidden Fruit or Avoidable Consequences?", Canadian Medical Association Journal, vol. 185, No. 4, Mar. 5, 2013, pp. 309-316.
Banankhah et al., "Ketoconazole-Associated Liver Injury in Drug-Drug Interaction Studies in Healthy Volunteers", The Journal of Clinical Pharmacology, vol. 56, No. 10, Oct. 2016, pp. 1196-1202.
Basina et al., "Successful Long-Term Treatment of Cushing Disease with Mifepristone (RU 486)", Endocrine Practice, vol. 18, No. 5, Sep.-Oct. 2012, 7 pages.
Belanoff et al., "An Open Label Trial of C-1073 (Mifepristone) for Psychotic Major Depression", Biological Psychiatry, vol. 52, No. 5, Sep. 1, 2002, pp. 386-392.
Benagiano et al., "Selective Progesterone Receptor Modulators 3: Use in Oncology, Endocrinology and Psychiatry", Expert Opinion Pharmacotherapy, vol. 9, No. 14, Oct. 2008, pp. 2487-2496.
Benet et al., "Pharmacokinetics: The Dynamics of Drug Absorption, Distribution and Elimination", Chapter 1, Goodman & Gilman's: The Pharmacological Basis of Therapeutics, Eighth Edition, 1990, pp. 3-32.
Bertagna et al., "Chapter 16: Cushing's Disease", The Pituitary (Shlomo Melmed, 3rd Edition), Part 1, 2011, pp. 533-577.
Bertagna et al., "Chapter 16: Cushing's Disease", The Pituitary (Shlomo Melmed, 3rd Edition), Part 2, 2011, pp. 578-617.
Bertagna et al., "Pituitary-Adrenal Response to the Antiglucocorticoid Action of RU 486 in Cushing's Syndrome", Journal of Clinical Endocrinology and Metabolism, vol. 63, No. 3, Sep. 1986, pp. 639-643.
Berthois et al., "A Multiparametric Analysis of Endometrial Estrogen and Progesterone Receptors After the Postovulatory Administration of Mifepristone", Fertility and Sterility, vol. 55, No. 3, Mar. 1991, pp. 547-554.
Blasey et al., "Efficacy and Safety of Mifepristone for the Treatment of Psychotic Depression", Journal of Clinical Psychopharmacology, vol. 31, No. 4, Aug. 2011, pp. 436-440.
Brogden et al., "Mifepristone: A Review of its Pharmacodynamic and Pharmacokinetic Properties, and Therapeutic Potential", Drugs, vol. 45, No. 3, Mar. 1993, pp. 384-409.
Carroll et al., "The Use of Mifepristone in the Treatment of Cushing's Syndrome", Drugs of Today, vol. 48, No. 8, Aug. 2012, pp. 509-518.
Cassier et al., "Mifepristone for Ectopic ACTH Secretion in Metastic Endocrine Carcinomas: Report of Two Cases", European Journal of Endocrinology, vol. 158, No. 6, Jun. 2008, pp. 935-938.
Castinetti et al., "Ketoconazole in Cushing's Disease: Is It Worth a Try?", The Journal of Clinical Endocrinology & Metabolism, vol. 99, No. 5, May 2014, pp. 1623-1630.

Castinetti et al., "Medical Treatment of Cushing's Syndrome: Glucocorticoid Receptor Antagonists and Mifepristone", Neuroendocrinology, vol. 92, 2010, pp. 125-130.
Castinetti et al., "Merits and Pitfalls of Mifepristone in Cushing's Syndrome", European Journal of Endocrinology, vol. 160, No. 6, Jun. 2009, pp. 1003-1010.
Ceccato et al., "Therapeutic Strategies for Cushing's Syndrome: An Update", Expert Opinion On Orphan Drugs, vol. 3, No. 1, Dec. 10, 2014, pp. 45-56.
Charmandari et al., "Adrenal Insufficiency", Lancet, vol. 383, No. 9935, Available Online at: https://www.thelancet.com/journals/lancet/article/PIIS0140-6736(13)61684-0/fulltext, Feb. 4, 2014, pp. 1-16.
Chrousos et al., "Glucocorticoids and Glucocorticoid Antagonists: Lessons from RU 486", Antiglucocorticoids, Kidney International, vol. 34, Oct. 1988, pp. S-18-S-23.
Chu et al., "Successful Long-Term Treatment of Refractory Cushing's Disease with High-Dose Mifepristone (RU 486)", The Journal of Clinical Endocrinology & Metabolism, vol. 86, No. 8, Aug. 2001, pp. 3568-3573.
Clayton et al., "Mortality in Patients with Cushing's Disease More Than 10 Years After Remission: A Multicentre, Multinational, Retrospective Cohort Study", Lancet Diabetes Endocrinology, vol. 4, No. 7, Jul. 2016, pp. 569-576.
Application No CN201880014847.1, Office Action, Mailed On Apr. 2, 2022, 13 pages.
Cuevas-Ramos et al., "Treatment of Cushing's Disease: A Mechanistic Update", Journal of Endocrinology, vol. 223, No. 2, Nov. 2014, pp. R19-R39.
Cuevas-Ramos et al., "Update on Medical Treatment for Cushing's Disease", Clinical Diabetes and Endocrinology, vol. 2, No. 16, Sep. 13, 2016, pp. 1-13.
Cuneo et al., "Metyrapone Pre-Treated Inferior Petrosal Sinus Sampling in the Differential Diagnosis of ACTH-Dependent Cushing's Syndrome", Clinical Endocrinology, vol. 46, No. 5, May 1997, pp. 607-618.
Dang et al., "Pharmacological Management of Cushing's Syndrome: An Update", Arq Bras Endocrinol Metab, vol. 51, No. 8, Nov. 2007, pp. 1339-1348.
Davis et al., "Guidelines for Counselling Patients Receiving Drugs Used in the Treatment of Neoplastic Disease: A Pharmacist's Guide to Advisory Labels and Patient Information", The Australian Journal of Hospital Pharmacy, vol. 31, No. 1, Mar. 2001, pp. 51-55.
De Lignieres, "Oral Micronized Progesterone", Clinical Therapeutics, vol. 21, No. 1, Jan. 1999, pp. 41-60.
Dunnigan et al., "Mifepristone (RU-486) in the Treatment of Refractory Cushing's Disease", Endocrine Reviews, vol. 31, No. 3, Jun. 2010, 9 pages.
Ehrenkranz et al., "SUN-66: Using Mifepristone to Differentiate Cushing's Disease From Cushing's Syndrome", The Endocrine Society's 95th Annual Meeting and Expo, Jun. 15-18, 2013, 6 pages.
El-Shafie et al., "Adrenocorticotropic Hormone-Dependent Cushing's Syndrome: Use of an Octreotide Trial to Distinguish Between Pituitary or Ectopic Sources", Sultan Qaboos University Medical Journal, vol. 15, No. 1, Feb. 2015, pp. 120-123.
Application No. EP18760940.9, Extended European Search Report, Mailed On Nov. 27, 2020, 8 pages.
Feelders et al., "The Burden of Cushing's Disease: Clinical and Health-Related Quality of Life Aspects", European Journal of Endocrinology, vol. 167, No. 3, Sep. 2012, pp. 311-326.
Fein et al., "Sustained Weight Loss in Patients Treated with Mifepristone for Cushing's Syndrome: A Follow-Up Analysis of the SEISMIC Study and Long-Term Extension", BMC Endocrine Disorders, vol. 15, No. 63, Oct. 27, 2015, 7 pages.
Fleseriu et al., "A New Therapeutic Approach in the Medical Treatment of Cushing's Syndrome: Glucocorticoid Receptor Blockade with Mifepristone", Endocrine Practice, vol. 19, No. 2, Mar. 1, 2013, pp. 313-326.
Fleseriu et al., "Changes in Plasma ACTH Levels and Corticotroph Tumor Size in Patients with Cushing's Disease During Long-Term Treatment with the Glucocorticoid Receptor Antagonist Mifepristone", Journal of Clinical Endocrinology Metabolism, vol. 99, No. 10, Oct. 2014, pp. 3718-3727.

(56) References Cited

OTHER PUBLICATIONS

Fleseriu et al., "Mifepristone, a Glucocorticoid Receptor Antagonist, Produces Clinical and Metabolic Benefits in Patients with Cushing's Syndrome", The Journal of Clinical Endocrinology & Metabolism, vol. 97, No. 6, Mar. 30, 2012, pp. 2039-2049.

Fleseriu et al., "New Avenues in the Medical Treatment of Cushing's Disease: Corticotroph Tumor Targeted Therapy", Journal of Neuro-Oncology, vol. 114, No. 1, Aug. 2013, pp. 1-11.

Friedman et al., "Rational Therapeutic Drug Monitoring", JAMA, vol. 256, No. 16, Oct. 24-31, 1986, pp. 2227-2233.

Gal et al., "Effect of Ketoconazole on Steroidogenic Human Granulosa-Luteal Cells in Culture", European Journal of Obstetrics & Gynecology and Reproductive Biology, vol. 39, No. 3, May 10, 1991, pp. 209-214.

Gallagher et al., "Mifepristone (RU-486) Treatment for Depression and Psychosis: A Review of the Therapeutic Implications", Neuropsychiatric Disease and Treatment, vol. 2, No. 1, Mar. 2006, pp. 33-42.

Greenblatt, "Clinical Pharmacokinetics", The New England Journal of Medicine, vol. 293, No. 14, Oct. 2, 1975, pp. 702-705.

Greenblatt et al., "Clinical Studies of Drug-Drug Interactions: Design and Interpretation", Springer, 2010, pp. 625-649.

Greenblatt, "Concomitant Administration of Glucocorticoid Receptor Modulators and CYP3A Inhibitors", Petition for Post-Grant Review, U.S. Pat. No. 10,195,214, TEVA1002-Declaration of Dr. David J. Greenblatt, M.D., May 7, 2019, 118 pages.

Greenblatt, "Curriculum Vitae", TEVA 1003, Apr. 2019, 83 pages.

Greenblatt, "Drug-Drug Noninteractions", Cardiovascular Therapeutics, vol. 27, No. 4, 2009, pp. 226-229.

Greenblatt, "In Vitro Prediction of Clinical Drug Interactions with CYP3A Substrates: We Are Not There Yet", Clinical Pharmacology & Therapeutics, vol. 95, No. 2, Feb. 2014, pp. 133-135.

Greenblatt et al., "Ketoconazole Inhibition of Triazolam and Alprazolam Clearance: Differential Kinetic and Dynamic Consequences", Clinical Pharmacology and Therapeutics, vol. 64, No. 3, Sep. 1998, pp. 237-247.

Greenblatt et al., "Kinetic and Dynamic Interaction Study of Zolpidem with Ketoconazole, Itraconazole and Fluconazole", Clinical Pharmacology & Therapeutics, vol. 64, No. 6, Dec. 1998, pp. 661-671.

Greenblatt et al., "Liver Injury Associated with Ketoconazole: Review of the Published Evidence", The Journal of Clinical Pharmacology, vol. 54, No. 12, Dec. 2014, pp. 1321-1329.

Greenblatt et al., "Mechanism of Cytochrome P450-3A Inhibition by Ketoconazole", Journal of Pharmacy and Pharmacology, vol. 63, No. 2, Feb. 2011, pp. 214-221.

Greenblatt et al., "Pharmacokinetics and Pharmacodynamics for Medical Students: A Proposed Course Outline", The Journal of Clinical Pharmacology, vol. 56, No. 10, Oct. 2016, pp. 1180-1195.

Greenblatt et al., "Ritonavir is the Best Alternative to Ketoconazole as an Index Inhibitor of Cytochrome P450-3A in Drug-Drug Interaction Studies", British Journal of Clinical Pharmacology, vol. 80, No. 3, Sep. 2015, pp. 342-350.

Greenblatt et al., "The CYP3 Family", Cytochromes P450: Role in the Metabolism and Toxicity of Drugs and Other Xenobiotics, Royal Society of Chemistry, Chapter 11, Jan. 2008, pp. 354-383.

Gross et al., "Mifepristone Reduces Weight Gain and Improves Metabolic Abnormalities Associated with Risperidone Treatment in Normal Men", Obesity, vol. 18, No. 12, Dec. 2010, pp. 2295-2300.

Guelho et al., "Emerging Drugs for Cushing's Disease", Expert Opinion on Emerging Drugs, vol. 20, No. 3, Sep. 2015, pp. 463-478.

Healy et al., "Pituitary and Adrenal Responses to the Anti-Progesterone and Anti-Glucocorticoid Steroid RU 486 in Primates", Journal of Clinical Endocrinology and Metabolism, vol. 57, No. 4, Oct. 1983, pp. 863-865.

Heikinheimo et al., "Antiprogesterone RU 486—A Drug for Non-Surgical Abortion", Annals of Medicine, vol. 22, No. 2, Apr. 1990, pp. 75-84.

Heikinheimo, "Clinical Pharmacokinetics of Mifepristone", Clinical Pharmacokinetics, vol. 33, No. 1, Jul. 1997, pp. 7-17.

Heikinheimo, "Pharmacokinetics of the Antiprogesterone RU 486 in Women During Multiple Dose Administration", The Journal of Steroid Biochemistry and Molecular Biology, vol. 32, No. 1A, Jan. 1989, pp. 21-25.

Heikinheimo et al., "The Pharmacokinetics of Mifepristone in Humans Reveal Insights Into Differential Mechanisms of Antiprogestin Action", Contraception, vol. 68, No. 6, Dec. 2003, pp. 421-426.

Huang et al., "Pharmacokinetics and Dose Proportionality of Ketoconazole in Normal Volunteers", Antimicrobial Agents and Chemotherapy, vol. 30, No. 2, Aug. 1986, pp. 206-210.

Im et al., "Mifepristone: Pharmacology and Clinical Impact in Reproductive Medicine, Endocrinology and Oncology", Expert Opinion on Pharmacotherapy, Drug Evaluation, vol. 11, No. 3, Feb. 2010, pp. 481-488.

Jang et al., "Identification of CYP3A4 as the Principal Enzyme Catalyzing Mifepristone (RU 486) Oxidation in Human Liver Microsomes", Biochem. Pharmacol., vol. 52, No. 5, Sep. 13, 1996, pp. 753-761.

Johanssen et al., "Mifepristone (RU 486) in Cushing's Syndrome", European Journal of Endocrinology, vol. 157, No. 5, Nov. 2007, pp. 561-569.

Application No. JP2019-547316, Office Action, Mailed On Jun. 17, 2022, 7 pages.

Kaeser et al., "Drug-Drug Interaction Study of Ketoconazole and Ritonavir-Boosted Saquinavir", Antimicrobial Agents and Chemotherapy, vol. 53, No. 2, Feb. 2009, pp. 609-614.

Kaushik et al., "Concomitant Administration of Glucocorticoid Receptor Modulators and CYP3A Inhibitors", Petition for Post-Grant Review, U.S. Pat. No. 10,195,214, Declaration of Atul Kaushik, May 7, 2019, 5 pages.

Ke et al., "Itraconazole and Clarithromycin as Ketoconazole Alternatives for Clinical CYP3A Inhibition Studies", Clinical Pharmacology & Therapeutics, vol. 95, No. 5, May 2014, pp. 473-476.

Korean Patent Application No. 10-2019-7028226, Office Action, Mailed On Oct. 18, 2022, 6 pages.

Kumar et al., "Cytochrome P450-Mediated Metabolism of the HIV-1 Protease Inhibitor Ritonavir (ABT-538) in Human Liver Microsomes", The Journal of Pharmacology and Experimental Therapeutics, vol. 277, No. 1, Apr. 1996, pp. 423-431.

Latrille et al., "A Comparative Study of the Effects of Ketoconazole and Fluconazole on 17-ß Estradiol Production by Rat Ovaries in Vitro", Research Communications in Chemical Pathology and Pharmacology, vol. 64, No. 1, Apr. 1989, pp. 173-177.

Lee et al., "Office of Clinical Pharmacology Review Memorandum", NDA 20687, Addendum, Korlym™, Mifepristone, Jan. 13, 2012, 119 pages.

Lindberg, "Emergency Contraception: The Nurse's Role in Providing Postcoital Options", Journal of Obstetric, Gynecologic, & Neonatal Nursing, vol. 26, No. 2, Mar.-Apr. 1997, pp. 145-152.

Locniskar et al., "Interaction of Diazepam with Famotidine and Cimetidine, Two H2-Receptor Antagonists", The Journal of Clinical Pharmacology, vol. 26, No. 4, Apr. 1986, pp. 299-303.

Luft, "Novel Cell Therapy for Type 1 Diabetes Mellitus", Journal of Molecular Medicine, vol. 87, May 9, 2009, pp. 659-661.

Molitch, "Current Approaches to the Pharmacological Management of Cushing's Disease", Molecular and Cellular Endocrinology, vol. 408, Jun. 15, 2015, pp. 185-189.

Moncet et al., "Ketoconazole Therapy: An Efficacious Alternative to Achieve Eucortisolism in Patients with Cushing's Syndrome", Medicina (B Aires), vol. 67, No. 1, 2007, pp. 26-31.

Morgan et al., "Mifepristone for Management of Cushing's Syndrome", Pharmacotherapy, vol. 33, No. 3, 2013, pp. 319-329.

Nguyen et al., "Effects of Ketoconazole on the Pharmacokinetics of Mifepristone, a Competitive Glucocorticoid Receptor Antagonist, in Healthy Men", Advances in Therapy, vol. 34, No. 10, Oct. 2017, pp. 2371-2385.

Nieman et al., "Successful Treatment of Cushing's Syndrome with the Glucocorticoid Antagonist RU 486", Journal of Clinical Endocrinology Metabolism, vol. 61, No. 3, Sep. 1985, pp. 536-540.

Ohno et al., "General Framework for the Quantitative Prediction of CYP3A4-Mediated Oral Drug Interactions Based on the AUC Increase by Coadministration of Standard Drugs", Clinical Pharmacokinetics, vol. 46, No. 8, 2007, pp. 681-696.

(56) References Cited

OTHER PUBLICATIONS

Oosterhuis et al., "Life-Threatening Pneumocystis Jiroveci Pneumonia Following Treatment of Severe Cushing's Syndrome", The Netherlands Journal of Medicine, vol. 65, No. 6, Jun. 2007, pp. 215-217.
Outeiro et al., "No Increased Risk of Ketoconazole Toxicity in Drug-Drug Interaction Studies", The Journal of Clinical Pharmacology, vol. 56, No. 10, Oct. 2016, pp. 1203-1211.
Para et al., "Phase I/II Trial of the Anti-HIV Activity of Mifepristone in HIV-Infected Subjects ACTG 5200", Journal of Acquired Immune Deficiency Syndromes, vol. 53, No. 4, Apr. 1, 2010, pp. 491-495.
PARKS, "NDA 202107", Department of Health and Human Services, Available online: https://www.accessdata.fda.gov/drugsatfda_docs/appletter/2012/202107s000ltr.pdf, Feb. 17, 2012, pp. 1-5.
International Patent Application No. PCT/EP2008/063699, International Search Report and Written Opinion, Mailed On May 6, 2009, 12 pages.
International Patent Application No. PCT/US2017/013974, International Search Report and Written Opinion, Mailed On Apr. 20, 2017, 12 pages.
International Patent Application No. PCT/US2018/020336, International Preliminary Report on Patentability, Mailed On Sep. 12, 2019, 9 pages.
International Patent Application No. PCT/US2018/020336, International Search Report and Written Opinion, Mailed On May 15, 2018, 11 pages.
Pivonello et al., "The Treatment of Cushing's Disease", Endocrine Reviews, vol. 36, No. 4, Aug. 2015, pp. 385-486.
Pozza et al., "Management Strategies for Aggressive Cushing's Syndrome: From Macroadenomas to Ectopics", Journal of Oncology, vol. 2012, Aug. 9, 2012, pp. 1-9.
Reimondo et al., "The Corticotrophin-Releasing Hormone Test is the Most Reliable Noninvasive Method to Differentiate Pituitary from Ectopic ACTH Secretion in Cushing's Syndrome", Clinical Endocrinology, vol. 58, No. 6, Jun. 2003, pp. 718-724.
Ritzel et al., "ACTH After 15 Min Distinguishes Between Cushing's Disease and Ectopic Cushing's Syndrome: A Proposal for a Short and Simple CRH Test", European Journal of Endocrinology, vol. 173, No. 2, Aug. 2015, pp. 197-204.
Saav et al., "Medical Abortion in Lactating Women—Low Levels of Mifepristone in Breast Milk", Acta Obstetricia et Gynecologica Scandinavica, vol. 89, No. 5., May 2010, pp. 618-622.
Sarkar, "Mifepristone: Bioavailability, Pharmacokinetics and Use-Effectiveness", European Journal of Obstetrics & Gynecology and Reproductive Biology, vol. 101, No. 2, Mar. 10, 2002, pp. 113-120.
Sartor et al., "Mifepristone: Treatment of Cushing's Syndrome", Clinical Obstetrics and Gynecology, vol. 39, No. 2, Jun. 1996, pp. 506-510.
Schteingart, "Drugs in the Medical Treatment of Cushing's Syndrome", Expert Opinion on Emerging Drugs, vol. 14, No. 4, Dec. 2009, pp. 661-671.
Schteingart, "Drugs in the Medical Treatment of Cushing's Syndrome—An Update on Mifepristone and Pasireotide", Expert Opinion on Emerging Drugs, vol. 17, No. 3, Apr. 25, 2012, pp. 279-283.
Shi et al., "Pharmacokinetic Study of RU 486 and Its Metabolites After Oral Administration of Single Doses to Pregnant and Non-Pregnant Women", Clinical Article, Contraception, vol. 48, No. 2, Aug. 1993, pp. 133-149.
Sitruk-Ware et al., "Pharmacological Properties of Mifepristone: Toxicology and Safety in Animal and Human Studies", Contraception, vol. 68, No. 6, Dec. 2003, pp. 409-420.
Tran et al., "Translation of Drug Interaction Knowledge to Actionable Labeling", Clinical Pharmacology & Therapeutics, vol. 105, No. 6, Jun. 2019, pp. 1292-1295.
Tritos et al., "Medical Management of Cushing's Disease", Journal of Neuro-Oncology, vol. 117, 2014, pp. 407-414.
Truong et al., "Budget Impact of Pasireotide for the Treatment of Cushing's Disease, a Rare Endocrine Disorder Associated with Considerable Comorbidities", Journal of Medical Economics, vol. 17, No. 4, Apr. 2014, pp. 288-295.
Tsigos et al., "Differential Diagnosis and Management of Cushing's Syndrome", Annual Review of Medicine, vol. 47, 1996, pp. 443-461.
Tsunoda et al., "Differentiation of Intestinal and Hepatic Cytochrome P450 3A Activity with Use of Midazolam as an in Vivo Probe: Effect of Ketoconazole", Clinical Pharmacology and Therapeutics, vol. 66, No. 5, Nov. 1999, pp. 461-471.
Van Der Lelij, "Aspects of Medical Therapy of Neuroendocrine Disorders", Thesis, 1992, 166 pages.
Van Der Lely et al., "Rapid Reversal of Acute Psychosis in the Cushing Syndrome with the Cortisol-Receptor Antagonist Mifepristone (RU 486)", Annals of Internal Medicine, vol. 114, No. 2, Jan. 15, 1991, pp. 143-144.
Varis et al., "The Effect of Itraconazole on the Pharmacokinetics and Pharmacodynamics of Oral Prednisolone", European Journal of Clinical Pharmacology, vol. 56, No. 1, Apr. 2000, pp. 57-60.
Viera et al., "Potassium Disorders: Hypokalemia and Hyperkalemia", American Family Physician, vol. 92, No. 6, Sep. 15, 2015, pp. 487-495.
Von Moltke et al., "In Vitro Approaches to Predicting Drug Interactions In Vivo", Biochemical Pharmacology, vol. 55, No. 2, Jan. 15, 1998, pp. 113-122.
Von Moltke et al., "Metabolism of Drugs by Cytochrome P450 3A Isoforms", Clinical Pharmacokinetic, vol. 29, 1995, pp. 33-44.
Wilkinson, "Pharmacokinetics: The Dynamics of Drug Absorption, Distribution and Elimination", Goodman & Gilmans' The Pharmacological Basis of Therapeutics, Tenth Edition, 2001, 30 pages.
Zhang et al., "Predicting Drug-Drug Interactions: An FDA Perspective", The AAPS Journal, vol. 11, No. 2, Jun. 2009, pp. 300-306.
U.S. Appl. No. 15/627,359, "Rule 132, Second Declaration of Joseph K. Belanoff", Jan. 22, 2018, 2 pages.
U.S. Appl. No. 15/627,368, "Rule 132, Declaration of Dr. Handord K.S. Yau and CV", Jun. 28, 2018, 27 pages.
Gardner et al., "Greenspan's Basic & Clinical Endocrinology, Tenth Edition", Chapter 10, McGraw-Hill Education, 2018, 3 pages.

CONCOMITANT ADMINISTRATION OF GLUCOCORTICOID RECEPTOR MODULATORS AND CYP3A INHIBITORS

CROSS-REFERENCE TO RELATED APPLICATIONS

This application is a continuation of, claims priority to, and the benefit of, U.S. application Ser. No. 17/544,859, filed Dec. 7, 2021, which is a continuation of U.S. application Ser. No. 16/482,656, filed Jul. 31, 2019, now abandoned, which is a 371 National Stage Application of PCT/US2018/020336, filed Feb. 28, 2018, which claims the benefit of U.S. Provisional Application No. 62/466,867, filed Mar. 3, 2017 and 62/465,772, filed Mar. 1, 2017. Each and every one of the above patent applications is hereby incorporated by reference in its entirety for all purposes.

BACKGROUND

Steroid molecules, such as steroid hormones, play an important role in bodily functions and in bodily responses to infectious and other diseases, and to the environment. Many steroid molecules are synthesized in the body, or are produced from molecules consumed in the diet. Steroid molecules which act as hormones in the body include estrogen, progesterone, testosterone, and cortisol. Some steroid molecules have medicinal effects. Inhibition of steroid synthesis or metabolism can be useful in the treatment of some disorders.

Cortisol, a steroid molecule, plays an important role in many bodily functions. Cortisol exerts effects by binding to cortisol receptors, which are present in most tissues in the body. However, dysregulation of cortisol may have adverse effects on a subject. For example, Cushing's syndrome, caused by excess levels of cortisol, is characterized by symptoms including elevated blood pressure, elevated blood glucose, increased weight, increased mid-section perimeter, other pre-diabetic symptom, a "moon-face" facial appearance, immune suppression, thin skin, acne, depression, hirsutism, and other symptoms. Clinical manifestations of Cushing's syndrome include abnormalities in glucose control, requirement for anti-diabetic medication, abnormalities in insulin level, abnormal psychiatric symptoms, cushingoid appearance, acne, hirsutism, and increased or excessive body weight, and other symptoms.

One effective treatment of cortisol dysregulation is to block the binding of cortisol to cortisol receptors, or to block the effect of cortisol binding to cortisol receptors. Mifepristone binds to cortisol receptors, and acts to block such binding and to block the effect of cortisol on tissues. Mifepristone is 11β-(4-dimethylaminophenyl)-17β-hydroxy-17α-(1-propynyl)-estra-4,9-dien-3-one).

Another effective treatment of cortisol dysregulation is to reduce the synthesis of cortisol, e.g., by reducing or blocking steroid synthesis. A "steroidogenesis inhibitor" is a compound which reduces or blocks the synthesis of steroid molecules (including, e.g., cortisol) when administered to a subject. Steroidogenesis inhibitors include, for example, ketoconazole, metyrapone, etomidate, and other drugs.

Many enzymes are involved in steroid synthesis and in steroid metabolism, including cytochrome P450 enzymes, encoded by CYP genes. Inhibiting steroid synthesis may lower the levels of steroids, including, e.g., cortisol, in the blood. For example, CYP3A enzymes play important roles in the synthesis of steroid hormones such as cortisol. In addition, such enzymes may also metabolize drugs that may be administered to subjects. For example, cytochrome P450 3A4 (CYP3A4) has been shown to be involved in mifepristone metabolism in human liver microsomes.

However, many drugs inhibit the levels or actions of CYP3A gene products (termed "inhibit CYP3A"). The following drugs inhibit CYP3A: ketoconazole, itraconazole, fluconazole, cimetidine, nefazodone, ritonavir, nelfinavir, indinavir, atazanavir, amprenavir, fosamprenavir, boceprevir, clarithromycin, conivaptan, lopinavir, posaconazole, saquinavir, telaprevir, telithromycin, and voriconazole, among many drugs which inhibit CYP3A. For example, the following drugs strongly inhibit CYP3A (i.e., increase AUC (area under the concentration-time curve) by 10-fold or greater of sensitive index substrates), either alone or in combination with other drugs: boceprevir, cobicistat, conivaptan, danoprevir and ritonavir, elvitegravir and ritonavir, indinavir, ritonavir, itraconazole, ketoconazole, lopinavir, pantaprevir, ombitasvir, dasabuvir, posaconazole, saquinavir, telaprevir, tipranavir, troleandomycin, and voriconazole.

Ketoconazole is an exemplary and an important steroidogenesis inhibitor and is a strong CYP3A inhibitor. Ketoconazole (chemical name: 1-acetyl-4-[4-[[2-(2,4-dichlorophenyl)-2-[(1H-imidazol-1-yl)-methyl]-1,3-dioxolan-4-yl]methoxy]phenyl]piperazine) is administered for the treatment of fungal infections; it also affects steroid metabolism by inhibiting steroidogenesis, and has anti-glucocorticoid and anti-androgen effects due to its interference with enzymatic conversion of cholesterol to hormones such as cortisol and testosterone. Ketoconazole has effects on liver enzymes and the gastrointestinal (GI) tract, among other effects (Fleseriu and Castinetti, *Pituitary* 19:643-653 (2016)).

Ketoconazole inhibits steroid synthesis and is thus useful in the treatment Cushing's syndrome; in the treatment of prostate cancer and other androgen-sensitive cancers; to reduce estrogen or progesterone production (e.g., in patients with hormone-sensitive cancers such as breast cancer and ovarian cancer); and in other treatments.

A drug such as ketoconazole is typically metabolized and excreted by a subject over time following administration. An effective dose is determined based on the expected amounts of metabolism and excretion of the drug. Changes in the amounts or rates of metabolism and/or excretion of a drug will affect the dose required, and may make an otherwise safe dose, if metabolism or excretion changes, into either a less, or ineffective dose, or a more effective or even toxic dose.

However, although sometimes clinically useful, ketoconazole may have adverse, including seriously toxic, effects (Fleseriu and Castinetti, *Pituitary* 19:643-653 (2016)). The U.S. Food and Drug Administration issued a Drug Safety Communication (Jul. 26, 2013 Safety Announcement regarding NIZORAL® (ketoconazole)) warning of potentially fatal liver damage associated with oral ketoconazole treatment and warning of the risk of adrenal insufficiency, also a potentially fatal disorder. The Safety Announcement warned: "Nizoral tablets can cause liver injury, which may potentially result in liver transplantation or death." The Safety Announcement further stated: "Nizoral tablets may interact with other drugs a patient is taking and can result in serious and potentially life-threatening outcomes, such as heart rhythm problems." Thus, ketoconazole can be quite toxic if administered in excessive amounts, or if it is administered to sensitive individuals, particularly when administered systemically (as opposed, e.g., to topically). This toxicity can lead to liver damage (sometimes requiring liver transplantation). Other CYP3A inhibitors, including, e.g., itraconazole, ritonavir, and other CYP3A inhibitors as discussed herein, may have similar effects and may require similar warnings.

The simultaneous, or nearly simultaneous (e.g., concomitant) presence of two drugs in a subject may alter the effects of one or the other, or both, drugs. Such alterations are termed drug-drug interactions. For example, the required dose of a drug is often strongly affected by taking the amount and rate of its degradation in, and elimination from, the body (e.g., by liver or kidney action). However, the presence of a second drug in the body, which is also being acted upon by the liver and kidney, can have significant effects on the amount and rate of degradation of the first drug, and can increase the amount of the first drug that remains in the body at a given time beyond the amount that would have been present at that time in the absence of the second drug. Thus, the presence of a second drug can often increase the effective dose of the first drug. Where the first drug has toxic side effects, such an increase in effective dose of the first drug may lead to dangerous toxicity that would not have been expected were the second drug not present.

Concomitant administration of different drugs often leads to adverse effects since the metabolism and/or excretion of each drug may reduce or interfere with the metabolism and/or excretion of the other drug(s), thus increasing the effective concentrations of those drugs as compared to the effective concentrations of those drugs when administered alone. Thus, concomitant administration of drugs is often expected to increase the risk of toxic effects of one or both of the co-administered drugs. Some drugs, such as ketoconazole, present risk of liver damage (including severe cases including liver failure and even requiring liver transplants) and other toxic effects when administered alone; the risk of such toxic effects is believed to be increased when other drugs are concomitantly administered. Where a drug, such as ketoconazole, is known to present a high risk of toxic effects, clinicians will typically avoid its concomitant administration with other drugs.

The plasma levels of a drug are affected not only by the amount administered, but may also be affected by the amount (and rate) of its metabolism. For this reason, regulatory agencies typically require "drug-drug interaction" (DDI) studies to determine the effects of concomitant administration of drugs. Many enzymes, including cytochrome P450 enzymes (e.g., the cytochrome P450-3A enzymes, termed "CYP3A" enzymes), provide significant amounts of the metabolism of administered drugs. Drugs that inhibit metabolic enzymes such as CYP3A can cause increases in the plasma levels of other drugs which are administered or are present at times where there are sufficient levels of both drugs in a subject. Such increases can be significant. For example, Greenblatt et al. (Brit. J. Clin. Pharmacol. 80(3):342-350 (2015) reviewed 38 published studies involving 411 subjects, and report that concomitantly administered representative CYP3A inhibitors increased plasma levels of orally administered midazolam (as measured by the area under the concentration-time curve "AUC") by more than 11-fold (ketoconazole); more than 7-fold (itraconazole); more than 6-fold (clarithromycin); and more than 14-fold (ritonavir). Thus, CYP3A inhibitors typically have a very large effect on plasma levels of other, concomitantly administered, drugs.

The U.S. The Food and Drug Administration (FDA) notes that "Patients frequently use more than one medication at a time. Unanticipated, unrecognized, or mismanaged DDIs [drug-drug interactions] are an important cause of morbidity and mortality associated with prescription drug use" (page 2 of "Clinical Drug Interaction Studies—Study Design, Data Analysis, and Clinical Implications Guidance for Industry"). This same U.S. FDA report names multiple "strong CYP3A" inhibitors (increasing AUC of sensitive CYP3A substrates by more than 5-fold), including many (e.g., ketoconazole, itraconazole, ritonavir, boceprevir, cobicistat, conivaptan, telaprevir, troleandomycin, and variconazole, among others) which increase AUC of sensitive CYP3A substrates by more than 10-fold. Thus, large plasma level increases of greater than 5-fold or greater than 10-fold would be expected for CYP3A substrates, such as mifepristone, when concomitantly administered with a strong CYP3A inhibitor such as, e.g., ketoconazole, itraconazole, ritonavir, or others.

The use of ketoconazole, itraconazole, or of some other drug along with, e.g. mifepristone, may be thought to be required for successful treatment of a patient. However, since concomitant administration of a CYP3A substrate (such as, e.g., mifepristone or other glucocorticoid receptor modulator) with a CYP3A inhibitor (such as ketoconazole, itraconazole, or others) would be expected to raise the levels of the CYP3A substrate to unsafe levels, or could expose the patient to dangerous or toxic effects of one or the other drug, a physician may forego the concomitant use of ketoconazole, itraconazole, or other drug which may have otherwise been thought to be required for successful treatment.

However, patients may require treatment with multiple drugs, despite the possible disadvantages that can have deleterious consequences for the patient.

Accordingly, improved methods of treatment allowing the administration of other drugs along with CYP3A inhibitors (such as, e.g., ketoconazole, itraconazole, and others) and along with steroidogenesis inhibitors (such as, e.g., ketoconazole, itraconazole, and others) are desired.

SUMMARY

Applicant discloses herein that CYP3A inhibitors such as, e.g., ketoconazole, itraconazole, and others, may be concomitantly administered with glucocorticoid receptor modulators (GRMs) such as the GR antagonist (GRA) mifepristone. Such concomitant administration of a CYP3A inhibitor such as ketoconazole and a GRM such as mifepristone is believed to be safe for the subject, and to provide the therapeutic benefits of both drugs to the subject, and may allow the reduction in the amount of a GRM, or of a CYP3A inhibitor, administered to the subject; such reduction may reduce the risk of toxic effects of the CYP3A inhibitor concomitantly administered with the GRM. In embodiments, the CYP3A inhibitor is a strong CYP3A inhibitor. Such concomitant administration of a CYP3A inhibitor such as ketoconazole and a GRM such as mifepristone is believed to be safe for the subject, and to provide the therapeutic benefits of both drugs to the subject, may allow the reduction in the amount of GRM administered to the subject, and may allow the reduction in the amount of a CYP3A inhibitor administered to the subject; such reductions may improve treatment of the patient and may reduce the risk of toxic effects of the CYP3A inhibitor.

Applicant discloses herein that steroidogenesis inhibitors may be concomitantly administered with glucocorticoid receptor modulators (GRMs) such as the GR antagonist (GRA) mifepristone. Such concomitant administration of a steroidogenesis inhibitor and a GRM such as mifepristone is believed to be safe for the subject, and to provide the therapeutic benefits of both drugs to the subject, and may allow concomitant administration of a GRA and a steroidogenesis inhibitor, may allow the reduction of the amount of GRM administered to the subject, or may allow the reduction in the amount of a steroidogenesis inhibitor administered to the subject; such reductions may reduce the risk of toxic effects of the steroidogenesis inhibitor. Such concomitant administration of a steroidogenesis inhibitor and a GRM such as mifepristone is believed to be safe for the subject, and to provide the therapeutic benefits of both drugs to the subject, and may allow the reduction in the amount of GRM or of a steroidogenesis inhibitor administered to the subject; such reduction may improve treatment of the subject and may reduce the risk of toxic effects of the steroidogenesis inhibitor.

For example, Applicant has surprisingly discovered that mifepristone may be administered to patients concomitantly receiving ketoconazole. For example ketoconazole may be administered to patients previously, or concomitantly, also receiving mifepristone so that the patient concomitantly receives ketoconazole and mifepristone. Such concomitant administration of ketoconazole and mifepristone is typically safe for the patient, provides the therapeutic benefits of both drugs to the patient, and may allow the reduction in the amount of mifepristone administered to the subject; such reduction may provide an effective dose of mifepristone that is a lower dose, yet still provides similar plasma mifepristone levels as, and may be as effective as, the dose of mifepristone administered in the absence of ketoconazole. Such concomitant administration of ketoconazole and mifepristone provides the therapeutic benefits of both drugs to the patient, may allow a reduction in the amount of mifepristone administered to the patient, and may allow the reduction in the amount of ketoconazole administered to the patient; such reduction may reduce the risk of toxic effects of ketoconazole, and may improve the treatment of the patient.

Applicant's surprising discovery is believed to apply to patients suffering from a disease or disorder and receiving a CYP3A inhibitor, including a strong CYP3A inhibitor such as ketoconazole; such patients suffering from a disease or disorder may be safely administered a GRM, such as mifepristone, concomitantly with the administration of a CYP3A inhibitor such as ketoconazole. Such concomitant administration is believed to be safe for the patient. For example, concomitant administration of ketoconazole and mifepristone surprisingly does not increase the risk of ketoconazole toxicity in the patient, and is believed to be safe for the patient. In particular, Applicant discloses herein that Cushing's syndrome patients receiving ketoconazole may be safely administered mifepristone concomitantly with the administration of ketoconazole. Such concomitant administration of ketoconazole and mifepristone to a patient suffering from Cushing's syndrome is believed to be safe for the patient suffering from Cushing's syndrome, which is characterized by hypercortisolism. Patients suffering from Cushing's syndrome, such as those suffering from endogenous Cushing's syndrome, may suffer hyperglycemia secondary to hypercortisolism. Concomitant administration of a GRA (such as, e.g., mifepristone) and a CYP3A inhibitor (such as, e.g., ketoconazole) as disclosed herein is believed to be safe, and to be suitable for controlling hyperglycemia secondary to hypercortisolism in a patient with endogenous Cushing's syndrome.

In embodiments, a method of treating a patient with Cushing's syndrome, the patient currently taking a GRA at an original dosage, comprises reducing the amount of GRA from said original dosage to an adjusted dosage that is less than the original dosage when the patient is receiving concomitant administration of a CYP3A inhibitor. In embodiments, a method of controlling hyperglycemia secondary to hypercortisolism in a patient with endogenous Cushing's syndrome, the patient currently taking a GRA at an original dosage, comprises reducing the amount of GRA from said original dosage to an adjusted dosage that is less than the original dosage when the patient is receiving concomitant administration of a CYP3A inhibitor. In embodiments of such methods, the adjusted dosage is less than the original dosage by at least an amount selected from about 5%, 10%, 15%, 20%, 25%, 30%, $33^{1/3}$%, 35%, 40%, 45%, 50%, 55%, 60%, 65%, $66^{2/3}$%, 70%, 75%, 80%, 85%, and 90% of the original dosage. In embodiments, the adjusted dosage is less than the original dosage by at least 10% of the original dosage. In embodiments, the adjusted dosage is less than the original dosage by at least 25% of the original dosage. In embodiments, the adjusted dosage is less than the original dosage by at least $33^{1/3}$% of the original dosage. In embodiments, the adjusted dosage is less than the original dosage by at least 50% of the original dosage.

In embodiments, where a GRM such as mifepristone would be prescribed at a first GRM dose, the amount of the GRM (such as mifepristone) administered, when co-administered with a steroidogenesis inhibitor or CYP3A inhibitor such as ketoconazole, may be reduced to a reduced GRM dose that has a smaller amount of GRM as compared to the first GRM dose yet provide effective treatment at the reduced GRM dose co-administered with a steroidogenesis inhibitor such as ketoconazole. In embodiments, the clinical status of a subject receiving a reduced GRM dose concomitantly with a steroidogenesis inhibitor may be monitored for clinical response, e.g., for clinical response to the GRM (such as mifepristone). Monitoring for clinical response may include monitoring for clinical effect of the GRM, including clinical efficacy of the GRM; for clinical effect of a steroidogenesis inhibitor of CYP3A inhibitor; for possible adverse reaction to a steroidogenesis inhibitor or CYP3A inhibitor, or the use of a steroidogenesis inhibitor or CYP3A inhibitor in combination with the GRM; for possible side-effects of a steroidogenesis inhibitor or CYP3A inhibitor; for possible side-effects of the use of a steroidogenesis inhibitor or CYP3A inhibitor in combination with the GRM; or combinations thereof.

In embodiments, the reduced GRM dose may be increased as necessary and as safe for the patient according to such monitoring of the patient. In embodiments, the reduced GRM dose may be titrated upwards as necessary and as safe for the subject according to such monitoring of the patient in order to achieve effective treatment of Cushing's syndrome while remaining safe for the patient with regard to possible adverse effects of the concomitant administration of the GRM and the CYP3A inhibitor, or of the concomitant administration of the GRM and the steroidogenesis inhibitor.

In embodiments, where a GRM such as mifepristone would be prescribed at a first GRM dose, the amount of the GRM (such as mifepristone) administered, when co-administered with a CYP3A inhibitor, including a strong CYP3A inhibitor such as ketoconazole, may be reduced to a reduced GRM dose that has a smaller amount of GRM as compared to the first GRM dose yet provide effective treatment at the reduced GRM dose co-administered with a CYP3A inhibitor such as ketoconazole. In embodiments, the clinical status of a patient receiving a reduced GRM dose concomitantly with a CYP3A inhibitor may be monitored, e.g., for clinical effect of the GRM, for clinical effect of the CYP3A inhibitor, for possible adverse reaction to the CYP3A inhibitor or its use in combination with the GRM, for possible side-effects of the CYP3A inhibitor or its use in combination with the GRM, or combinations thereof. In embodiments, the reduced GRM dose may be increased as necessary and as safe for the patient according to such monitoring of the patient. In embodiments, the reduced GRM dose may be titrated upwards as necessary and as safe for the patient according to such monitoring of the patient in order to achieve effective treatment of Cushing's syndrome while remaining safe for the patient with regard to possible adverse effects of the concomitant administration of the GRM and the CYP3A inhibitor.

Accordingly, Applicant discloses herein that a steroidogenesis inhibitor may be administered to patients concomitantly receiving administration of a GRM. Accordingly, Applicant discloses herein that a CYP3A inhibitor may be administered to patients concomitantly receiving administration of a GRM. For example, Applicant discloses herein that ketoconazole, a steroidogenesis inhibitor and a CYP3A inhibitor, may be administered to patients suffering from a disease or disorder, such as, e.g., Cushing's syndrome, who are concomitantly receiving administration of a GRM such as mifepristone. Such concomitant administration of both a GRA (such as mifepristone) and a CYP3A inhibitor (such as ketoconazole) may be administered to a patient suffering from endogenous Cushing's syndrome to control hyperglycemia secondary to hypercortisolism in the patient.

Accordingly, Applicant discloses herein that GRMs may be administered to subjects previously, or concomitantly, also receiving administration of a steroidogenesis inhibitor or a CYP3A inhibitor. For example, Applicant discloses herein that GRMs may be administered to subjects suffering from a disease or disorder, such as, e.g., Cushing's syndrome, who previously, or are concomitantly, also receiving administration of a steroidogenesis inhibitor such as ketoconazole or a CYP3A inhibitor such as ketoconazole or itraconazole. Applicant discloses methods for concomitant administration of a GRM and a steroidogenesis or CYP3A inhibitor such as ketoconazole useful for treating a subject in need of such administration. Subjects in need of such administration include subjects suffering from a disease or disorder, and include subjects suffering from Cushing's syndrome. Applicant further discloses that such administration of a GRM and a steroidogenesis inhibitor such as ketoconazole or a CYP3A inhibitor such as ketoconazole or itraconazole is typically safe for the subject, and provides the therapeutic benefits of both drugs to the subject. In embodiments, such concomitant administration of an inhibitor such as ketoconazole or itraconazole and a GRM may allow the reduction in the amount of GRM, or of a steroidogenesis or a CYP3A inhibitor such as ketoconazole, that is administered to the subject; such reductions may reduce the risk of toxic effects of a steroidogenesis inhibitor such as ketoconazole, or a CYP3A inhibitor such as ketoconazole or itraconazole, such as, e.g., reduce the risk of liver damage to the subject. The GRM may be, e.g., mifepristone.

Applicant has surprisingly discovered that a steroidogenesis or a CYP3A inhibitor such as ketoconazole may be concomitantly administered with GRMs, such as GRAs, so that concomitant administration of a steroidogenesis or a CYP3A inhibitor such as ketoconazole and a GRA for example may provide safe and effective treatment of a patient in need of treatment. A patient receiving concomitant administration of a steroidogenesis inhibitor such as ketoconazole or a CYP3A inhibitor such as ketoconazole or itraconazole and a GRA may be, for example, a patient in need of treatment for Cushing's syndrome (including Cushing's Disease), breast cancer, prostate cancer, ovarian cancer, or other hormone-sensitive cancer. In embodiments, such a patient in need of treatment may receive concomitant administration of a steroidogenesis inhibitor such as ketoconazole or a CYP3A inhibitor such as ketoconazole or itraconazole and a GRA, such as mifepristone. In embodiments, such a patient in need of treatment may receive concomitant administration of ketoconazole and mifepristone.

The methods, compositions, and kits disclosed herein are suitable for use in treating patients suffering from Cushing's syndrome (including Cushing's Disease); or from prostate cancer and other androgen-sensitive cancers; or from breast cancer, ovarian cancer, or other hormone-sensitive cancer (e.g., cancer sensitive to estrogen or progesterone); and are suitable for use in treating subjects suffering from other diseases, disorders, or syndromes.

In embodiments of the methods disclosed herein, a patient currently receiving a GRM, such as mifepristone, is also concomitantly administered a steroidogenesis inhibitor or a CYP3A inhibitor such as ketoconazole or itraconazole. In embodiments of the methods disclosed herein, a patient currently receiving a GRM, such as mifepristone, as treatment for a condition characterized by excess steroid levels, or as treatment of a condition that is treated by reducing steroid levels or by reducing steroid effects, is also concomitantly administered a steroidogenesis inhibitor or a CYP3A inhibitor such as ketoconazole or itraconazole, whereby the patient is treated for that condition. In embodiments, the condition is characterized by excessive cortisol levels. In embodiments, the condition is hyperglycemia secondary to hypercortisolism, e.g., in a patient suffering from endogenous Cushing's syndrome. In embodiments, the condition is cancer, and may be a hormone-sensitive cancer. In embodiments, the hormone sensitive cancer is prostate cancer, breast cancer, or ovarian cancer.

In embodiments of the methods disclosed herein, a patient currently receiving a steroidogenesis or a CYP3A inhibitor such as ketoconazole or itraconazole is also concomitantly administered a GRM. In embodiments of the methods disclosed herein, a patient currently receiving a steroidogenesis or a CYP3A inhibitor such as ketoconazole or itraconazole as treatment for a condition characterized by excess steroid levels, or as treatment of a condition that is treated by reducing steroid levels or by reducing steroid effects, is also concomitantly administered a GRM, whereby the patient is treated for that condition. In embodiments, the condition is characterized by excessive cortisol levels. In embodiments, the condition is hyperglycemia secondary to hypercortisolism, e.g., in a patient suffering from endogenous Cushing's syndrome. In embodiments, the condition is hyperglycemia secondary to hypercortisolism, e.g., in a patient suffering from endogenous Cushing's syndrome. In embodiments, the condition is cancer, and may be a hormone-sensitive cancer. In embodiments, the hormone sensitive cancer is prostate cancer, breast cancer, or ovarian cancer.

Thus, in embodiments of the methods disclosed herein, a patient in need of treatment for a condition is concomitantly administered both a GRM (such as mifepristone) and a steroidogenesis or a CYP3A inhibitor (such as ketoconazole or itraconazole), whereby the patient is treated for that condition. In embodiments, the condition is characterized by excessive cortisol levels. In embodiments, the condition is hyperglycemia secondary to hypercortisolism, e.g., in a patient suffering from endogenous Cushing's syndrome. In embodiments, the condition is cancer, and may be a hormone-sensitive cancer. In embodiments, the hormone sensitive cancer is prostate cancer, breast cancer, or ovarian cancer.

In embodiments, the amount of GRM administered concomitantly with a steroidogenesis or a CYP3A inhibitor is the same amount, or substantially the same amount, of GRM previously administered to the patient prior to concomitant administration of a GRM and a steroidogenesis or a CYP3A inhibitor. In embodiments, the amount of GRM administered concomitantly with a steroidogenesis or a CYP3A inhibitor is less than the amount of GRM previously administered to the subject prior to concomitant administration of a GRM and a steroidogenesis or a CYP3A inhibitor. In embodiments, administration of a reduced amount of GRM administered concomitantly with a steroidogenesis or a CYP3A inhibitor is an effective amount of GRM; in embodiments, the reduced amount of GRM administered concomitantly with a steroidogenesis or a CYP3A inhibitor is as effective as the amount of GRM previously administered to the subject prior to concomitant administration of a GRM and a steroidogenesis or a CYP3A inhibitor. The GRM may be mifepristone. The steroidogenesis or a CYP3A inhibitor may be ketoconazole.

In embodiments, the amount of steroidogenesis or a CYP3A inhibitor administered concomitantly with the GRM is the same amount, or substantially the same amount, of steroidogenesis or CYP3A inhibitor previously administered to the subject prior to concomitant administration of a GRM and a steroidogenesis or a CYP3A inhibitor. In embodiments, the amount of steroidogenesis or CYP3A inhibitor administered concomitantly with the GRM is less than the amount of steroidogenesis or CYP3A inhibitor previously administered to the subject prior to concomitant administration of a GRM and a steroidogenesis or a CYP3A inhibitor. In embodiments, administration of a reduced amount of steroidogenesis or CYP3A inhibitor administered concomitantly with a GRM is an effective amount of steroidogenesis or CYP3A inhibitor; in embodiments, the reduced amount of steroidogenesis or CYP3A inhibitor administered concomitantly with a GRM is as effective as the amount of steroidogenesis or CYP3A inhibitor previously administered to the subject prior to concomitant administration of a GRM and a steroidogenesis or a CYP3A inhibitor. The GRM may be mifepristone. The steroidogenesis or CYP3A inhibitor may be ketoconazole.

Concomitant administration of a GRM and steroidogenesis or a CYP3A inhibitor may be administration of a GRM followed within a short time by administration of a steroidogenesis or a CYP3A inhibitor. In embodiments, concomitant administration of a GRM and a steroidogenesis or a CYP3A inhibitor may be administration of mifepristone followed within a short time by administration of ketoconazole. Concomitant administration of a GRM and a steroidogenesis or a CYP3A inhibitor may be administration of a steroidogenesis or a CYP3A inhibitor followed within a short time by administration of a GRM. In embodiments, concomitant administration of a GRM and a steroidogenesis or a CYP3A inhibitor may be administration of ketoconazole followed within a short time by administration of mifepristone. Concomitant administration of a GRM and a steroidogenesis or a CYP3A inhibitor may be simultaneous administration of a GRM and a steroidogenesis or a CYP3A inhibitor. In embodiments, concomitant administration of a GRM and a steroidogenesis or a CYP3A inhibitor may be simultaneous administration of mifepristone and ketoconazole.

In embodiments, the GRM is a steroidal GRM, such as, e.g., mifepristone. In embodiments, the GRM is a non-steroidal GRM. In embodiments, the GRM is a glucocorticoid receptor antagonist (GRA). In embodiments, the GRA is a steroidal GRA. In embodiments, the GRA is mifepristone. In embodiments, the GRA is a non-steroidal GRA. In embodiments, the GRA is a non-steroidal GRA selected from a GRA having a cyclohexyl-pyrimidine backbone, GRA having a fused azadecalin backbone, a GRA having a heteroaryl ketone fused azadecalin backbone, and a GRA having an octahydro fused azadecalin backbone.

In embodiments, a patient is concomitantly administered a GRM and ketoconazole; in embodiments, the GRM is mifepristone. In embodiments, concomitant administration comprises simultaneous administration of a GRM and ketoconazole to a patient, where the GRM is mifepristone. In embodiments, the amount of ketoconazole administered concomitantly with the mifepristone is the same amount, or substantially the same amount, of ketoconazole previously administered to the subject prior to concomitant administration of mifepristone and ketoconazole. In embodiments, the amount of ketoconazole administered concomitantly with the mifepristone is less than the amount of ketoconazole previously administered to the subject prior to concomitant administration of mifepristone and ketoconazole.

Accordingly, in embodiments, Applicant discloses herein a method for treating a patient who is suffering from Cushing's syndrome or a condition associated with Cushing's syndrome, said patient receiving a first dose of a GRM, such as a glucocorticoid receptor antagonist (GRA), said method comprising: concomitantly administering to the patient a dose of a CYP3A inhibitor and a reduced dose of said GRM, wherein said reduced GRM dose consists of a GRM dose that is less than the first GRM dose, whereby the patient is treated for Cushing's syndrome or a condition associated with Cushing's syndrome by concomitant administration of said CYP3A inhibitor and a reduced dose said GRM. Conditions associated with Cushing's syndrome include, without limitation, hyperglycemia secondary to hypercortisolism, e.g., hyperglycemia secondary to hypercortisolism in a patient suffering from endogenous Cushing's syndrome. Conditions associated with Cushing's syndrome also include, without limitation, hyperglycemia secondary to hypercortisolism in an adult Cushing's syndrome patient who has type 2 diabetes mellitus or glucose intolerance. Conditions associated with Cushing's syndrome further include, without limitation, hyperglycemia secondary to hypercortisolism in an adult Cushing's syndrome patient who has a) type 2 diabetes mellitus or glucose intolerance, and b) has failed surgery or is not a candidate for surgery.

In embodiments, the dosage of said reduced GRM dose is less than the dosage of said first GRA dose by at least an amount selected from about 5%, 10%, 15%, 20%, 25%, 30%, $33^{1/3}$% 35%, 40%, 45%, 50%, 55%, 60%, 65% $66^{2/3}$% 70%, 75%, 80%, 85%, and 90% of the first GRM dose. In embodiments, the dosage of said reduced GRM dose is less than the dosage of said first GRM dose by about 300 milligrams (mg) of said GRM. In embodiments, the dosage amount of said first GRM dose is 600 mg or higher of said GRM. In embodiments, said reduced GRM dose is a GRM dose selected from the group of GRM doses consisting of about 1500 milligrams (mg) GRM, about 1200 mg GRA, about 900 mg GRM, and about 600 mg GRM. In embodiments, said reduced GRM dose is 900 mg of the GRM. In embodiments, said reduced GRM dose is 600 mg of the GRM. In embodiments, the reduced GRM dose is a daily GRM dose. In embodiments, the methods further comprise titrating upwards the dosage of the reduced GRM dose. In embodiments, such titrating upwards comprises increasing the dosage of the reduced GRM dose in increments of 300 milligrams (mg) of GRM. In embodiments, the interval of time between upward titration of a reduced dose, or of an upwardly titrated reduced dose, and a subsequent upward titration of a dosage of the reduced dose of mifepristone is selected from one week, two weeks, three weeks, and four weeks. In embodiments, the methods include monitoring the patient for clinical response to the GRM. In embodiments, such titrating upwards follows a determination that said reduced GRM dose is associated with a decrease in clinical response to the GRM. In embodiments, monitoring the patient for clinical response to the GRM comprises monitoring the patient for glucose control, anti-diabetic medication requirement, insulin level, psychiatric symptoms, cushingoid appearance, acne, hirsutism, body weight, or combinations thereof. In embodiments, such titrating upwards is capped at a dosage level of 900 milligrams per day. In embodiments, such titrating upwards is capped at a dosage level of 600 milligrams per day. In embodiments of the methods disclosed herein, the reduced GRM dose is a daily dose of 900 mg mifepristone. In embodiments of the methods disclosed herein, the reduced GRM dose is a daily dose of 600 mg mifepristone.

Embodiments of the methods disclosed herein are directed to treating a patient suffering from Cushing's syndrome or a condition associated with Cushing's syndrome. In embodiments, the patient suffering from Cushing's syndrome or a condition associated with Cushing's syndrome is a patient suffering from a condition associated with endogenous Cushing's syndrome. In embodiments, treating a patient who is suffering from Cushing's syndrome or a condition associated with Cushing's syndrome comprises treating a patient who is suffering from hyperglycemia secondary to hypercortisolism. In embodiments, treating patient who is suffering from Cushing's syndrome or a condition associated with Cushing's syndrome comprises treating hyperglycemia secondary to hypercortisolism in a Cushing's syndrome patient having type 2 diabetes mellitus or glucose intolerance. In embodiments, treating a patient who is suffering from Cushing's syndrome or a condition associated with Cushing's syndrome comprises treating hyperglycemia secondary to hypercortisolism in a Cushing's syndrome patient, said patient a) having type 2 diabetes mellitus or glucose intolerance, and b) having failed surgery or is not a candidate for surgery. In embodiments, treating a patient who is suffering from Cushing's syndrome or a condition associated with Cushing's syndrome comprises administering mifepristone to control hyperglycemia secondary to hypercortisolism in an adult Cushing's syndrome patient who has a) type 2 diabetes mellitus or glucose intolerance, and b) has failed surgery or is not a candidate for surgery.

In embodiments, Applicant discloses herein a method for treating a patient who is suffering from Cushing's syndrome or a condition associated with Cushing's syndrome, said patient receiving a first dose of a glucocorticoid receptor modulator (GRM), such as a glucocorticoid receptor antagonist (GRA), said method comprising: concomitantly administering to the patient a dose of said CYP3A inhibitor and a first dose of a glucocorticoid receptor modulator (GRM), whereby the patient is treated for Cushing's syndrome or a condition associated with Cushing's syndrome by concomitant administration of said CYP3A inhibitor and said GRM. In embodiments, the first GRM dose is selected from a GRM dose no greater than 900 milligrams (mg) per day of the GRM, and no greater than 600 mg per day of the GRM. In embodiments, the patient had been administered a dose of the CYP3A inhibitor prior to said administering of said first GRM dose. In embodiments, said concomitant administration of the CYP3A inhibitor and said GRM comprises administration of said first GRM dose to a patient having detectable levels of said CYP3A inhibitor, wherein said patient had been administered a dose of the CYP3A inhibitor prior to said administration of said first GRM dose. In embodiments, methods further comprise titrating upwards the dosage of a subsequent GRM dose, wherein the dosage of said subsequent GRM dose is a greater amount of GRM than the amount of GRM of the first GRM dose. In embodiments, such titrating upwards comprises increasing the dosage of the subsequent GRM dose in increments of 300 milligrams (mg) of GRM. In embodiments, the interval of time between upward titration of a subsequent GRM dose, or of an upwardly titrated subsequent GRM dose, and a subsequent upward titration of the dosage of the subsequent GRM dose is selected from one week, two weeks, three weeks, and four weeks.

In embodiments, Applicant discloses herein the use of a glucocorticoid receptor modulator (GRM) when the patient is receiving concomitant administration of a CYP3A inhibitor to treat a patient who is suffering from Cushing's syndrome or a condition associated with Cushing's syndrome. In embodiments, Applicant discloses herein the use of a GRM when the patient is receiving concomitant administration of a CYP3A inhibitor to control hyperglycemia secondary to hypercortisolism in a patient with endogenous Cushing's syndrome. In embodiments of such uses, the GRM is mifepristone. In embodiments of such uses, the CYP3A inhibitor is ketoconazole or itraconazole. In embodiments of such uses, the use comprises a once-daily dose of said GRM. In embodiments of such uses, the once-daily dose of said GRM is titrated up to greater than 800 mg per day from 300 mg per day or 600 mg per day of GRM.

In embodiments of the methods and uses disclosed herein, the CYP3A inhibitor is a strong CYP3A inhibitor selected from the group consisting of ketoconazole, itraconazole, nefazodone, ritonavir, nelfinavir, indinavir, atazanavir, amprenavir and fosamprenavir, clarithromycin, conivaptan, lopinavir/ritonavir, posaconazole, saquinavir, telithromycin, and voriconazole. In embodiments, the CYP3A inhibitor is ketoconazole or itraconazole.

In embodiments of the methods and uses disclosed herein, the GRM is mifepristone.

The methods and uses disclosed herein provide advantages including expanded treatment options for patients suffering from conditions including Cushing's syndrome, Cushing's Disease, prostate cancer, breast cancer, ovarian cancer, and other conditions.

The methods and uses disclosed herein provide advantages including improved treatments for patients suffering from conditions including Cushing's syndrome, Cushing's Disease, prostate cancer, breast cancer, ovarian cancer, and other conditions, where such improved treatments may include the ability to alter the amount of a GRM, such mifepristone, administered to the patient by administering a GRM such as mifepristone concomitantly with ketoconazole. In embodiments, such improved treatments include the ability to reduce the amount of a GRM, such as mifepristone, administered to a subject.

The methods and uses disclosed herein provide advantages including improved treatments for patients suffering from conditions including Cushing's syndrome, Cushing's Disease, prostate cancer, breast cancer, ovarian cancer, and other conditions, where such improved treatments may include the ability to alter the amount of a CYP3A inhibitor such as ketoconazole or itraconazole administered to the patient by administering a GRM such as mifepristone concomitantly with the CYP3A inhibitor. In embodiments, such improved treatments include the ability to reduce the amount of the CYP3A inhibitor administered to a subject and thus to reduce risk of toxic effects of a CYP3A inhibitor, such as, e.g., ketoconazole or itraconazole.

DETAILED DESCRIPTION

Figure 1:
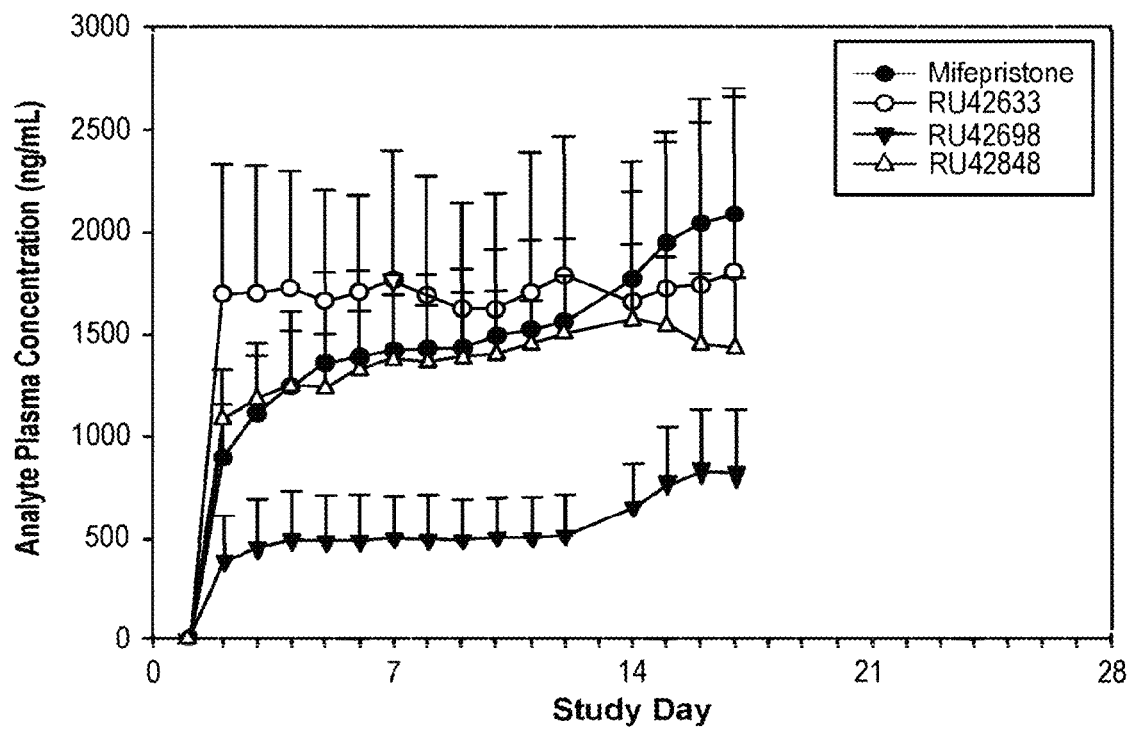
FIG. 1 shows the mean and standard deviation of mifepristone and its metabolites RU42633, RU42698, and RU42848 measured in healthy male volunteers prior to administration of mifepristone on days one through seventeen. Ketoconazole was also administered on days thirteen-seventeen.

Ketoconazole strongly inhibits corticosteroid synthesis; thus, ketoconazole strongly reduces cortisol levels in subjects administered ketoconazole. However, there is concern over its use, for example, due to potential hepatoxicity (see, e.g., Castinetti et al., J Clin Endocrinol Metab 99(5):1623-1630 (2014)).

According to the U.S. Food and Drug Administration (FDA) definition (http://www.fda.gov/Drugs/DevelopmentApprovalProcess/DevelopmentResources/DrugInteractionsLabeling/ucm093664.htm, accessed Feb. 16, 2017), strong CYP3A inhibitors are expected to increase the AUC of other drugs by greater than five-fold. Ketoconazole is identified by the FDA as a strong CYP3A inhibitor.

Surprisingly, as disclosed herein, concomitant administration of mifepristone and ketoconazole causes only a small increase in the plasma levels of mifepristone, and does not cause the large increases that would have been expected for such concomitant administration.

Applicant has surprisingly found that concomitant administration of mifepristone and ketoconazole causes only a small increase in the AUC and in the $C_{max}$ of mifepristone in subjects receiving mifepristone alone for twelve days, and then administered both mifepristone and ketoconazole concomitantly. The $C_{max}$ of mifepristone administered concomitantly with ketoconazole is increased by less than two-fold (a mere 28% increase in mifepristone $C_{max}$) and the AUC of mifepristone administered concomitantly with ketoconazole is increased by less than two-fold (a mere 38% increase in mifepristone AUC) in subjects receiving 600 mg mifepristone per day who then are given 400 mg ketoconazole (200 mg twice per day)).

Also surprisingly, as disclosed herein, concomitant administration of ketoconazole and mifepristone also caused smaller increases in ketoconazole levels than would be expected. The $C_{max}$ of ketoconazole administered concomitantly with mifepristone is increased by less than four-fold (365% increase in ketoconazole $C_{max}$) and the AUC of ketoconazole administered concomitantly with mifepristone is increased by less than three-fold (253% increase in ketoconazole AUC) when comparing ketoconazole levels on the first day of concomitant administration of both drugs as compared to the ketoconazole levels in subjects on the fifth day of receiving 400 mg ketoconazole (200 mg twice per day) concomitantly with 600 mg mifepristone per day.

Applicant has surprisingly found that concomitant administration of mifepristone and itraconazole causes only a small increase in the AUC and in the $C_{max}$ of mifepristone in subjects receiving mifepristone alone, and then administered both mifepristone and itraconazole concomitantly. Administration of itraconazole (200 mg once per day within 30 minutes after breakfast) with mifepristone (900 mg once per day, within 5 minutes following itraconazole) led to mifepristone levels in subjects comparable to those levels obtained in the subjects when 1200 mg mifepristone was given alone (within 30 minutes after breakfast). The $C_{max}$ of 900 mg mifepristone per day administered concomitantly with 200 mg itraconazole per day is increased by about 20% as compared to the $C_{max}$ of 900 mg mifepristone per day administered without itraconazole; the $AUC_{0-24}$ of 900 mg mifepristone per day administered concomitantly with 200 mg itraconazole per day is increased by about 10% as compared to the $AUC_{0-24}$ of 900 mg mifepristone per day administered without itraconazole.

Ketoconazole is a strong inhibitor of steroidogenesis; thus it is believed that ketoconazole may serve as an exemplar for other strong inhibitors of steroidogenesis and that these results indicate that mifepristone, and other glucocorticoid receptor modulators, including other glucocorticoid receptor antagonists, may be safely administered concomitantly with steroidogenesis inhibitors according to the methods disclosed herein.

Applicant discloses herein methods for the safe concomitant administration of both a glucocorticoid receptor modulator (GRM) and steroidogenesis inhibitor to a subject. Applicant discloses herein the surprising finding that both a GRM such as mifepristone and a steroidogenesis inhibitor such as ketoconazole may be safely administered to a subject at the same, or nearly the same, time (i.e., the GRM and the steroidogenesis inhibitor may be concomitantly administered).

Applicant discloses herein methods for the safe concomitant administration of both a glucocorticoid receptor modulator (GRM) and CYP3A inhibitor to a subject. Applicant discloses herein the surprising finding that both a GRM such as mifepristone and a CYP3A inhibitors such as ketoconazole and itraconazole may be safely administered to a subject at the same, or nearly the same, time (i.e., the GRM and the CYP3A may be concomitantly administered).

Applicant discloses herein surprising results showing the safe concomitant administration of mifepristone, a glucocorticoid receptor modulator, and ketoconazole or itraconazole. Ketoconazole and itraconazole are strong inhibitors of CYP3A enzymes, and may be used to determine the effects of the class of strong CYP3A inhibitors (see FDA "Clinical Drug Interaction Studies—Study Design, Data Analysis, and Clinical Implications Guidance for Industry", pages 10-11 (https://www.fda.gov/downloads/drugs/guidances/ucm292362.pdf). Thus it is believed that ketoconazole and itraconazole may serve as examplars for other strong inhibitors of CYP3A enzymes. The results with mifepristone disclosed herein are believed to indicate that mifepristone and also other glucocorticoid receptor modulators, including other glucocorticoid receptor antagonists, may be safely administered concomitantly with CYP3A enzyme inhibitors according to the methods disclosed herein. Such CYP3A enzyme inhibitors include strong CYP3A inhibitors (such as, e.g., ketoconazole, itraconazole, nefazodone, ritonavir, nelfinavir, indinavir, atazanavir, amprenavir and fosamprenavir, clarithromycin, conivaptan, lopinavir/ritonavir, posaconazole, saquinavir, telithromycin, and voriconazole). Since less strong CYP3A inhibitors would be expected to have smaller effects on plasma levels of mifepristone and its metabolites, these results indicate that mifepristone may also be safely administered with other CYP3A inhibitors in addition to those listed above, including CYP3A inhibitors that are not strong CYP3A inhibitors (such as, e.g., fluconazole, cimetidine, boceprevir, and telaprevir).

Applicant discloses herein the surprising finding that a subject receiving the CYP3A inhibitor ketoconazole or the CYP3A inhibitor itraconazole, may also be safely administered an effective dose of mifepristone, which is a glucocorticoid receptor modulator (GRM), e.g., a glucocorticoid receptor antagonist (GRA). Applicant also discloses herein the surprising finding that a subject receiving mifepristone, which is a GRM, e.g., a GRA, may also be safely administered the CYP3A inhibitor ketoconazole or the CYP3A inhibitor itraconazole. Applicant also discloses herein the surprising finding that a subject receiving mifepristone may also be safely administered a steroidogenesis inhibitor (i.e., ketoconazole); ketoconazole is a steroidogenesis inhibitor in addition to being a CYP3A inhibitor.

In embodiments of the methods disclosed herein, a subject receiving a GRM (such as, e.g., a GRA such as mifepristone) may be safely administered an effective dose of a steroidogenesis inhibitor such as ketoconazole. In embodiments of the methods disclosed herein, a subject may be safely administered ketoconazole and a reduced dose of a GRM, where the reduced dose of a GRM is an effective dose of GRM that is a smaller GRM dose than the GRM dose administered in the absence of a steroidogenesis inhibitor such as ketoconazole. In embodiments of the methods disclosed herein, a subject may be safely administered a GRM and a reduced dose of a steroidogenesis inhibitor such as ketoconazole, where the reduced dose of the steroidogenesis inhibitor is an effective dose of the steroidogenesis inhibitor that is a smaller dose than the a steroidogenesis inhibitor dose administered in the absence of the GRM. In embodiments of the methods disclosed herein, a subject receiving a steroidogenesis inhibitor such as, e.g., ketoconazole, may be safely administered an effective dose of a GRM, such as, e.g., mifepristone. In embodiments of the methods disclosed herein, a subject receiving a GRM, such as, e.g., mifepristone, may be safely administered an effective dose of a steroidogenesis inhibitor such as, e.g., ketoconazole.

These methods may be applied to subjects suffering from diseases or disorders as well as other subjects, including subjects suffering from Cushing's syndrome. Such concomitant administration of a steroidogenesis inhibitor such as ketoconazole with a GRM would have been expected to produce toxic side effects due to, e.g., an adverse effect on steroidogenesis inhibitor metabolism due to the added GRM (e.g., where the steroidogenesis inhibitor is ketoconazole, a previously safe ketoconazole dose would have been expected to be a toxic dose in the presence of added GRM (e.g., mifepristone)).

In particular, Applicant discloses herein that patients suffering from a disease or disorder and receiving ketoconazole or itraconazole may be safely administered mifepristone concomitantly with the administration of ketoconazole or itraconazole. Such concomitant administration of mifepristone with ketoconazole or itraconazole surprisingly does not increase the risk of toxicity in the patient, and is believed to be safe for the patient. In particular, Applicant discloses herein that Cushing's syndrome patients receiving ketoconazole or itraconazole may be safely administered mifepristone concomitantly with the administration of ketoconazole or itraconazole. Such concomitant administration of ketoconazole or itraconazole with mifepristone surprisingly does not increase the risk of toxicity in humans, and is believed to be safe for a patient suffering from Cushing's syndrome.

Thus, Applicant discloses herein surprising and useful methods for concomitant administration of a CYP3A inhibitor such as, e.g., ketoconazole or itraconazole, and a GRM such as, e.g., mifepristone, which provide the benefits of improved treatment without substantially increased risk of adverse treatment side-effects. For example, Applicant provides herein surprising and useful methods for concomitant administration of ketoconazole or itraconazole with mifepristone, which provide the benefits of both drugs without substantially increased risk of ketoconazole or itraconazole toxicity, which can have serious adverse effects on the liver.

Thus, Applicant discloses herein surprising and useful methods for concomitant administration of a steroidogenesis inhibitor such as, e.g., ketoconazole, and a GRM such as, e.g., mifepristone, which provide the benefits of improved treatment without substantially increased risk of adverse treatment side-effects. For example, Applicant provides herein surprising and useful methods for concomitant administration of ketoconazole and mifepristone, which provide the benefits of both drugs without substantially increased risk of ketoconazole toxicity, which can have serious adverse effects on the liver.

Thus, contrary to the expectation that the presence of a GRM such as mifepristone along with a steroidogenesis inhibitor (e.g., ketoconazole) in a patient would increase the toxicity of the steroidogenesis inhibitor beyond that expected for such a dose of steroidogenesis inhibitor alone, Applicant has discovered that administering a) both a GRM (e.g., mifepristone) and a steroidogenesis inhibitor (e.g., ketoconazole) to a subject, or b) administering a GRM (e.g., mifepristone) to a subject who has recently been given a steroidogenesis inhibitor (e.g., ketoconazole), or c) administering a steroidogenesis inhibitor (e.g., ketoconazole) soon after GRM (e.g., mifepristone) administration to a subject, concomitant administration of a GRM and a steroidogenesis inhibitor does not increase the expected toxicity of the steroidogenesis inhibitor. In embodiments, concomitant administration of a steroidogenesis inhibitor and a GRM allows for administration of an effective dose of GRM that is a reduced GRM dose as compared to the GRM dose administered in the absence of the steroidogenesis inhibitor.

In embodiments, concomitant administration of ketoconazole and mifepristone allows for administration of an effective dose of mifepristone that is a reduced dose of mifepristone as compared to the mifepristone dose administered in the absence of ketoconazole. For example, Applicant has discovered that concomitant administration of mifepristone and ketoconazole makes it possible to reduce the dose of mifepristone while maintaining sufficient mifepristone levels for effective therapy for the patient. Such a reduction in mifepristone dose provides the benefit of reducing the amount of mifepristone administered to the subject. Embodiments in which a subject is concomitantly administered ketoconazole and mifepristone allow for mifepristone dose reduction (as compared to the mifepristone dose in the absence of ketoconazole) include, e.g., Cushing's syndrome and hormone-sensitive cancers such as breast, ovarian, and prostate cancer, and other disorders susceptible of treatment by mifepristone.

In embodiments, the reduced dose of mifepristone administered to a subject also concomitantly receiving ketoconazole is a dose of mifepristone that is at least about 5% less than the original dose of mifepristone, where the original dose of mifepristone is the dose the subject had been, or would have been, administered in the absence of ketoconazole co-administration. In embodiments, the reduced dose of mifepristone is a dose of mifepristone that is at least about 10% less than the original dose of mifepristone; and may be a dose of mifepristone that is at least about 15%, or about 20%, or about 22%, or about 23%, or about 25%, or about 28%, or about 29%, or about 33%, or about 38%, or about 40%, or about 50%, or about 66%, or about 75% less than the original dose of mifepristone.

In embodiments, the reduced dose of mifepristone administered to a subject also concomitantly receiving ketoconazole is a dose of mifepristone that is 300 mg less mifepristone than the amount of the original dose of mifepristone. In embodiments, the reduced dose of mifepristone administered to a subject also concomitantly receiving ketoconazole is a dose of mifepristone that is an amount of mifepristone that is an integer multiple of 300 mg mifepristone less than the amount of the original dose of mifepristone. In embodiments, the integer of the integer multiple is selected from the integers 1, 2, 3, 4, and 5.

In embodiments, the reduced dose of mifepristone administered to a subject also concomitantly receiving ketoconazole is a dose of mifepristone that is about 900 mg mifepristone; or is about 600 mg mifepristone; or is about 300 mg mifepristone. In embodiments, the reduced dose of mifepristone administered to a subject also concomitantly receiving ketoconazole is a dose of mifepristone that is about 300 mg mifepristone administered only every other day; or is about 300 mg mifepristone administered every third day; or is about 300 mg mifepristone administered every fourth day. For example, where the original dose of mifepristone is about 1500 mg per day, the reduced dose of mifepristone may be about 1200 mg of mifepristone administered every day; or may be about 900 mg of mifepristone administered every day; or may be about 600 mg of mifepristone administered every day; or may be about 300 mg of mifepristone administered every day. For example, where the original dose of mifepristone is about 1200 mg per day, the reduced dose of mifepristone may be about 900 mg of mifepristone administered every day; or may be about 600 mg of mifepristone administered every day; or may be about 300 mg of mifepristone administered every day. For example, where the original dose of mifepristone is about 900 mg per day, the reduced dose of mifepristone may be about 600 mg of mifepristone administered every day; or may be about 300 mg of mifepristone administered every day; or may be about 300 mg of mifepristone administered every other day. For example, where the original dose of mifepristone is about 600 mg per day, the reduced dose of mifepristone may be about 300 mg of mifepristone administered every day; or may be about 300 mg of mifepristone administered every other day; or may be about 300 mg of mifepristone administered every third day. For example, where the original dose of mifepristone is about 300 mg per day, the reduced dose of mifepristone may be about 300 mg of mifepristone administered every other day; or may be about 300 mg of mifepristone administered every third day; or may be about 300 mg of mifepristone administered every fourth day.

In embodiments in which a subject has been receiving about 1800 mg mifepristone per day, and concomitant administration of mifepristone and a CYP3A inhibitor such as, e.g., ketoconazole or itraconazole, is indicated, the reduced dose of mifepristone may be about 1500 mg mifepristone per day; may be about 1200 mg mifepristone per day; may be about 900 mg mifepristone per day; may be greater than 800 mg/day; may be about 600 mg mifepristone per day; may be about 300 mg mifepristone per day; may be about 300 mg mifepristone every other day; or may be about 300 mg mifepristone every third day. In embodiments in which a subject has been receiving about 1500 mg mifepristone per day, and concomitant administration of mifepristone and a CYP3A inhibitor such as, e.g., ketoconazole or itraconazole, is indicated, the reduced dose of mifepristone may be about 1200 mg mifepristone per day; may be about 900 mg mifepristone per day; may be greater than 800 mg/day; may be about 600 mg mifepristone per day; may be about 300 mg mifepristone per day; may be about 300 mg mifepristone every other day; or may be about 300 mg mifepristone every third day. In embodiments in which a subject has been receiving about 1200 mg mifepristone per day, and concomitant administration of mifepristone and a CYP3A inhibitor such as, e.g., ketoconazole or itraconazole, is indicated, the reduced dose of mifepristone may be about 900 mg mifepristone per day; may be greater than 800 mg/day; may be about 600 mg mifepristone per day; may be about 300 mg mifepristone per day; may be about 300 mg mifepristone every other day; or may be about 300 mg mifepristone every third day. In embodiments in which a subject has been receiving about 900 mg mifepristone per day, and concomitant administration of mifepristone and a CYP3A inhibitor such as, e.g., ketoconazole or itraconazole, is indicated, the reduced dose of mifepristone may be greater than 800 mg/day; may be about 600 mg mifepristone per day; may be about 300 mg mifepristone per day; may be about 300 mg mifepristone every other day; or may be about 300 mg mifepristone every third day. In embodiments in which a subject has been receiving about 600 mg mifepristone per day, and concomitant administration of mifepristone and a CYP3A inhibitor such as, e.g., ketoconazole or itraconazole, is indicated, the reduced dose of mifepristone may be about 300 mg mifepristone per day; may be about 300 mg mifepristone every other day; may be about 300 mg every third day; or may be about 300 mg mifepristone every fourth day. In embodiments in which a subject has been receiving about 300 mg mifepristone per day, and concomitant administration of mifepristone and a CYP3A inhibitor such as, e.g., ketoconazole or itraconazole, is indicated, the reduced dose of mifepristone may be about 300 mg mifepristone every other day; may be about 300 mg every third day; or may be about 300 mg mifepristone every fourth day.

In embodiments in which a subject has been receiving a first dose of mifepristone (e.g. a daily dose of mifepristone of about 1800 mg/day, or about 1500 mg/day, or about 1200 mg/day, or about 900 mg/day, or greater than 800 mg/day, or about 600 mg/day, or about 300 mg/day), and concomitant administration of mifepristone and a CYP3A inhibitor such as, e.g., ketoconazole or itraconazole, is indicated, the subject may be administered a reduced dose of mifepristone, where the amount of the reduced dose is less than the original mifepristone dose by about 300 mg mifepristone per day, and the subject may be monitored for clinical effects of the drugs, including monitoring for clinical response to mifepristone. In embodiments in which a subject has been receiving a first dose of mifepristone (e.g. a daily dose of mifepristone of about 1800 mg/day, or about 1500 mg/day, or about 1200 mg/day, or about 900 mg/day, or greater than 800 mg/day, or about 600 mg/day, or about 300 mg/day), and concomitant administration of mifepristone and a CYP3A inhibitor such as, e.g., ketoconazole or itraconazole, is indicated, the subject may be administered a reduced dose of mifepristone, where the amount of the reduced dose is less than the original mifepristone dose by about 300 mg mifepristone per day, and the reduced dose of mifepristone may be subsequently titrated upwards (i.e., increased in subsequent dose administrations) in increments of about 300 mg mifepristone. In embodiments, such upward titration of the reduced dose in increments of 300 mg/day may be subjected to a maximum daily dosage of about 600 mg/day, or greater than 800 mg/day, or of about 900 mg/day, or of about 1200 mg/day, or of about 1500 mg/day. In embodiments, such upward titration of the dosage of the reduced daily dose of mifepristone administered per day is capped at a maximum daily dose, wherein said maximum daily dose is selected from the group consisting of 900 milligrams (mg) mifepristone per day, greater than 800 mg mifepristone per day, and 600 mg mifepristone per day.

The subject may be monitored for clinical effects of the drugs, e.g., for clinical response to the GRM (e.g., mifepristone), adverse events, side-effects of any drug, at any stage or at all stages, of such incremental upward titration of the mifepristone dosage. The interval of time between administration of a reduced dose, or of an upwardly titrated reduced dose, and an upward titration of a dose of mifepristone may be an interval selected from two days, four days, one week, two weeks, one month, two months, and three months. In embodiments, the interval of time between upward titration of a reduced dose, or of an upwardly titrated reduced dose, and a subsequent upward titration of a dosage of the reduced dose of mifepristone is selected from one week, two weeks, three weeks, and four weeks. Monitoring the patient for clinical response may include monitoring the patient (e.g., to identify or determine if there are changes in) for glucose control, anti-diabetic medication requirement, insulin level, psychiatric symptoms, cushingoid appearance, acne, hirsutism, and monitoring the body weight of the patient (e.g., to identify or determine if there are changes in any one or more of these symptoms and characteristics).

In embodiments in which a subject has been receiving a first dose of mifepristone (e.g. a daily dose of mifepristone of about 1800 mg/day, or about 1500 mg/day, or about 1200 mg/day, or about 900 mg/day, or greater than 800 mg/day, or about 600 mg/day, or about 300 mg/day), and concomitant administration of mifepristone and a CYP3A inhibitor such as, e.g., ketoconazole or itraconazole, is indicated, the subject may be administered a reduced dose of mifepristone, where the amount of the reduced dose is less than the original mifepristone dose, and the reduced dose of mifepristone may be about 1500 mg mifepristone per day, or about 1500 mg/day, or about 1200 mg/day, or about 900 mg/day, or greater than 800 mg/day, or about 600 mg/day, or about 300 mg/day; and the subject may be monitored for clinical response to the GRM, or for other clinical effects of the drugs. In such embodiments, the reduced dose of mifepristone may be subsequently titrated upwards (i.e., increased in subsequent dose administrations) in increments of about 300 mg mifepristone. In embodiments, such upward titration of the reduced dose in increments of 300 mg/day may be subjected to a maximum daily dosage of about 600 mg/day, or greater than 800 mg/day, or of about 900 mg/day, or of about 1200 mg/day, or of about 1500 mg/day. In embodiments, such upward titration of the dosage of the reduced daily dose of mifepristone administered per day is capped at a maximum daily dose, wherein said maximum daily dose is selected from the group consisting of 900 milligrams (mg) mifepristone per day, greater than 800 mg mifepristone per day, and 600 mg mifepristone per day.

The subject may be monitored for clinical response to the drugs, including e.g., clinical response to the GRM (e.g., mifepristone), for adverse events, side-effects of any of the drugs, at any stage, or at all stages, of such incremental upward titration of the mifepristone dosage. Upward titration of a reduced dose of mifepristone may be performed every two days, or every four days, or every week, or every two weeks, or every month, or every two months. In embodiments, the interval of time between upward titration of a reduced dose, or of an upwardly titrated reduced dose, and a subsequent upward titration of a dosage of the reduced dose of mifepristone is selected from one week, two weeks, three weeks, and four weeks.

Applicant discloses herein that concomitant treatment with both mifepristone and ketoconazole, and concomitant treatment with both mifepristone and itraconazole, may lead to small increases in plasma levels of mifepristone as measured by $C_{max}$ and as measured by AUC. For example, as disclosed in Table 3 below, concomitant administration of mifepristone and ketoconazole led to about 28% (27.59%, or about 30%) increase in mifepristone $C_{max}$ and about 38% (38.01%, about 40%) increase in mifepristone AUC. Thus, in embodiments, a mifepristone dose administered to a subject receiving concomitant administration of mifepristone and ketoconazole may be reduced in compensation for such a small increase in mifepristone plasma levels. In addition, as disclosed in Table 9 below, concomitant administration of mifepristone and itraconazole led to about 20% increase in mifepristone $C_{max}$ and about 10% increase in mifepristone AUC. Thus, in embodiments, a mifepristone dose administered to a subject receiving concomitant administration of mifepristone and itraconazole may be reduced in compensation for such a small increase in mifepristone plasma levels.

In embodiments in which a subject has been receiving a GRM such as, e.g., mifepristone, and concomitant administration of the GRM and a CYP3A inhibitor such as, e.g., ketoconazole or itraconazole, is indicated, the reduced dose of GRM may be reduced by about, e.g., 20% to about 22%, of the original dose of GRM. In embodiments in which a subject has been receiving a GRM, and concomitant administration of the GRM and a CYP3A inhibitor such as, e.g., ketoconazole or itraconazole, is indicated, the reduced dose of GRM may be reduced by about 23% of the original dose of GRM. In embodiments in which a subject has been receiving a GRM, and concomitant administration of the GRM and a CYP3A inhibitor such as, e.g., ketoconazole or itraconazole, is indicated, the reduced dose of GRM may be reduced by about 28% of the original dose of GRM. In embodiments in which a subject has been receiving a GRM, and concomitant administration of the GRM and a CYP3A inhibitor such as, e.g., ketoconazole or itraconazole, is indicated, the reduced dose of GRM may be reduced by about 29% of the original dose of GRM. In embodiments, the reduced dose of GRM is a dose of GRM that is at least about 90% of the original dose of GRM; and may be a dose of GRM that is at least about 85%, or about 80%, or about 78%, or about 77%, or about 75%, or about 72%, or about 71%, or about 67%, or about 62%, or about 60%, or about 50%, or about 34%, or about 25% of the original dose of GRM.

Applicant further discloses herein that, since mifepristone provides added therapeutic benefit synergistic with steroidogenesis inhibitors such as, e.g., ketoconazole, levoketoconazole, metyrapone, etomidate, mitotane, osilodrostat (LCI699), concomitant administration of mifepristone and such a steroidogenesis inhibitor makes it possible to reduce the dose of the steroidogenesis inhibitor while maintaining mifepristone levels effective for therapy for a patient. Such a reduction in, e.g., ketoconazole dose provides the benefit of reducing the risk of toxic side-effects associated with all ketoconazole treatments. Thus, concomitant administration of a steroidogenesis inhibitor such as, e.g., ketoconazole or others, with mifepristone, by allowing reduced steroidogenesis inhibitor dose, provides improved, synergistic therapeutic benefits. In embodiments, such steroidogenesis inhibitor dose reduction may be used to wean the patient off steroidogenesis inhibitor, leading to lower and lower steroidogenesis inhibitor doses, thereby reducing the risk of steroidogenesis inhibitor toxicity. In embodiments in which the steroidogenesis inhibitor is ketoconazole, such ketoconazole dose reduction may be used to wean the patient off ketoconazole, leading to lower and lower ketoconazole doses, with concomitant upward adjustment of mifepristone dosage as needed, ultimately leading to treatment with mifepristone alone and cessation of ketoconazole treatment (lessening the risk of liver damage and other toxicities). Embodiments in which concomitant administration of ketoconazole and mifepristone may lead to ketoconazole dose reduction (as compared to the ketoconazole dose in the absence of mifepristone) include, e.g., Cushing's syndrome and hormone-sensitive cancers such as breast, ovarian, and prostate cancer, and other disorders susceptible of treatment by mifepristone.

In embodiments, concomitant administration of a steroidogenesis inhibitor, such as, e.g., ketoconazole, and mifepristone allows for administration of an effective dose of the steroidogenesis inhibitor that is a reduced dose of steroidogenesis inhibitor as compared to the steroidogenesis inhibitor dose administered in the absence of mifepristone. For example, Applicant discloses herein that concomitant administration of mifepristone and ketoconazole makes it possible to reduce the dose of ketoconazole while maintaining effective therapy for the patient. Such a reduction in ketoconazole dose provides the benefit of reducing the amount of ketoconazole administered to the subject. Embodiments in which a subject is concomitantly administered ketoconazole and mifepristone allow for ketoconazole dose reduction (as compared to the ketoconazole dose in the absence of mifepristone) include, e.g., Cushing's syndrome and hormone-sensitive cancers such as breast, ovarian, and prostate cancer, and other disorders susceptible of treatment by ketoconazole and other steroidogenesis inhibitors.

In embodiments, the reduced dose of steroidogenesis inhibitor such as, e.g., ketoconazole, administered to a subject also concomitantly receiving mifepristone is a dose of steroidogenesis inhibitor that is at least about 5% less than the original dose of steroidogenesis inhibitor, where the original dose of steroidogenesis inhibitor is the dose the subject had been, or would have been, administered in the absence of mifepristone co-administration. In embodiments, the reduced dose of steroidogenesis inhibitor is a dose of steroidogenesis inhibitor that is at least about 10% less than the original dose of steroidogenesis inhibitor; and may be a dose of steroidogenesis inhibitor that is at least about 15%, or about 20%, or about 25%, or about 33%, or about 50%, or about 66%, or about 75% less than the original dose of steroidogenesis inhibitor.

Applicant discloses herein the use of a glucocorticoid receptor modulator (GRM) for treating Cushing's syndrome in a patient, wherein the GRM is for once-daily administration, comprising reducing the once-daily dose of said GRM from an original once-daily (OD) dose to an adjusted OD dose less than said original OD dose when the patient is receiving concomitant administration of a CYP3A inhibitor. In embodiments in which a once-daily dose of a GRM is used, and in which concomitant administration of GRM and a CYP3A inhibitor is indicated, the reduced dose of the GRM may be about at least about 15%, or about 20%, or about 22%, or about 23%, or about 25%, or about 28%, or about 29%, or about 33%, or about 38%, or about 40%, or about 50%, or about 66%, or about 75% less than the original dose of the GRM. In embodiments in which the once-daily dose of said GRM is about 1200 mg GRM per day, and concomitant administration of GRM and a CYP3A inhibitor is indicated, the reduced dose of GRM may be about 900 mg GRM per day; may be greater than 800 mg GRM per day; may be about 600 mg GRM per day; or may be about 300 mg GRM per day.

In embodiments, Applicant discloses herein the use of a glucocorticoid receptor modulator (GRM) for treating Cushing's syndrome in a patient, wherein the GRM is for once-daily administration, comprising reducing the once-daily dose of said GRM from an original once-daily (OD) dose to an adjusted OD dose that is at least about 25% less than said original OD dose when the patient is receiving concomitant administration of a CYP3A inhibitor. In embodiments of such uses, said original once-daily (OD) dose is selected from greater than 800 mg/day, 900 mg per day and 1200 mg per day of said GRM, and said adjusted OD dose is selected from greater than 800 mg/day and 600 mg per day of said GRM. In embodiments of such uses, said original once-daily (OD) dose is 600 milligrams (mg) per day of said GRM, and said adjusted OD dose is 300 mg per day of said GRM, further comprising titrating the adjusted OD dose to 600 mg per day of said GRM. In embodiments of such uses, said GRM is mifepristone and said CYP3A inhibitor is a strong CYP3A inhibitor. In embodiments of such uses, said CYP3A inhibitor is ketoconazole or itraconazole.

Applicant also discloses herein the use of a glucocorticoid receptor modulator (GRM) for treating symptoms associated with elevated cortisol levels in a patient, wherein the GRM is for once-daily administration, comprising reducing the once-daily (OD) dose of said GRM from an original OD dose to an adjusted dose that is at least about 25% less than said original OD dose when the patient is receiving concomitant administration of a CYP3A inhibitor. In embodiments of such uses, said original once-daily (OD) dose is selected from greater than 800 mg/day, 900 mg per day and 1200 mg per day of said GRM, and said adjusted OD dose of GRM is 600 mg per day of said GRM. In embodiments of such uses, said original once-daily (OD) dose is 600 milligrams (mg) per day of said GRM, and said adjusted OD dose is 300 mg per day of said GRM, further comprising titrating the adjusted OD dose to 600 mg per day of said GRM. In embodiments of such uses, said GRM is mifepristone and said CYP3A inhibitor is a strong CYP3A inhibitor. In embodiments of such uses, said CYP3A inhibitor is ketoconazole or itraconazole.

Applicant further discloses herein the use of a GRM for controlling hyperglycemia secondary to hypercortisolism in a patient, wherein the GRM is for once-daily administration, comprising reducing the once-daily (OD) dose of said GRM from an original OD dose to an adjusted OD dose that is at least about 25% less than said original OD dose when the patient is receiving concomitant administration of a CYP3A inhibitor. In embodiments of such uses, said original once-daily (OD) dose is 1200 milligrams (mg) per day of said GRM, and said adjusted OD dose of GRM is 900 mg per day of said GRM. In embodiments of such uses, said original once-daily (OD) dose is selected from greater than 800 mg/day, 900 mg per day and 1200 mg per day of said GRM, and said adjusted OD dose of GRM is selected from greater than 800 mg/day and 600 mg per day of said GRM. In embodiments of such uses, said once-daily dose of GRM is titrated up to greater than 800 mg/day, e.g., to 900 mg per day. In embodiments of such uses, said original once-daily (OD) dose is 600 milligrams (mg) per day of said GRM, and said adjusted OD dose is 300 mg per day of said GRM, further comprising titrating the adjusted OD dose to 600 mg per day of said GRM or to greater than 800 mg/day of said GRM. In embodiments of such uses, said GRM is mifepristone and said CYP3A inhibitor is a strong CYP3A inhibitor. In embodiments of such uses, said GRM is mifepristone and said CYP3A inhibitor is a strong CYP3A inhibitor. In embodiments of such uses, said CYP3A inhibitor is ketoconazole or itraconazole.

Applicant yet further discloses herein the use of a GRM for controlling hyperglycemia secondary to hypercortisolism in a patient with endogenous Cushing's syndrome, wherein the GRM is for once-daily administration, comprising administering a once-daily dose of 600 milligrams (mg) GRM, such as, e.g., mifepristone, when the patient is receiving concomitant administration of a CYP3A inhibitor. In embodiments of such uses, the CYP3A inhibitor is ketoconazole or itraconazole. In embodiments of such uses, said once-daily dose of GRM is titrated up to greater than 800 mg/day, e.g., to 900 mg per day following administration of a dose or doses of 600 mg once per day. In embodiments of such uses, said once-daily dose of GRM is titrated up to 600 mg per day from 300 mg per day.

Applicant even further discloses herein the use of a GRM for controlling hyperglycemia secondary to hypercortisolism in a patient with endogenous Cushing's syndrome, wherein the GRM is for once-daily administration, comprising administering a once-daily dose of greater than 800 mg mifepristone, e.g., 900 mg mifepristone when the patient is receiving concomitant administration of a CYP3A inhibitor. In embodiments of such uses, the CYP3A inhibitor is ketoconazole or itraconazole. In embodiments of such uses, said once-daily dose of mifepristone is titrated up to greater than 800 mg/day, e.g., to 900 mg per day from 300 mg per day.

Applicant provides definitions of some terms used in the present disclosure.

Definitions

The abbreviations used herein have their conventional meaning within the chemical and biological arts.

"Patient", "patient in need", "subject", "subject in need" and the like refer to a person having, or suspected of having, a disease or condition which may be treated by administration of a therapeutic drug.

As used herein, the term "Cushing's syndrome" refers to an array of symptoms caused by excess cortisol. Cushing's syndrome includes endogenous Cushing's syndrome and ectopic Cushing's syndrome. Such symptoms include, for example, elevated blood pressure, elevated blood glucose, increased weight (typically in the mid-section, and in the face causing a characteristic "moon-face"), immune suppression, thin skin, acne, depression, hirsutism, and other symptoms.

As used herein, "Cushing's Disease" refers to pituitary-dependent Cushing's syndrome, e.g., excess cortisol caused by pituitary abnormality (typically a pituitary tumor). Cushing's Disease is thus a disease that is a particular type of Cushing's syndrome. The term Cushing's syndrome thus includes reference to Cushing's Disease.

As used herein, a "patient suffering from Cushing's syndrome" refers to any patient suffering from Cushing's syndrome, including endogenous Cushing's syndrome; Cushing's Disease; or a condition associated with Cushing's syndrome. A condition associated with Cushing's syndrome may be, without limitation, a condition associated with endogenous Cushing's syndrome; hyperglycemia secondary to hypercortisolism; a condition of hypercortisolism in an endogenous Cushing's syndrome patient, said patient having type 2 diabetes mellitus or glucose intolerance; a condition of hyperglycemia secondary to hypercortisolism in an endogenous Cushing's syndrome patient, said patient having type 2 diabetes mellitus or glucose intolerance and having failed surgery; hyperglycemia secondary to hypercortisolism in an endogenous Cushing's syndrome patient, said patient having type 2 diabetes mellitus or glucose intolerance and having failed surgery or who is not a candidate for surgery; and other conditions associated with Cushing's syndrome.

"Treat", "treating" and "treatment" refer to any indicia of success in the treatment or amelioration of a pathology or condition, including any objective or subjective parameter such as abatement; remission; diminishing of symptoms or making the pathology or condition more tolerable to the patient; slowing in the rate of degeneration or decline; making the final point of degeneration less debilitating; or improving a patient's physical or mental well-being. The treatment or amelioration of symptoms can be based on objective or subjective parameters; including the results of a physical examination; histopathological examination (e.g., analysis of biopsied tissue); laboratory analysis of urine, saliva, tissue samples, serum, plasma, or blood; or imaging.

As used herein, "treating a patient who is suffering from Cushing's syndrome", or treating a subject who is suffering from Cushing's syndrome", or similar phrases refer to, without limitation, treating a patient suffering from Cushing's syndrome, including endogenous Cushing's syndrome; treating a patient suffering from Cushing's Disease; or treating a patient suffering from a condition associated with Cushing's syndrome. A condition associated with Cushing's syndrome is discussed above. For example, treating a patient who is suffering from Cushing's syndrome may include administering mifepristone or other GRA to control hyperglycemia secondary to hypercortisolism in adult patients with endogenous Cushing's syndrome who have type 2 diabetes mellitus or glucose intolerance and have failed surgery or are not candidates for surgery.

As used herein, the term "administration" refers to the delivery of a drug or other therapeutic into the body of a patient in need of treatment by the drug or therapeutic, effective to achieve a therapeutic effect. Administration may be by any suitable route of administration, including, for example, oral administration; intravenous administration; subcutaneous administration; parenteral administration; intra-arterial administration; nasal administration; topical administration; and other routes of administration.

As used herein, the terms "percent", "%" and "weight percent" when applied to a dosage administered to a subject, all refer to a percentage taken by comparing the weight of a first dose to that of a second dose, and multiplying the resulting decimal fraction by 100. Thus, for example, where an original mifepristone dose is 1200 milligrams (mg), a dose that is reduced by 50% is a dose of 600 mg mifepristone; and where an original mifepristone dose is 600 milligrams (mg), a dose that is reduced by 50% is a dose of 300 mg mifepristone; and so forth.

As used herein, the phrases "less than x by at least", "less than x by at least about", and the like refer to amounts equal to and less than the x, where x is a number. For example, the phrase "less than the original dosage by at least 25%" refers to dosage amounts that include 25% less than the original dosage as well as other percentages (e.g., 26%, 28%, etc.) less than the original dosage amount.

As used herein, the terms "effective amount," "amounts effective," therapeutic amount", and "therapeutically effective amount" refer to an amount or amounts of one or more pharmacological agents effective to treat, eliminate, or mitigate at least one symptom of the disease being treated. In some cases, "effective amount," "amounts effective," "therapeutic amount", and "therapeutically effective amount" can refer to an amount of a functional agent or of a pharmaceutical composition useful for exhibiting a detectable therapeutic or inhibitory effect.

As used herein, the term "simultaneously or sequentially administering" refers to administration of two compounds, such as a GRA and a CYP3A inhibitor, such that the two compounds are in the body at the same time in therapeutically effective amounts.

As used herein, "concomitant" means at the same, or nearly the same, time, and "concomitantly" refers to actions performed at the same, or nearly the same, time. As used herein, he terms "concurrent" and "concomitant" are equivalent and may be used interchangeably. The adverbs "concurrently" and "concomitantly" are equivalent and may be used interchangeably.

As used herein, the term "concomitant administration" of two or more drugs means administering two or more drugs at the same, or nearly the same, time. Concomitant administration of two or more drugs provides therapeutically effective amounts of the two or more drugs in the system of the subject at the same time. Concomitant administration includes administration of a GRA to a patient who has previously been administered a drug, such as a CYP3A inhibitor or a steroidogenesis inhibitor, and therapeutically effective levels of the CYP3A inhibitor or steroidogenesis inhibitor remain in the patient when the patient is administered the GRA (e.g., when the patient is administered mifepristone), and includes administration of a CYP3A inhibitor or a steroidogenesis inhibitor to a patient who has previously been administered a drug, such as a GRA, and therapeutically effective levels of the GRA remain in the patient when the patient is administered the CYP3A inhibitor or steroidogenesis inhibitor.

As used herein, "concomitantly administering drugs" means that two or more drugs are administered to a subject at the same, or nearly the same, time. Drugs that are concomitantly administered will each be present in therapeutically effective amounts in the system of the subject at the same time. Nearly the same time means that only a short amount of time separates two events, such as administration of a first drug and the administration of a second drug.

Events or actions that are "simultaneous" or that occur or are performed "simultaneously" are events that occur or are performed at the same time.

As used herein, "at the same time" means that two events occur or are performed within about five minutes of each other.

As used herein, "nearly the same time" means that two events occur or are performed within about a short time of each other.

As used herein, a "short time", a "short amount of time", a "short period of time", and the like mean a time that is less than about two hours, or less than about one hour, or less than about 45 minutes, or less than about 30 minutes, or less than about 20 minutes, or less than about 10 minutes, or less than about 7 minutes.

As used herein, the term "clinical effect" means changes in symptoms or signs characteristic of, or indicative of, a clinical condition or disorder. For example, where a subject is treated for Cushing's syndrome, including Cushing's Disease, a clinical effect may be a change in any one or more of blood pressure, blood glucose, other pre-diabetic symptom, weight, mid-section perimeter, facial characteristics (e.g., change in "moon-face" appearance), immune function, skin thickness, acne, depression or other mood symptom, hirsutism, and other symptoms.

As used herein, "monitoring for clinical response", e.g., monitoring a patient for clinical response to a GRA such as mifepristone, may include monitoring the patient (e.g., to identify or determine if there are changes in) for glucose control, anti-diabetic medication requirement, insulin level, psychiatric symptoms, cushingoid appearance, acne, hirsutism, and monitoring the body weight of the patient (e.g., to identify or determine if there are changes in any one or more of these symptoms and characteristics). Monitoring for clinical response may also include monitoring a patient for adverse events, for side-effects of any drug (including a GRA, a CYP3A inhibitor, a steroidogenesis inhibitor, and combinations of these). Thus, monitoring for clinical response may include monitoring for clinical effect of a drug such as a GRM, including clinical efficacy of the GRM; for clinical effect of a steroidogenesis inhibitor or CYP3A inhibitor; for possible adverse reaction to a steroidogenesis inhibitor or CYP3A inhibitor; for possible adverse reaction to the use of a steroidogenesis inhibitor or CYP3A inhibitor in combination with the GRM; for possible side-effects of a steroidogenesis inhibitor or CYP3A inhibitor, or their use in combination with the GRM; or combinations thereof.

As used herein, the term "AUC" means the area under the plasma concentration-time curve, and serves as a measure of the plasma levels of a drug in a subject to whom the drug has been administered.

As used herein, the term "$C_{max}$" means the maximum observed plasma concentration of a drug in a subject to whom the drug has been administered.

As used herein, the term "binding" refers to persistent contact, or adherence (however brief or intermittent), between two compounds.

As used herein, the terms "affinity", "binding affinity", and related terms refer to the strength and specificity of binding, such as binding between a ligand and its receptor. "Higher affinity" is used with reference to comparative binding between two ligands to a receptor, where the ligand which binds with higher affinity binds at a lower concentration than does the "lower affinity" ligand. For example, in a competitive binding experiment, a high affinity ligand will compete with a reference ligand for binding to a receptor at a lower concentration than will the low affinity ligand compete for binding at the receptor.

The term "specific binding" refers to binding that is more selective, and typically stronger, than mere non-specific adhesion between compounds. Specific binding may be exemplified by the binding which occurs between a ligand and its receptor.

Description of compounds useful in the methods disclosed herein, and suitable for the pharmaceutical compositions disclosed herein are described in accordance with principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc.

"Alkoxy" refers to an alkyl group having an oxygen atom that connects the alkyl group to the point of attachment: alkyl-O—. As for the alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

"Halogen" refers to fluorine, chlorine, bromine and iodine.

"Haloalkyl" refers to alkyl, as defined above, where some or all of the hydrogen atoms are replaced with halogen atoms. As for the alkyl group, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethane includes 1,1,1-trifluoromethyl.

"Haloalkoxy" refers to an alkoxy group where some or all of the hydrogen atoms are substituted with halogen atoms. As for the alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, N-oxide, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring heteroatoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heteroatoms" refers to O, S or N.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

"Isomers" refers to compounds with the same chemical formula but which are structurally distinguishable.

"Tautomer" refers to one of two or more structural isomers which exist in equilibrium and which are readily converted from one form to another.

As used herein, the term "ketoconazole" refers to the molecule having the chemical name "1-acetyl-4-[4-[[2-(2,4-dichlorophenyl)-2-[(1H-imidazol-1-yl)-methyl]-1,3-dioxolan-4-yl]methoxy]phenyl]piperazine)"; it is sold for clinical use under the name "NIZORAL®", and may also be referred to by the abbreviation "keto".

As used herein, the terms "steroid" and "steroids", and the phrase "steroidal backbone" in the context of glucocorticoid receptor antagonists containing such refers to glucocorticoid receptor antagonists that contain modifications of the basic structure of cortisol, an endogenous steroidal glucocorticoid receptor ligand. The basic structure of a steroidal backbone is provided as Formula I:

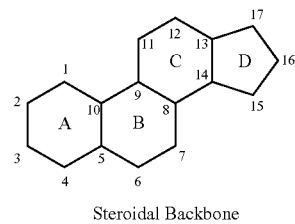

Formula I

Steroidal Backbone

The two most commonly known classes of structural modifications of the cortisol steroid backbone to create glucocorticoid antagonists include modifications of the 11-β hydroxy group and modification of the 17-β side chain (See, e. g., Lefebvre (1989) J. Steroid Biochem. 33: 557-563).

As used herein, the terms "progesterone receptor" and "PR" refer to a naturally occurring receptor which binds progesterone.

The term "aldosterone" refers to the naturally occurring mineralocorticoid hormone having the structure:

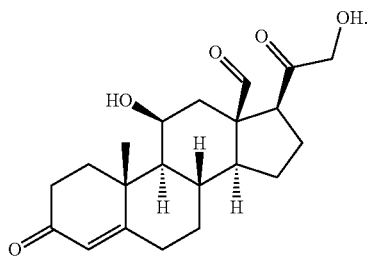

A mineralocorticoid receptor (MR), also known as a type I glucocorticoid receptor (GR I), is activated by aldosterone in humans.

The term "cortisol" refers to the naturally occurring glucocorticoid hormone (also known as hydrocortisone) having the structure:

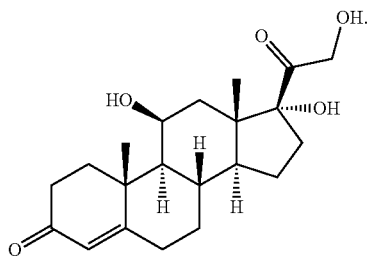

As used herein, the term glucocorticoid receptor (GR) refers to a receptor that binds a glucocorticoid, such as cortisol, dexamethasone, or other molecules. A glucocorticoid receptor, also known as a corticosteroid receptor or as a type II glucocorticoid receptor (GR II), and in humans, as a cortisol receptor, is activated by cortisol in humans (or, e.g., by corticosterone ("cortisone") in some other animals, such as rats and mice). The human cortisol receptor (GR II receptor, Genbank: P04150) specifically binds to cortisol and/or cortisol analogs (e.g. dexamethasone). The term includes isoforms of GR II, recombinant GRII, and mutated GRII.

As used herein, the term glucocorticoid receptor modulator (GRM) refers to an agent that affects the action of a glucocorticoid receptor (GR). Such modulation may include activation (agonist action), partial activation (partial agonist action), inhibition (reduction in activation of the receptor under conditions where it would otherwise be activated, such as in the presence of cortisol), and blockade (complete or near complete suppression of activation of the receptor under conditions where it would otherwise be activated, such as in the presence of cortisol). GRMs may affect the activity of a GR by increasing or by decreasing the activity of the GR. GRMs include steroids, and, in embodiments, include pyrimidinediones; azadecalins; fused-ring azadecalins; heteroaryl-ketone fused-ring azadecalins; and other compounds.

As used herein, the terms "glucocorticoid agonist", "glucocorticoid receptor agonist", "glucocorticoid receptor type II agonist", and "GRII agonist" refer to a compound or agent which may bind to and activate a cortisol receptor. Such agents include, for example, cortisol, dexamethosone, prednisone, and other compounds and agents which bind to and activate a GRII.

As used herein, the terms "glucocorticoid antagonist", "glucocorticoid receptor antagonist", "glucocorticoid antagonist", "glucocorticoid receptor type II antagonist", "GRII antagonist", and "GRA" refer to agents that inhibit the action of a cortisol receptor; such inhibition may include interfering with the binding of a glucocorticoid agonist such as cortisol, dexamethosone, or other compound or agent which may bind to and activate a cortisol receptor. A GRA is a glucocorticoid receptor modulator. Inhibition constants ($K_i$) for GRAs against the human cortisol receptor may be between about 0.0001 nM and about 1,000 nM; preferably may be between about 0.0005 nM and about 10 nM, and most preferably between about 0.001 nM and about 1 nM.

The term "glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" refers to any composition or compound which inhibits any biological response associated with the binding of a GR to an agonist. By "specific," we intend the drug to preferentially bind to the GR rather than another nuclear receptors, such as mineralocorticoid receptor (MR) or progesterone receptor (PR).

By "specific," the drug preferentially binds to the GR rather than other nuclear receptors, such as mineralocorticoid receptor (MR), androgen receptor (AR), or progesterone receptor (PR). It is preferred that the specific glucocorticoid receptor antagonist bind GR with an affinity that is 10× greater ($1/10^{th}$ the $K_d$ value) than its affinity to the MR, AR, or PR. In a more preferred embodiment, the specific glucocorticoid receptor antagonist binds GR with an affinity that is 100× greater ($1/100^{th}$ the $K_d$ value) than its affinity to the MR, AR, or PR.

In embodiments, a glucocorticoid receptor modulator (GRM) is a glucocorticoid receptor antagonist (GRA). In embodiments, the GRA is an antagonist of a glucocorticoid type II (GRII) receptor. In embodiments, the GRA binds preferentially to a GRII receptor as compared to its binding to a glucocorticoid type I (GRI) receptor. In embodiments, the GRA reduces the activation of a GRII receptor. In embodiments, the GRA reduces the activity of a GRII receptor. In embodiments, the GRA may bind to a progesterone receptor (PR), and may bind to a glucocorticoid receptor with higher affinity than it binds to PR. In embodiments, the GRA is mifepristone. In embodiments, the GRA is a selective inhibitor of the glucocorticoid receptor. In embodiments, the GRA may only poorly bind to PR, or may not measurably bind to PR.

As used herein, a "steroidal glucocorticoid receptor antagonist" means a molecule including a steroid backbone structure which antagonizes the binding of cortisol, corticosterone, or dexamethasone to a glucocorticoid receptor, or which reduces or blocks the activation of a glucocorticoid receptor by cortisol, corticosterone, or dexamethasone. Examples of steroidal glucocorticoid receptor antagonists include mifepristone, monodemethylated mifepristone, didemethylated mifepristone, 17-α-[3'-hydroxy-propynyl] mifepristone, ulipristal (CDB-2914), CDB-3877, CDB-3963, CDB-3236, CDB-4183, cortexolone, dexamethasoneoxetanone, 19-nordeoxycorticosterone, 19-norprogesterone, cortisol-21-mesylate; dexamethasone-21-mesylate, 11(-(4-dimethylaminoethoxyphenyl)-17(-propynyl-17(-hydroxy-4, 9-estradien-3one, and 17(-hydroxy-17(-19-(4-methylphenyl)androsta-4,9(11)-dien-3-one.

Mifepristone is a glucocorticoid receptor modulator (GRM), and in particular, is a glucocorticoid receptor antagonist (GRA), which binds to GRII (and which also binds to a progesterone receptor). As used herein, the term "mifepristone" refers to 11β-(4-dimethylaminophenyl)-17β-hydroxy-17α-(1-propynyl)-estra-4,9-dien-3-one), also referred to as RU486, or as RU38.486, or as 17-beta-hydroxy-11-beta-(4-dimethyl-aminophenyl)-17-alpha-(1-propynyl)-estra-4,9-dien-3-one). Mifepristone binds to the glucocorticoid receptor (GR), typically with high affinity, and inhibits the biological effects initiated/mediated by the binding of any cortisol or cortisol analogue to a GR receptor. Salts, hydrates and prodrugs of mifepristone are all included in the term "mifepristone" as used herein. Thus, used herein, "mifepristone" refers to the molecule that has the following structure:

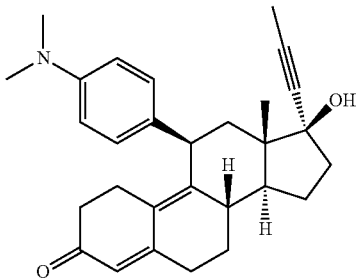

and to salts, hydrates and prodrugs thereof, and pharmaceutical compositions thereof. Mifepristone is also sometimes abbreviated as "mife" and "MIFE".

Metabolites of mifepristone include RU42633 (desmethylmifepristone: (8S,11R,13S,14S,17S)-17-hydroxy-13-methyl-11-[4-(methylamino)phenyl]-17-prop-1-ynyl-1,2,6,7,8,11,12,14,15,16-decahydrocyclopenta[a]phenanthren-3-one); RU42698 (22-hydroxy mifepristone: (8S,11R,13S,14S,17S)-11-[4-(dimethylamino)phenyl]-17-hydroxy-17-(3-hydroxyprop-1-ynyl)-13-methyl-1,2,6,7,8,11,12,14,15,16-decahydrocyclopenta[a]phenanthren-3-one); and RU42848 (didesmethylmifepristone: (8S,11R,13S,14S,17S)-11-(4-aminophenyl)-17-hydroxy-13-methyl-17-prop-1-ynyl-1,2,6,7,8,11,12,14,15,16-decahydrocyclopenta[a] phenanthren-3-one), among others.

In some embodiments, the GRA comprises a steroidal backbone with at least one phenyl-containing moiety in the 11-β position of the steroidal backbone. In some cases, the phenyl-containing moiety in the 11-β position of the steroidal backbone is a dimethylaminophenyl moiety. In some cases, the GRA is mifepristone. In some embodiments, the GRA is selected from the group consisting of 11β-(4-dimethylaminoethoxyphenyl)-17α-propynyl-17β-hydroxy-4,9 estradien-3-one and (17α)-17-hydroxy-19-(4-methylphenyl)androsta-4,9(11)-dien-3-one. In some embodiments, the GRA is (11β,17β)-11-(1,3-benzodioxol-5-yl)-17-hydroxy-17-(1-propynyl)estra-4,9-dien-3-one.

As used herein, the phrase "non-steroidal backbone" in the context of glucocorticoid receptor antagonists containing such refers to glucocorticoid receptor antagonists that do not share structural homology to, or are not modifications of, cortisol. Such compounds include, for example, small molecules, synthetic mimetics and analogs of proteins, including partially peptidic, pseudopeptidic and non-peptidic molecular entities.

In some embodiments, the GRA is a non-steroidal compound. In embodiments, non-steroidal GRA compounds include compounds having a cyclohexyl-pyrimidine backbone; non-steroidal GRA compounds having a fused azadecalin backbone; non-steroidal GRA compounds having a heteroaryl ketone fused azadecalin backbone; and non-steroidal GRA compounds having an octahydro fused azadecalin backbone. Exemplary glucocorticoid receptor antagonists having a cyclohexyl-pyrimidine backbone include those described in U.S. Pat. No. 8,685,973. Exemplary glucocorticoid receptor antagonists having a fused azadecalin backbone include those described in U.S. Pat. Nos. 7,928,237; and 8,461,172. Exemplary glucocorticoid receptor antagonists having a heteroaryl ketone fused azadecalin backbone include those described in U.S. Pat. No. 8,859,774. Exemplary glucocorticoid receptor antagonists having an octahydro fused azadecalin backbone include those described in U.S. Patent Application Publication 20150148341.

In some cases, the GRA having a non-steroidal backbone is a cyclohexyl pyrimidine. In some cases, wherein the cyclohexyl pyrimidine has the following formula:

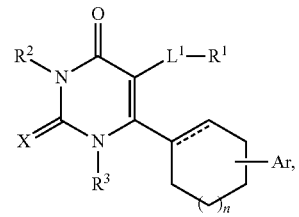

wherein the dashed line is absent or a bond; X is selected from the group consisting of O and S; $R^1$ is selected from the group consisting of cycloalkyl, heterocycloalkyl, aryl and heteroaryl, optionally substituted with from 1 to 3 $R^{1a}$ groups; each $R^{1a}$ is independently selected from the group consisting of H, $C_{1-6}$ alkyl, $C_{2-6}$ alkenyl, $C_{2-6}$ alkynyl, $C_{1-6}$ alkoxy, $C_{1-6}$ alkyl $OR^{1b}$, halogen, $C_{1-6}$ haloalkyl, $C_{1-6}$ haloalkoxy, $OR^{1b}$, $NR^{1b}R^{1c}$ $C(O)R^{1b}$, $C(O)OR^{1b}$, $OC(O)R^{1b}$, $C(O)NR^{1b}R^{1c}$, $NR^{1b}C(O)R^{1c}$, $SO_2R^{1b}$, $SO_2NR^{1b}R^{1c}$ cycloalkyl, heterocycloalkyl, aryl and heteroaryl; $R^{1b}$ and $R^{1c}$ are each independently selected from the group consisting of H and $C_{1-6}$ alkyl; $R^2$ is selected from the group consisting of H, $C_{1-6}$ alkyl, $C_{1-6}$ alkyl-$OR^{1b}$, $C_{1-6}$ alkyl $NR^{1b}R^{1c}$ and $C_{1-6}$ alkylene heterocycloalkyl; $R^3$ is selected from the group consisting of H and $C_{1-6}$ alkyl; Ar is aryl, optionally substituted with 1-4 $R^4$ groups; each $R^4$ is independently selected from the group consisting of H, $C_{1-6}$ alkyl, $C_{1-6}$ alkoxy, halogen, $C_{1-6}$ haloalkyl and $C_{1-6}$ haloalkoxy; $L^1$ is a bond or $C_{1-6}$ alkylene; and subscript n is an integer from 0 to 3, or salts and isomers thereof.

In some cases, the GRA having a non-steroidal backbone is a fused azadecalin. In some cases, the fused azadecalin is a compound having the following formula:

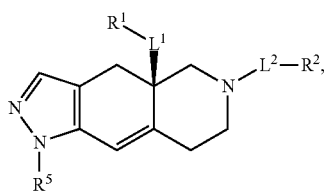

wherein L¹ and L² are members independently selected from a bond and unsubstituted alkylene; R¹ is a member selected from unsubstituted alkyl, unsubstituted heteroalkyl, unsubstituted heterocycloalkyl, —OR$^{1A}$, NR$^{1C}$R$^{1D}$, —C(O) NR$^{1C}$R$^{1D}$ and —C(O)OR$^{1A}$, wherein R$^{1A}$ is a member selected from hydrogen, unsubstituted alkyl and unsubstituted heteroalkyl, R$^{1C}$ and R$^{1D}$ are members independently selected from unsubstituted alkyl and unsubstituted heteroalkyl, wherein R$^{1C}$ and R$^{1D}$ are optionally joined to form an unsubstituted ring with the nitrogen to which they are attached, wherein said ring optionally comprises an additional ring nitrogen; R² has the formula:

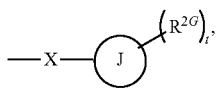

wherein R$^{2G}$ is a member selected from hydrogen, halogen, unsubstituted alkyl, unsubstituted heteroalkyl, unsubstituted cycloalkyl, unsubstituted heterocycloalkyl, —CN, and —CF₃; J is phenyl; t is an integer from 0 to 5; X is —S(O₂)—; and R⁵ is phenyl optionally substituted with 1-5 R$^{5A}$ groups, wherein R$^{5A}$ is a member selected from hydrogen, halogen, —OR$^{5A1}$, S(O₂)NR$^{5A2}$R$^{5A3}$, —CN, and unsubstituted alkyl, wherein R$^{5A1}$ is a member selected from hydrogen and unsubstituted alkyl, and R$^{5A2}$ and R$^{5A3}$ are members independently selected from hydrogen and unsubstituted alkyl, or salts and isomers thereof.

In some cases, the GRA having a non-steroidal backbone is a heteroaryl ketone fused azadecalin or an octahydro fused azadecalin. In some cases, the heteroaryl ketone fused azadecalin has the formula:

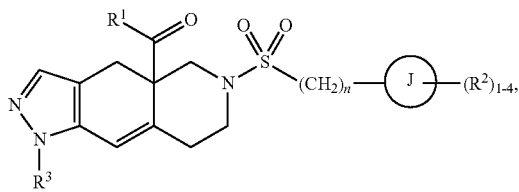

wherein R¹ is a heteroaryl ring having from 5 to 6 ring members and from 1 to 4 heteroatoms each independently selected from the group consisting of N, O and S, optionally substituted with 1-4 groups each independently selected from R$^{1a}$; each R$^{1a}$ is independently selected from the group consisting of hydrogen, C$_{1-6}$ alkyl, halogen, C$_{1-6}$ haloalkyl, C$_{1-6}$ alkoxy, C$_{1-6}$ haloalkoxy, CN, N-oxide, C$_{3-8}$ cycloalkyl, and C$_{3-8}$ heterocycloalkyl; ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S; each R² is independently selected from the group consisting of hydrogen, C$_{1-6}$ alkyl, halogen, C$_{1-6}$ haloalkyl, C$_{1-6}$ alkoxy, C$_{1-6}$ haloalkoxy, C$_{1-6}$ alkyl-C$_{1-6}$ alkoxy, CN, OH, NR$^{2a}$R$^{2b}$, C(O)R$^{2a}$, C(O)OR$^{2a}$, C(O)NR$^{2a}$R$^{2b}$, SR$^{2a}$, S(O)R$^{2a}$, S(O)₂R$^{2a}$, C$_{3-8}$ cycloalkyl, and C$_{3-8}$ heterocycloalkyl, wherein the heterocycloalkyl groups are optionally substituted with 1-4 R$^{2c}$ groups; alternatively, two R² groups linked to the same carbon are combined to form an oxo group (=O); alternatively, two R² groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 R$^{2d}$ groups; R$^{2a}$ and R$^{2b}$ are each independently selected from the group consisting of hydrogen and C$_{1-6}$ alkyl; each R$^{2c}$ is independently selected from the group consisting of hydrogen, halogen, hydroxy, C$_{1-6}$ alkoxy, C$_{1-6}$ haloalkoxy, CN, and NR$^{2a}$R$^{2b}$; each R$^{2d}$ is independently selected from the group consisting of hydrogen and C$_{1-6}$ alkyl, or two R$^{2d}$ groups attached to the same ring atom are combined to form (=O); R³ is selected from the group consisting of phenyl and pyridyl, each optionally substituted with 1-4 R$^{3a}$ groups; each R$^{3a}$ is independently selected from the group consisting of hydrogen, halogen, and C$_{1-6}$ haloalkyl; and subscript n is an integer from 0 to 3; or salts and isomers thereof.

In some cases, the octahydro fused azadecalin has the formula:

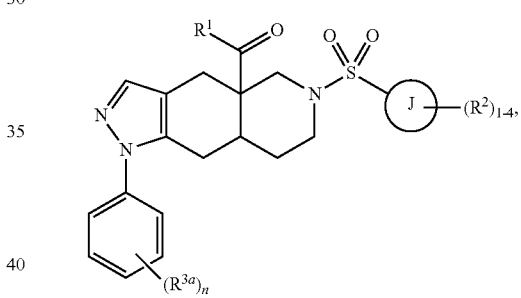

wherein R¹ is a heteroaryl ring having from 5 to 6 ring members and from 1 to 4 heteroatoms each independently selected from the group consisting of N, O and S, optionally substituted with 1-4 groups each independently selected from R$^{1a}$; each R$^{1a}$ is independently selected from the group consisting of hydrogen, C$_{1-6}$ alkyl, halogen, C$_{1-6}$ haloalkyl, C$_{1-6}$ alkoxy, C$_{1-6}$ haloalkoxy, N-oxide, and C$_{3-8}$ cycloalkyl; ring J is selected from the group consisting of an aryl ring and a heteroaryl ring having from 5 to 6 ring members and from 1 to 4 heteroatoms each independently selected from the group consisting of N, O and S; each R² is independently selected from the group consisting of hydrogen, C$_{1-6}$ alkyl, halogen, C$_{1-6}$ haloalkyl, C$_{1-6}$ alkoxy, C$_{1-6}$ haloalkoxy, C$_{1-6}$ alkyl-C$_{1-6}$ alkoxy, CN, OH, NR$^{2a}$R$^{2b}$, C(O)R$^{2a}$, C(O)OR$^{2a}$, C(O)NR$^{2a}$R$^{2b}$, SR$^{2a}$, S(O)R$^{2a}$, S(O)₂R$^{2a}$, C$_{3-8}$ cycloalkyl, and C$_{3-8}$ heterocycloalkyl having from 1 to 3 heteroatoms each independently selected from the group consisting of N, O and S; alternatively, two R² groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 R$^{2c}$ groups; R$^{2a}$, R$^{2b}$ and R$^{2c}$ are each independently selected from the group consisting of hydrogen and $C_{1-6}$ alkyl; each $R^{3a}$ is independently halogen; and subscript n is an integer from 0 to 3, or salts and isomers thereof.

Further examples of non-steroidal glucocorticoid receptor antagonists include, for example N-(2-[4,4',441-trichlorotrityl]oxyethyl)morpholine; 1-(2[4,4',4"-trichlorotrityl]oxyethyl)-4-(2-hydroxyethyl)piperazine dimaleate; N—([4,4',4"]-trichlorotrityl)imidazole; 9-(3-mercapto-1,2,4-triazolyl)-9-phenyl-2,7-difluorofluorenone; 1-(2-chlorotrityl)-3,5-dimethylpyrazole; 4-(morpholinomethyl)-A-(2-pyridyl)benzhydrol; 5-(5-methoxy-2-(N-methylcarbamoyl)-phenyl)dibenzosuberol; N-(2-chlorotrityl)-L-prolinol acetate; 1-(2-chlorotrityl)-1,2,4-triazole; 1,S-bis(4,4',4"-trichlorotrityl)-1,2,4-triazole-3-thiol; 4a(S)-Benzyl-2(R)-chloroethynyl-1,2,3,4,4α,9,10,10α(R)-octahydro-phenanthrene-2,7-diol ("CP 394531"), 4α(S)-Benzyl-2(R)-prop-1-ynyl-1,2,3,4,4α,9,10,10α(R)-octahydro-phenanthrene-2,7-diol ("CP-409069"), trans-(1R, 2R)-3,4-dichloro-N-methyl-N-[2-1 pyrrolidinyl)cyclohexyl] benzeneacetamide, bremazocine, and ethylketocyclazocine.

As used herein, the term "hormone-sensitive cancer" refers to any cancer which may be affected by a hormone; hormones typically increase proliferation of hormone-sensitive cancers. Hormone sensitive cancers include, e.g., prostate cancer and other androgen-sensitive cancers; breast cancer, ovarian cancer and other estrogen-sensitive or progesterone-sensitive cancers.

As used herein, the term "chemotherapy" refers to medical treatments typically used to treat cancer. Chemotherapy treatments include the use of agents which are toxic to cancerous tissues and cells, or which act to slow or reduce the growth or spread of cancerous tissues and cells. Chemotherapy agents include antineoplastic agents and may be derived from natural compounds (e.g., taxols); may be, may mimic, or may reduce or block the actions of naturally occurring hormones, growth factors, or immunologically active molecules; may be synthetic small molecules; may be antibodies or antibody conjugates; and may be other agents. Exemplary chemotherapy agents include, but are not limited to, taxanes, taxol, docetaxel, paclitaxel, actinomycin, anthracyclines, doxorubicin, daunorubicin, valrubicin, bleomycin, cisplatin, trastuzumab (HERCEPTIN®), trastuzumab emtasine (KADCYLA®), imatinib (GLEEVEC®), eribulin (HALAVEN®), among others known in the art.

As used herein, a phrase of the form "the reduced dose of Z is a dose that is at least about X % less than the original dose" (where "Z" represents a pharmaceutical compound or pharmaceutical composition, and "X" represents a numerical value) is used to indicate that the reduced dose is an amount of Z calculated by 1) multiplying the amount of Z in the original dose by X % to obtain a multiplicative product, and 2) subtracting that product from the original dose. Thus, for example, where the original dose is 600 mg, and X % is 50%, the multiplicative product of 600 mg and 50% is 300 mg, and the reduced dose is 300 mg; and, for example, where the original dose is 900 mg, and X % is 66%, the multiplicative product of 900 mg and 66% is about 600 mg (594 mg), and the reduced dose is about 300 mg (306 mg).

As used herein, the terms "pharmaceutical composition" and "formulation" refer to compositions suitable for administration to a patient for treatment of a medical condition or for amelioration of symptoms of a medical condition. A pharmaceutical composition as disclosed herein includes an active ingredient (e.g., a GRA, such as, e.g., mifepristone; or a combination of a GRA and a SI, where the SI may be, e.g., ketoconazole) and a pharmaceutically acceptable excipient.

In embodiments, a pharmaceutical composition includes one or more active ingredients and one or more pharmaceutically acceptable excipients.

As used herein, the terms "pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

As used herein, the terms "sustained release," "slow release," "long acting," "prolonged release," and the like refer to a pharmaceutical composition or formulation containing at least one active ingredient (e.g., GRA, SI, or combination thereof) formulated to maintain a therapeutic concentration of active ingredient(s) in a patient for a longer period of time in comparison to formulations that are not designed for such sustained release. In some cases, the sustained release formulation maintains therapeutic concentration of one or more active ingredient(s) for, or for at least, one week, two weeks, three weeks, four weeks, five weeks, or six weeks. In some cases, the sustained release formulation is administered to a patient every one, two, three, four, five, or six weeks.

As used herein, a "steroidogenesis inhibitor" is a compound which reduces or blocks the synthesis of steroid molecules when administered to an animal, or subject, which normally produces steroids. Steroidogenesis inhibitors include, for example, ketoconazole, levoketoconazole, metyrapone, etomidate, mitotane, osilodrostat (LCI699), and other drugs. A steroidogenesis inhibitor may act by one or more of several mechanisms, including, e.g., blocking synthesis of steroid molecules (e.g., ketoconazole, metyrapone).

As used herein, the term "CYP enzyme" refers to a cytochrome P450 enzyme. Cytochrome P450 enzymes are important in many metabolic and catabolic reactions in humans and other animals, and play important roles in drug metabolism and action. Drug-drug interactions in which administration of one drug affects the concentration, half-life, activity, or other effect of another drug may include effects on CYP enzymes by induction of CYP enzymes (increasing the amount or activity of one or more CYP enzymes); inhibition (reducing the activity of one or more CYP enzymes); competition (competing for sites or occupying sites, e.g., as a substrate, of one or more CYP enzymes); or by other means. Particular CYP enzymes include, for example, CYP1A2, CYP2C9, CYP2C19, CYP2D6, and CYP3A enzymes.

As used herein, a "CYP3A inhibitor" is a compound which reduces or blocks the activity of the cytochrome CYP3A, or reduces or blocks the expression of the gene-product of CYP3A genes (e.g., inhibits transcription or translation of CYP3A genes). CYP3A inhibitors may be termed strong or moderate if their administration, along with a test drug known to be metabolized by CYP3A enzymes (such as, e.g., midazolam), raises the AUC (area under the concentration curve) of the test drug by greater than five-fold (strong CYP3A inhibitors) or by between two-fold and five-fold (moderate CYP3A inhibitors). Inhibitors of CYP3A include, for example, ketoconazole, itraconazole, fluconazole, cimetidine, nefazodone, ritonavir, nelfinavir, indinavir, atazanavir, amprenavir, fosamprenavir, boceprevir, clarithromycin, conivaptan, lopinavir, posaconazole, saquinavir, telaprevir, telithromycin, and voriconazole.

Strong CYP3A inhibitors include, for example, ketoconazole, itraconazole, nefazodone, ritonavir, nelfinavir, indinavir, atazanavir, amprenavir and fosamprenavir, clarithromycin, conivaptan, lopinavir/ritonavir, posaconazole, saquinavir, telithromycin, and voriconazole.

Metyrapone (also known as METOPIRONE®) is 2-methyl-1,2-bis-(3-pyridyl)-1-propanone. Metopirone is believed to reduce cortisol and corticosterone production by inhibiting the 11-β-hydroxylation reaction in the adrenal cortex.

Etomidate (also known as AMIDATE®) is R-(+)-ethyl-1-(1-phenylethyl)-1H-imidazole-5-carboxylate. Although primarily used as a rapid-onset anesthetic, etomidate also lowers plasma cortisol levels. It is believed to reduce corticosteroid synthesis in the adrenal cortex by inhibiting 11β-hydroxylase.

Ketoconazole (1-acetyl-4-[4-[[2-(2,4-dichlorophenyl)-2-[(1H-imidazol-1-yl)-methyl]-1,3-dioxolan-4-yl]methoxy]phenyl]piperazine) is often used to treat fungal infections (e.g., (NIZORAL®) for the treatment of fungal infections). In addition, ketoconazole is a steroidogenesis inhibitor and can reduce the production of steroid molecules (such as, e.g., steroid hormones), typically by blocking the metabolism of cholesterol. Ketoconazole thus may be used to treat excessive cortisol production (e.g., to treat Cushing's disease and Cushing's syndrome), to reduce androgen production (e.g., in patients with hormone-sensitive cancers such as prostate cancer), to reduce estrogen or progesterone production (e.g., in patients with hormone-sensitive cancers such as breast cancer), and other treatments.

However, ketoconazole and itraconazole often have serious deleterious effects on liver and other organs. Thus, it is desirable to minimize the dose of ketoconazole or itraconazole administered to a patient, and methods for reducing the dose of ketoconazole or itraconazole are desired.

Treatment Methods

Methods disclosed herein include methods of treating a disease characterized by excess steroid levels, or by excess activity due to steroids. Methods disclosed herein also include methods of treating a disease that may be treated by reducing or blocking the action of steroids, such as steroid hormones. In embodiments, the disease is characterized by excess cortisol levels, such as, e.g., Cushing's syndrome, and in particular, Cushing's Disease. (As noted above, both Cushing's syndrome and Cushing's Disease are characterized by excess cortisol; Cushing's Disease falls within the definition of Cushing's syndrome as a particular type or example of Cushing's syndrome; thus, all discussion and disclosure regarding Cushing's syndrome includes Cushing's Disease.) Methods disclosed herein also include methods of treating cancer and cancerous tumors, such as hormone-sensitive cancers including prostate cancer, comprising concomitant administration of a GRM and a steroidogenesis inhibitor such as ketoconazole to provide thereby beneficial therapeutic effects. Methods, compositions, and kits disclosed herein are related to the methods compositions, and kits and compositions disclosed in U.S. Provisional Patent Application Ser. No. 62/465,772, filed Mar. 1, 2017, and U.S. Provisional Patent Application Ser. No. 62/466,867, filed Mar. 3, 2017, which applications are hereby incorporated by reference in their entireties.

For example, the present methods include concomitantly administering to a patient a CYP3A inhibitor and a glucocorticoid receptor modulator (GRM), such as a glucocorticoid receptor antagonist (GRA). In embodiments, the CYP3A inhibitor is ketoconazole or itraconazole. In embodiments, the CYP3A inhibitor is ketoconazole or itraconazole and the GRA is mifepristone. In embodiments, the patient is receiving a CYP3A inhibitor (such as, e.g., ketoconazole or itraconazole) and is concomitantly administered an amount of a GRM (such as, e.g., mifepristone) effective to treat Cushing's syndrome, e.g., effective to control hyperglycemia secondary to hypercortisolism in an adult patient suffering from endogenous Cushing's syndrome. In embodiments, the adult patient suffering from endogenous Cushing's syndrome has type 2 diabetes mellitis or glucose intolerance. In embodiments, the adult patient suffering from endogenous Cushing's syndrome has failed surgery or is not a candidate for surgery (e.g., referring to surgical treatment for Cushing's syndrome). In embodiments, the adult patient suffering from endogenous Cushing's syndrome has type 2 diabetes mellitis or glucose intolerance and has failed surgery or is not a candidate for surgery (e.g., referring to surgical treatment for Cushing's syndrome).

In embodiments, the present methods include methods for treating Cushing's syndrome in a patient taking a GRM, comprising reducing the daily dosage amount of the GRM from an original GRM dose to an adjusted GRM dose when the patient is receiving concomitant administration of a CYP3A inhibitor. In embodiments, the adjusted dose of GRM is at least 20% less than the original dose. In embodiments, the adjusted dose of GRM is at least 25% less than the original dose. In embodiments, the adjusted dose of GRM is at least 33% less than the original dose. In embodiments, the adjusted dose of GRM is less than the original dose by a fraction of the original dose selected from 10%, 20%, 25%, 30%, 33%, $33^{1/3}$%, and 50%. In embodiments, the GRM is mifepristone, and the adjusted mifepristone dose is selected from 300 mg per day, 600 mg per day, and 900 mg per day. In embodiments, the CYP3A inhibitor is ketoconazole or itraconazole. In embodiments, the CYP3A inhibitor is ketoconazole and the GRM is mifepristone. In embodiments, the patient is receiving a CYP3A inhibitor (such as, e.g., ketoconazole or itraconazole) and is concomitantly administered an amount of a GRM (such as, e.g., mifepristone) effective to treat Cushing's syndrome, e.g., effective to control hyperglycemia secondary to hypercortisolism in an adult patient suffering from endogenous Cushing's syndrome. In embodiments, the adult patient suffering from endogenous Cushing's syndrome has type 2 diabetes mellitis or glucose intolerance. In embodiments, the adult patient suffering from endogenous Cushing's syndrome has failed surgery or is not a candidate for surgery (e.g., referring to surgical treatment for Cushing's syndrome). In embodiments, the adult patient suffering from endogenous Cushing's syndrome has type 2 diabetes mellitis or glucose intolerance and has failed surgery or is not a candidate for surgery (e.g., referring to surgical treatment for Cushing's syndrome).

For example, the present disclosed methods include administering to a patient receiving ketoconazole or itraconazole an effective amount of a GRM, such as a GRA. In embodiments, the patient is receiving ketoconazole. In embodiments, the patient is receiving ketoconazole and the GRM is mifepristone. In embodiments, the patient is receiving ketoconazole and is administered an amount of mifepristone effective to reduce the effect of a steroid such as cortisol in the patient. In embodiments, the patient is receiving itraconazole. In embodiments, the patient is receiving itraconazole and the GRM is mifepristone. In embodiments, the patient is receiving itraconazole and is administered an amount of mifepristone effective to reduce the effect of a steroid such as cortisol in the patient.

Thus, in embodiments, the methods disclosed herein include a method for treating a patient who is receiving ketoconazole or itraconazole treatment for excess steroid levels, said ketoconazole treatment comprising administering an original dose of ketoconazole or itraconazole to said patient, said method comprising: administering a GRM to the patient receiving ketoconazole or itraconazole, whereby the patient receiving ketoconazole or itraconazole is administered a GRM for treating excess steroid levels. In embodiments, the GRM is mifepristone. In embodiments, the disease is Cushing's syndrome. In embodiments, the disease is Cushing's Disease.

Thus, in embodiments, the methods disclosed herein include a method for treating a patient who is receiving ketoconazole treatment to reduce or block the effects of steroids, said ketoconazole treatment comprising administering an original dose of ketoconazole or itraconazole to said patient, said method comprising: administering a GRM to the patient receiving ketoconazole or itraconazole, whereby the patient receiving ketoconazole or itraconazole is administered a GRM for treating the effects of steroids in the patient. In embodiments, the GRM is mifepristone. In embodiments, the effects of steroids include hypercortisolemic effects, such as the effects of Cushing's syndrome. In embodiments, the effects of steroids include hormonal effects, such as effects on hormone-sensitive cancer.

Applicant further discloses a method for treating a Cushing's syndrome patient who is receiving ketoconzole or itraconazole treatment, said ketoconzole or itraconazole treatment comprising administering an original dose of ketoconzole or itraconazole to said patient, said method comprising: administering a GRM to the patient receiving ketoconzole or itraconazole, wherein the amount of GRM administered is a first dose of GRM, whereby the patient receiving ketoconzole or itraconazole is administered a GRM for treating Cushing's syndrome. In embodiments, the GRM is mifepristone. In embodiments, the or Cushing's syndrome patient suffers from Cushing's Disease.

For example, the present disclosed methods include concomitantly administering to a patient in need thereof, a) an effective amount of a GRM, such as a GRA, and b) an effective amount of a CYP3A inhibitor, such as ketoconazole or itraconazole, or a steroidogenesis inhibitor such as ketoconazole, thereby reducing the effect, the amount, or both, of steroids such as cortisol in the patient. For example, a Cushing's syndrome patient may be in need of reducing their blood levels of cortisol, or may be in need of reducing the effect of cortisol in the patient. For example, a cancer patient may be in need of reducing their blood levels of a steroid, such as an androgen, a progestogen, an estrogen, or other steroid.

Thus, in embodiments of the methods disclosed herein, a subject currently receiving ketoconazole or itraconazole is administered a GRM. In embodiments of the methods disclosed herein, a subject currently receiving ketoconazole or itraconazole as treatment for a condition characterized by excess steroid levels, or as treatment of a condition that is treated by reducing steroid levels or by reducing steroid effects, is administered a GRM, whereby the subject is treated for that condition. In embodiments, the condition is characterized by excessive cortisol levels. In embodiments, the condition is Cushing's syndrome. In embodiments, the condition is a cancer characterized by the deleterious action of steroid hormones on cells, such as cancer cells; the cancer may be hormone-sensitive cancer that may be treated by lowering the levels of a steroid in the patient. In embodiments, the hormone sensitive cancer is prostate cancer, breast cancer, or ovarian cancer.

Accordingly, Applicant discloses herein a method for treating a patient in need of reduced steroid levels, the patient receiving an original dose of ketoconazole or itraconazole, said method comprising:
administering a first dose of a glucocorticoid receptor modulator (GRM) to the patient, wherein said first GRM dose is administered concomitantly with said dose of ketoconazole or itraconazole, whereby the patient is administered both an original dose of ketoconazole or itraconazole and a first dose of a GRM for reducing steroid levels in the patient. In embodiments of such methods, wherein said first dose of GRM comprises an amount of the GRM that is effective to aid in reducing steroid levels in the patient without substantially increasing the level of ketoconazole or itraconazole in the blood of the patient above that level produced by the original dose of ketoconazole, whereby the patient is administered ketoconazole or itraconazole and an effective dose of a GRM and is not exposed to increased risk of ketoconazole or itraconazole toxicity.

Accordingly, Applicant discloses herein a method for treating a patient suffering from excess steroid levels, the patient receiving an original dose of ketoconazole or itraconazole, said method comprising:
administering a first dose of a glucocorticoid receptor modulator (GRM) to the patient, wherein said first GRM dose is administered concomitantly with said dose of ketoconazole or itraconazole, whereby the patient is administered an original dose of ketoconazole or itraconazole and a first dose of a GRM for reducing steroid levels or effects in the patient. In embodiments of such methods, wherein said first dose of GRM comprises an amount of the GRM that is effective to aid in reducing steroid levels or effects in the patient without substantially increasing the level of ketoconazole or itraconazole in the blood of the patient above that level produced by the original dose of ketoconazole or itraconazole, whereby the patient is administered ketoconazole or itraconazole and an effective dose of a GRM and is not exposed to increased risk of ketoconazole or itraconazole toxicity. In embodiments, the excess steroid comprises excess androgen. In embodiments, the excess steroid comprises excess progestogen. In embodiments, the excess steroid comprises excess estrogen. In embodiments, the excess steroid comprises excess cortisol.

Accordingly, in further embodiments, Applicant discloses herein methods for treating a Cushing's syndrome patient, the patient receiving an original dose of ketoconazole or itraconazole, said methods comprising:
administering a first dose of a glucocorticoid receptor modulator (GRM) to the patient, wherein said first GRM dose is administered concomitantly with said dose of ketoconazole or itraconazole, whereby the patient is administered an original dose of ketoconazole or itraconazole and a first dose of a GRM for treating Cushing's syndrome. In embodiments of such methods, wherein said first dose of GRM comprises an amount of the GRM that is effective to aid in the treatment of Cushing's syndrome without substantially increasing the level of ketoconazole or itraconazole in the blood of the patient above that level produced by the original dose of ketoconazole or itraconazole, whereby the patient is administered ketoconazole or itraconazole and an effective dose of a GRM and is not exposed to increased risk of ketoconazole or itraconazole toxicity.

In embodiments, Applicant discloses methods for treating a Cushing's syndrome patient who is receiving ketoconazole or itraconazole treatment, said ketoconazole or itraconazole treatment comprising administering an original dose of ketoconazole or itraconazole to said patient, said method comprising: administering said original dose of ketoconazole or itraconazole to said patient; and administering a first dose of a glucocorticoid receptor modulator (GRM) to the patient, wherein said first dose of GRM comprises an amount of said GRM that is effective to aid in the treatment of Cushing's syndrome without substantially increasing the level of ketoconazole or itraconazole in the blood of the patient above that level produced by the original dose of ketoconazole or itraconazole, whereby the patient is administered ketoconazole or itraconazole and a GRM for treating Cushing's syndrome and is not exposed to increased risk of ketoconazole or itraconazole toxicity. In embodiments, said GRM is mifepristone. In embodiments, the original dose of ketoconazole or itraconazole and the first dose of GRM are administered within a short time of each other. In embodiments, the original dose of ketoconazole or itraconazole and the first dose of GRM are administered at substantially the same time. In embodiments, the original dose of ketoconazole or itraconazole and the first dose of GRM are administered concomitantly. In embodiments, the GRM is mifepristone.

Thus, in embodiments of these methods, administration of the ketoconazole or itraconazole and of the GRM comprises concomitant administration of the original dose of ketoconazole or itraconazole and the first dose of the GRM. In embodiments of concomitant administration, ketoconazole or itraconazole and the GRM are administered to the subject simultaneously. Such concomitant administration of a GRM may be by oral administration; by intravenous administration; subcutaneous administration; parenteral administration; intra-arterial administration; nasal administration; topical administration; or by other routes of administration, or combinations thereof.

In embodiments of the methods disclosed herein, ketoconazole or itraconazole and the GRM are administered to the patient in a single pill containing both the ketoconazole or itraconazole and the GRM, or are administered in a single liquid formulation containing both the ketoconazole or itraconazole and the GRM. In embodiments, the GRM is mifepristone.

In embodiments of the methods disclosed herein, the first dose of the GRM is a dose selected from about 25 milligrams (mg), about 50 mg, about 100 mg, about 200 mg, about 300 mg, about 400 mg, about 500 mg, about 600 mg, about 900 mg, about 1000 mg, about 1200 mg, about 1500 mg, about 1800 mg, and about 2000 mg. In embodiments, the dose of the GRM is a dose of mifepristone selected from about 300 mg, about 600 mg, about 900 mg, about 1200 mg, and about 1500 mg. In embodiments of the methods disclosed herein, the first dose of the GRM is a dose greater than 800 mg of the GRM per day. In embodiments of the methods disclosed herein, the GRM is mifepristone, and the first dose of mifepristone is a dose greater than 800 mg of mifepristone per day.

The methods disclosed herein include repeated administration of a GRM to a patient in need of treatment, including repeated concomitant administration of ketoconazole or itraconazole and a GRM.

For example, in yet further embodiments, a second dose of GRM is administered, wherein said second dose is administered after the administration of the first dose of GRM. The second dose of GRM may comprise about the same amount of said GRM as the first dose of the GRM; may comprise a greater amount of said GRM than the first dose of GRM; or may comprise a smaller amount of GRM than the first dose of GRM. In embodiments of these methods, the GRM is mifepristone.

The methods disclosed herein may further comprise: administering a subsequent dose of ketoconazole or itraconazole and a second dose of GRM, wherein said subsequent dose and said second dose are both administered after the administration of the first dose of the GRM. In embodiments, the second dose of GRM comprises about the same amount of the GRM as the first dose of GRM, and the subsequent dose of ketoconazole or itraconazole comprises about the same amount of ketoconazole or itraconazole as the original dose of ketoconazole or itraconazole. In embodiments, the subsequent dose of ketoconazole or itraconazole comprises a lesser amount of ketoconazole or itraconazole than the amount of the original dose of ketoconazole or itraconazole. In embodiments of these methods, the GRM is mifepristone.

In embodiments, the second dose of GRM comprises a greater amount of the GRM than the amount of said first dose of the GRM. In embodiments, the second dose of GRM comprises a greater amount of the GRM than the amount of said first dose of the GRM, and the subsequent dose of ketoconazole or itraconazole comprises about the same amount of ketoconazole or itraconazole as the original dose of ketoconazole or itraconazole. In embodiments of these methods, the GRM is mifepristone.

In embodiments comprising repeated administration of a GRM to a patient in need of treatment, including repeated concomitant administration of ketoconazole or itraconazole and a GRM, ketoconazole or itraconazole and the GRM may be administered simultaneously. In embodiments of such methods, the GRM may be mifepristone.

In embodiments, ketoconazole or itraconazole and a GRM are administered to the patient in a single pill containing both ketoconazole and the GRM or itraconazole, or in a single liquid formulation containing both ketoconazole or itraconazole and the GRM. In embodiments, the GRM is mifepristone.

Further embodiments of the methods disclosed herein may include further steps, e.g., may comprise administration of a third dose of a GRM, wherein said third dose of the GRM is administered after the administration of the second dose of the GRM. In embodiments, such a third dose of GRM comprises about the same amount of the GRM as the second dose of the GRM. In embodiments, such a third dose of GRM comprises a greater amount of the GRM than the second dose of the GRM. In embodiments, such a third dose of GRM is administered after the administration of the second dose of the GRM. In embodiments, such a third dose of GRM comprises about the same amount of GRM as the amount of said second dose of the GRM. In embodiments, such a third dose of GRM comprises a lesser amount of the GRM than the amount of said second dose of the GRM. In embodiments, such a third dose of GRA comprises a greater amount of the GRM than the amount of said second dose of the GRM. In such embodiments, the GRM may be mifepristone.

In embodiments, methods disclosed herein comprise concomitant administration of ketoconazole or itraconazole and a third dose of GRM. In embodiments of such concomitant administration, ketoconazole or itraconazole and the GRM are administered to the patient simultaneously. In embodiments of such concomitant administration, ketoconazole or itraconazole and the GRM are administered to the patient in a single pill containing both ketoconazole or itraconazole and the GRM, or in a single liquid formulation containing both ketoconazole or itraconazole and the GRM. In embodiments, the GRM is mifepristone.

Embodiments of the methods disclosed herein comprise treatments for patients suffering from Cushing's syndrome; in embodiments, the Cushing's syndrome patient suffers from Cushing's Disease. Such treatments for Cushing's syndrome comprise concomitant administration of ketoconazole or itraconazole and a GRM to the patient.

In embodiments of methods of treating a Cushing's syndrome patient who is receiving ketoconazole or itraconazole treatment, the methods comprise concomitant treatment of the patient with ketoconazole or itraconazole and with a glucocorticoid receptor modulator (GRM). In embodiments of methods of treating a Cushing's syndrome patient who is receiving ketoconazole or itraconazole treatment, the methods comprise concomitant treatment of the patient with ketoconazole or itraconazole and a GRM, wherein the dose of ketoconazole or itraconazole administered concomitantly with the GRM is not reduced with respect to the ketoconazole or itraconazole dose administered to the patient in the absence of concomitant treatment with ketoconazole or itraconazole and a GRM. In embodiments of methods of treating a Cushing's syndrome patient who is receiving ketoconazole or itraconazole treatment, the methods comprise concomitant treatment of the patient with a GRM and ketoconazole or itraconazole. In embodiments, the GRM is mifepristone.

Applicant discloses herein methods for treating a Cushing's syndrome patient, the patient receiving an original dose of ketoconazole or itraconazole, said method comprising: administering a first dose of a glucocorticoid receptor modulator (GRM) to the patient, wherein said first GRM dose is administered concomitantly with the dose of ketoconazole or itraconazole, whereby the patient is administered both an original dose of ketoconazole or itraconazole and a first dose of a GRM for treating Cushing's syndrome. In embodiments, the patient suffers from Cushing's Disease.

In embodiments, Applicant discloses herein methods for treating a Cushing's syndrome patient, the patient receiving an original dose of ketoconazole or itraconazole, the method comprising:
administering a first dose of a GRM to the patient, wherein the first GRM dose is administered concomitantly with the dose of ketoconazole or itraconazole, whereby the patient is administered both an original dose of ketoconazole or itraconazole and a first dose of GRM for treating Cushing's syndrome. In embodiments, the patient suffers from Cushing's Disease. In embodiments, the GRM is mifepristone.

In further embodiments of such methods, wherein said first dose of a GRM comprises a GRM amount that is effective to aid in the treatment of Cushing's syndrome without substantially increasing the level of ketoconazole or itraconazole in the blood of the patient above that level produced by said original dose of ketoconazole or itraconazole, whereby the patient is administered both ketoconazole or itraconazole and an effective dose of a GRM and is not exposed to increased risk of ketoconazole or itraconazole toxicity. In embodiments, administration of ketoconazole or itraconazole and of the GRM comprises concomitant administration of the original dose of ketoconazole or itraconazole and the first dose of the GRM. In embodiments, administering a GRM comprises oral administration of the GRM. In embodiments, ketoconazole or itraconazole and the GRM are administered to the patient simultaneously. In embodiments, ketoconazole or itraconazole and the GRM are administered to the patient in a single pill containing both ketoconazole or itraconazole and the GRM, or in a single liquid formulation containing both ketoconazole or itraconazole and the GRM. In embodiments, the GRM is mifepristone.

In embodiments of the methods disclosed herein, the first dose of the GRM is selected from about 25 mg, about 50 mg, about 100 mg, about 200 mg, about 300 mg, about 400 mg, about 500 mg, about 600 mg, about 900 mg, about 1000 mg, about 1200 mg, about 1500 mg, about 1800 mg, about 2000 mg, about 2100 mg, about 2400 mg, about 2700 mg, and about 3000 mg. In embodiments of the methods disclosed herein, the first dose of the GRM is a dose greater than 800 mg of the GRM per day. In embodiments of the methods disclosed herein, the first dose of the GRM is a dose of mifepristone selected from about 1500 mg mifepristone, about 1200 mg mifepristone, about 900 mg mifepristone, about 600 mg mifepristone, and about 300 mg mifepristone. In embodiments of the methods disclosed herein, the GRM is mifepristone, and the first dose of mifepristone is a dose greater than 800 mg of mifepristone per day.

Further embodiments of the methods disclosed herein comprise administering a second dose of GRM, wherein said second dose is administered after the administration of the first dose of GRM. In embodiments, the second dose of GRM comprises about the same amount of said GRM as the first dose of the GRM. In embodiments, the second dose of GRM comprises a greater amount of said GRM than the first dose of GRM. In embodiments, the GRM is mifepristone.

Further embodiments of the methods disclosed herein comprise administering a subsequent dose of ketoconazole or itraconazole and a second dose of GRM, wherein the subsequent ketoconazole or itraconazole dose and the second GRM dose are both administered after the administration of the first dose of the GRM. In embodiments, the second dose of GRM comprises about the same amount of the GRM as the first dose of the GRM, and the subsequent dose of ketoconazole or itraconazole comprises about the same amount of ketoconazole or itraconazole as the original dose of ketoconazole or itraconazole. In embodiments, the subsequent dose of ketoconazole or itraconazole comprises a lesser amount of ketoconazole or itraconazole than the amount of the original dose of ketoconazole or itraconazole. In embodiments, the second dose of GRM comprises a greater amount of the GRM than the amount of said first dose of the GRM. In embodiments, the second dose of GRA comprises a greater amount of the GRM than the amount of the first dose of the GRM, and the subsequent dose of ketoconazole or itraconazole comprises about the same amount of ketoconazole or itraconazole as the original dose of ketoconazole or itraconazole. In embodiments, the GRM is mifepristone.

In embodiments, ketoconazole or itraconazole and the GRM are administered to the patient simultaneously. In embodiments, ketoconazole or itraconazole and mifepristone are administered to the patient simultaneously. In embodiments, ketoconazole or itraconazole and the GRM are administered to the patient in a single pill containing both ketoconazole or itraconazole and the GRM, or in a single liquid formulation containing both ketoconazole or itraconazole and the GRM. In embodiments, ketoconazole or itraconazole and mifepristone are administered to the patient simultaneously. In embodiments, ketoconazole or itraconazole and mifepristone are administered to the patient in a single pill comprising both ketoconazole or itraconazole and mifepristone, or in a single liquid formulation comprising both ketoconazole or itraconazole and mifepristone.

Embodiments of the methods disclosed herein further comprise administration of a third dose of GRM, wherein said third dose of the GRM is administered after the administration of the second dose of the GRM. In embodiments, the third dose of GRM comprises about the same amount of the GRM as the second dose of the GRM. In embodiments, the third dose of GRM comprises a greater amount of the GRM than the second dose of the GRM. In embodiments, the methods further comprise administration of a third dose of GRM, wherein the third dose of the GRM is administered after the administration of the second dose of the GRM. In embodiments, the third dose of GRM comprises about the same amount of GRM as the amount of said second dose of the GRM. In embodiments, the third dose of the GRM comprises a lesser amount of the GRM than the amount of said second dose of the GRM. In embodiments, the third dose of GRM comprises a greater amount of the GRM than the amount of said second dose of the GRM. In embodiments, administration of the third GRM dose comprises concomitant administration ketoconazole and the third dose of GRM. In such embodiments, ketoconazole and the GRM are administered to the patient simultaneously. In embodiments of the methods comprising such third dose of GRM, ketoconazole and the GRM are administered to the patient in a single pill containing both ketoconazole and the GRM, or in a single liquid formulation containing both ketoconazole and the GRM. In embodiments, the GRM is mifepristone.

Applicant discloses herein methods for treating Cushing's syndrome patients with a GRM (such as mifepristone) and ketoconazole or itraconazole. In embodiments, the patient suffers from Cushing's Disease.

Applicant discloses here methods for treating a Cushing's syndrome patient who is receiving ketoconazole or itraconazole treatment, said ketoconazole or itraconazole treatment comprising administering an original dose of ketoconazole or itraconazole to said patient, said method comprising: administering said original dose of ketoconazole or itraconazole to said patient; and administering a glucocorticoid receptor modulator (GRM) to the patient, wherein the amount of GRM administered is a first dose of GRM, whereby the patient is administered both ketoconazole or itraconazole and a GRM for treating Cushing's syndrome. In embodiments, the first dose of GRM is a lesser amount of GRM than would be administered in the absence of ketoconazole or itraconazole. In embodiments, the GRM is mifepristone.

In embodiments of such methods of treating a Cushing's syndrome patient who is receiving ketoconazole or itraconazole treatment, the first dose of GRM comprises an amount of GRM that is effective to aid in the treatment of Cushing's syndrome without substantially increasing the level of ketoconazole or itraconazole in the blood of the patient above that level produced by said original dose of ketoconazole or itraconazole, whereby the patient is administered both ketoconazole or itraconazole and an effective dose of a GRM and is not exposed to increased risk of ketoconazole or itraconazole toxicity. In embodiments, the first dose of GRM is a lesser amount of GRM than would be administered in the absence of ketoconazole or itraconazole. In embodiments, the GRM is mifepristone.

In embodiments of methods of treating a Cushing's syndrome patient who is receiving ketoconazole treatment, the administration of ketoconazole or itraconazole and of the GRM comprises concomitant administration of the original dose of ketoconazole or itraconazole and the first dose of said GRM. In embodiments of methods of treating a Cushing's syndrome patient who is receiving ketoconazole or itraconazole treatment, the administration of the GRM comprises oral administration of the GRM. In embodiments of methods of treating a Cushing's syndrome patient who is receiving ketoconazole or itraconazole treatment, the ketoconazole or itraconazole and the GRM are administered to the patient simultaneously. In embodiments of methods of treating a Cushing's syndrome patient who is receiving ketoconazole or itraconazole treatment, the ketoconazole or itraconazole and the GRM are administered to the patient in a single pill containing both ketoconazole or itraconazole and the GRM. In embodiments of methods of treating a Cushing's syndrome patient who is receiving ketoconazole or itraconazole treatment, ketoconazole or itraconazole and mifepristone are administered in a single liquid formulation comprising ketoconazole or itraconazole and mifepristone.

In embodiments of methods of treating a Cushing's syndrome patient who is receiving ketoconazole or itraconazole treatment, the first dose of the GRM is a dose of GRM selected from about 25 mg, about 50 mg, about 100 mg, about 200 mg, about 300 mg, about 400 mg, about 500 mg, about 600 mg, about 900 mg, about 1000 mg, about 1200 mg, about 1500 mg, about 1800 mg, about 2000 mg, about 2100 mg, about 2400 mg, about 2700 mg, and about 3000 mg. In embodiments of the methods disclosed herein, the first dose of the GRM is a dose greater than 800 mg of the GRM per day. In embodiments, the GRM is mifepristone, and the first dose of the GRM is a dose of mifepristone selected from about 1500 mg mifepristone, about 1200 mg mifepristone, about 900 mg mifepristone, about 600 mg mifepristone, and about 300 mg mifepristone. In embodiments of the methods disclosed herein, the GRM is mifepristone, and the first dose of mifepristone is a dose greater than 800 mg of mifepristone per day.

In embodiments of methods of treating a Cushing's syndrome patient who is receiving ketoconazole or itraconazole treatment, the methods further comprise: administering a second dose of GRM, wherein said second dose is administered after the administration of the first dose of said GRM. In embodiments of methods of treating a Cushing's syndrome patient who is receiving ketoconazole or itraconazole treatment, the second dose of GRM comprises about the same amount of said GRM as the first dose of the GRM. In embodiments of methods of treating a Cushing's syndrome patient who is receiving ketoconazole or itraconazole treatment, the second dose of GRM comprises a lesser amount of said GRM than the first dose of GRM. In embodiments, the second dose of GRM is a lesser amount of GRM than would be administered in the absence of ketoconazole or itraconazole. In embodiments of methods of treating a Cushing's syndrome patient who is receiving ketoconazole or itraconazole treatment, the second dose of GRM comprises a greater amount of said GRM than the first dose of GRM. In embodiments, the GRM is mifepristone.

In embodiments of methods of treating a Cushing's syndrome patient who is receiving ketoconazole or itraconazole treatment, the methods further comprise: administering a subsequent dose of ketoconazole or itraconazole and a second dose of GRM, wherein the subsequent ketoconazole or itraconazole dose and the second GRM dose are both administered after the administration of the first dose of the GRM. In embodiments of methods of treating a Cushing's syndrome patient who is receiving ketoconazole or itraconazole treatment, the second dose of the GRM comprises about the same amount of the GRM as the first dose of the GRM, and the subsequent dose of ketoconazole or itraconazole comprises about the same amount of ketoconazole or itraconazole as the original dose of ketoconazole or itraconazole. In embodiments, the second dose of GRM is a lesser amount of GRM than would be administered in the absence of ketoconazole or itraconazole.

In embodiments of methods of treating a Cushing's syndrome patient who is receiving ketoconazole or itraconazole treatment, the subsequent dose of ketoconazole or itraconazole comprises a lesser amount of ketoconazole or itraconazole than the amount of the original dose of ketoconazole or itraconazole. In embodiments of methods of treating a Cushing's syndrome patient who is receiving ketoconazole or itraconazole treatment, the second dose of the GRM comprises a greater amount of the GRM than the amount of said first dose of the GRM. In embodiments of methods of treating a Cushing's syndrome patient who is receiving ketoconazole or itraconazole treatment, the second dose of the GRM comprises a greater amount of the GRM than the amount of said first dose of the GRM, and said subsequent dose of ketoconazole or itraconazole comprises about the same amount of ketoconazole or itraconazole as the original dose of ketoconazole or itraconazole. In embodiments of methods of treating a Cushing's syndrome patient who is receiving ketoconazole or itraconazole treatment, the ketoconazole or itraconazole and the GRM are administered to the patient simultaneously. In embodiments of methods of treating a Cushing's syndrome patient who is receiving ketoconazole or itraconazole treatment, the ketoconazole or itraconazole and the GRM are administered to the patient in a single pill containing both ketoconazole or itraconazole and the GRM, or in a single liquid formulation comprising ketoconazole or itraconazole and the GRM. In embodiments of methods of treating a Cushing's syndrome patient who is receiving ketoconazole or itraconazole treatment, the GRM is mifepristone, and the ketoconazole or itraconazole and the mifepristone are administered to the patient in a single pill comprising both ketoconazole or itraconazole and mifepristone, or in a single liquid formulation comprising ketoconazole or itraconazole and mifepristone.

In embodiments of methods of treating a Cushing's syndrome patient who is receiving ketoconazole or itraconazole treatment, the methods further comprise: administration of a third dose of the GRM, wherein the third dose of the GRM is administered after the administration of the second dose of the GRM. In embodiments, the third dose of GRM is a lesser amount of GRM than would be administered in the absence of ketoconazole. In such embodiments of methods of treating a Cushing's syndrome patient who is receiving ketoconazole or itraconazole treatment, the third dose of GRM comprises about the same amount of the GRM as the second dose of the GRM. In such embodiments of methods of treating a Cushing's syndrome patient who is receiving ketoconazole or itraconazole treatment, the third dose of the GRM comprises a greater amount of the GRM than the second dose of the GRM. In such embodiments of methods of treating a Cushing's syndrome patient who is receiving ketoconazole or itraconazole treatment, the third dose of the GRM is administered after the administration of the second dose of the GRM. In such embodiments of methods of treating a Cushing's syndrome patient who is receiving ketoconazole or itraconazole treatment, the third dose of the GRM comprises about the same amount of GRM as the amount of said second dose of the GRM. In such embodiments of methods of treating a Cushing's syndrome patient who is receiving ketoconazole or itraconazole treatment, the third dose of the GRM comprises a lesser amount of the GRM than the amount of said second dose of the GRM. In such embodiments of methods of treating a Cushing's syndrome patient who is receiving ketoconazole treatment, the third dose of the GRM comprises a greater amount of the GRM than the amount of said second dose of the GRM. In embodiments, the GRM is mifepristone.

In such embodiments of methods of treating a Cushing's syndrome patient who is receiving ketoconazole or itraconazole treatment, the methods comprise concomitant administration of ketoconazole or itraconazole and of the third dose of the GRM. In embodiments of methods of treating a Cushing's syndrome patient who is receiving ketoconazole or itraconazole treatment, the ketoconazole or itraconazole and the GRM are administered to the patient simultaneously. In embodiments of methods of treating a Cushing's syndrome patient who is receiving ketoconazole or itraconazole treatment, the ketoconazole or itraconazole and the GRM are administered to the patient in a single pill containing both ketoconazole or itraconazole and the GRM, or in a single liquid formulation comprising ketoconazole or itraconazole and the GRM. In embodiments of methods of treating a Cushing's syndrome patient who is receiving ketoconazole or itraconazole treatment, the GRM is mifepristone, and the ketoconazole or itraconazole and the mifepristone are administered to the patient in a single pill comprising both ketoconazole or itraconazole and mifepristone, or in a single liquid formulation comprising ketoconazole or itraconazole and mifepristone.

In embodiments of methods of treating a Cushing's syndrome patient who is receiving ketoconazole or itraconazole treatment, the methods comprise concomitant treatment of the patient with mifepristone and ketoconazole or itraconazole. In embodiments of methods of treating a Cushing's syndrome patient who is receiving ketoconazole or itraconazole treatment, the methods comprise concomitant treatment of the patient with mifepristone and ketoconazole or itraconazole, wherein the dose of ketoconazole or itraconazole administered concomitantly with mifepristone is not reduced with respect to the ketoconazole or itraconazole dose administered to the patient in the absence of concomitant treatment with ketoconazole and mifepristone.

Applicant discloses herein a method for treating a Cushing's syndrome patient who is receiving ketoconazole or itraconazole treatment, said ketoconazole or itraconazole treatment comprising administering an original dose of ketoconazole or itraconazole to said patient, said method comprising: administering said original dose of ketoconazole or itraconazole to said patient; and administering mifepristone to the patient, wherein the amount of mifepristone administered is a first dose of mifepristone, whereby the patient is administered both ketoconazole or itraconazole and mifepristone for treating Cushing's syndrome. In embodiments, the first dose of mifepristone is a lesser amount of mifepristone than would be administered in the absence of ketoconazole or itraconazole.

In embodiments of methods for treating a Cushing's syndrome patient who is receiving ketoconazole or itraconazole treatment, wherein the ketoconazole or itraconazole treatment comprises administering an original dose of ketoconazole or itraconazole to said patient, the methods comprise administering a first dose of mifepristone that comprises an amount of mifepristone that is effective to aid in the treatment of Cushing's syndrome without substantially increasing the level of ketoconazole or itraconazole in the blood of the patient above that level produced by said original dose of ketoconazole or itraconazole, whereby the patient is administered both ketoconazole or itraconazole and an effective dose of mifepristone and is not exposed to increased risk of ketoconazole or itraconazole toxicity. In embodiments of such methods, the administration of ketoconazole or itraconazole and of mifepristone comprises concomitant administration of the original dose of ketoconazole or itraconazole and of the first dose of mifepristone. In embodiments of such methods, the administration of mifepristone comprises oral administration of mifepristone. In embodiments of such methods, ketoconazole or itraconazole and mifepristone are administered to the patient simultaneously. In embodiments of such methods, ketoconazole or itraconazole and mifepristone are administered to the patient in a single pill comprising both ketoconazole or itraconazole and mifepristone, or in a single liquid formulation comprising ketoconazole or itraconazole and mifepristone. In embodiments of such methods, the first dose of mifepristone is a dose of about 300 milligrams (mg), about 600 mg, about 900 mg, about 1200 mg, or about 1500 mg. In embodiments of the methods disclosed herein, the first dose of mifepristone is a dose greater than 800 mg of mifepristone per day.

In embodiments, such methods further comprise: administering a second dose of mifepristone, wherein said second dose is administered after the administration of the first dose of mifepristone. In embodiments, the second dose of mifepristone is a lesser amount of mifepristone than would be administered in the absence of ketoconazole or itraconazole. In embodiments of such methods, the second dose of mifepristone comprises about the same amount of mifepristone as the first dose of mifepristone. In embodiments of such methods, the second dose of mifepristone comprises a greater amount of mifepristone than the first dose of mifepristone. In embodiments, such methods further comprise administering a subsequent dose of ketoconazole or itraconazole and a second dose of mifepristone, wherein said subsequent dose and said second dose are both administered after the administration of the first dose of mifepristone. In embodiments of such methods, the second dose of mifepristone is a lesser amount of mifepristone than would be administered in the absence of ketoconazole or itraconazole. In embodiments of such methods, the second dose of mifepristone comprises about the same amount of mifepristone as the first dose of mifepristone, and said subsequent dose of ketoconazole or itraconazole comprises about the same amount of ketoconazole or itraconazole as the original dose of ketoconazole or itraconazole. In embodiments of such methods, the subsequent dose of ketoconazole or itraconazole comprises a lesser amount of ketoconazole or itraconazole than the amount of the original dose of ketoconazole or itraconazole. In embodiments of such methods, the second dose of mifepristone comprises a greater amount of mifepristone than the amount of said first dose of mifepristone. In embodiments of such methods, the second dose of mifepristone comprises a greater amount of mifepristone than the amount of said first dose of mifepristone, and said subsequent dose of ketoconazole or itraconazole comprises about the same amount of ketoconazole or itraconazole as the original dose of ketoconazole or itraconazole. In embodiments of such methods, ketoconazole or itraconazole and mifepristone are administered to the patient simultaneously. In embodiments of such methods, ketoconazole or itraconazole and mifepristone are administered to the patient in a single pill comprising both ketoconazole or itraconazole and mifepristone, or in a single liquid formulation comprising ketoconazole or itraconazole and mifepristone.

In embodiments, such methods further comprise administration of a third dose of mifepristone, wherein said third dose of mifepristone is administered after the administration of the second dose of mifepristone. In embodiments, the third dose of mifepristone is a lesser amount of mifepristone than would be administered in the absence of ketoconazole or itraconazole. In embodiments of such methods, the third dose of mifepristone comprises about the same amount of mifepristone as the second dose of mifepristone. In embodiments of such methods, the third dose of mifepristone comprises a greater amount of mifepristone than the second dose of mifepristone. In embodiments, such methods further comprise administration of a third dose of mifepristone, wherein said third dose of mifepristone is administered after the administration of the second dose of mifepristone. In embodiments of such methods, the third dose of mifepristone comprises about the same amount of mifepristone as the amount of said second dose of mifepristone. In embodiments of such methods, the third dose of mifepristone comprises a lesser amount of mifepristone than the amount of said second dose of mifepristone. In embodiments of such methods, the third dose of mifepristone comprises a greater amount of mifepristone than the amount of said second dose of mifepristone. In embodiments, such methods comprise concomitant administration of ketoconazole or itraconazole and of the third dose of mifepristone. In embodiments of such methods, ketoconazole or itraconazole and mifepristone are administered to the patient simultaneously. In embodiments of such methods, ketoconazole or itraconazole and mifepristone are administered to the patient in a single pill comprising both ketoconazole or itraconazole and mifepristone, or in a single liquid formulation comprising ketoconazole or itraconazole and mifepristone.

In embodiments of methods for treating a Cushing's syndrome patient who is receiving ketoconazole or itraconazole treatment at an original dose of ketoconazole or itraconazole, the methods comprise administering a first dose of mifepristone to the subject and reducing the dose of ketoconazole or itraconazole received by the patient to a ketoconazole or itraconazole dose that is less than the original ketoconazole or itraconazole dose, wherein the dose of mifepristone comprises an amount of mifepristone that is effective to aid in the treatment of Cushing's syndrome without substantially increasing the level of ketoconazole or itraconazole in the blood of the patient above that level produced by said original dose of ketoconazole or itraconazole, whereby the patient is administered both ketoconazole or itraconazole and an effective dose of mifepristone and is not exposed to increased risk of ketoconazole or itraconazole toxicity.

Accordingly, Applicant discloses herein a method for treating a Cushing's syndrome patient who is receiving ketoconazole or itraconazole at an initial dosage, said initial dosage comprising administering an initial dose of ketoconazole or itraconazole to said patient, said method comprising: administering a reduced dose of ketoconazole or itraconazole to said patient, wherein said reduced dose of ketoconazole or itraconazole is a dose of ketoconazole or itraconazole that is less than said initial dose by an amount of at least about 5% of the initial dose; and administering mifepristone to the patient, wherein the amount of mifepristone administered is a first dose of mifepristone, whereby the patient is administered both the reduced dose of ketoconazole or itraconazole and the first dose of mifepristone. In embodiments of such methods, the first dose of mifepristone comprises an amount of mifepristone that is effective to aid in the treatment of Cushing's syndrome, whereby the patient is administered both a reduced dose of ketoconazole and an effective dose of mifepristone. In embodiments, the first dose of mifepristone is a lesser amount of mifepristone than would be administered in the absence of ketoconazole. In embodiments of such methods, the administration of ketoconazole or itraconazole and of mifepristone comprises concomitant administration of the reduced dose of ketoconazole or itraconazole and the first dose of mifepristone. In embodiments of such methods, the administration of mifepristone comprises oral administration of mifepristone. In embodiments of such methods, the first dose of ketoconazole or itraconazole is less than said initial dose of ketoconazole or itraconazole by an amount that is about 10%, about 15%, about 25%, about 25%, about 30%, about 35%, about 40%, about 45%, about 50%, about 60%, about 75%, or about 90% less than the initial dose. In embodiments of such methods, the first dose of mifepristone is a dose selected from about 300 mg, about 600 mg, about 900 mg, about 1200 mg, and about 1500 mg.

In embodiments, such methods further comprise administering a second dose of mifepristone, wherein said second dose is administered at a time after the administration of the first dose of mifepristone. In embodiments, the second dose of mifepristone is a lesser amount of mifepristone than would be administered in the absence of ketoconazole. In embodiments of such methods, the second dose of mifepristone comprises a lesser amount of mifepristone than the first dose of mifepristone. In embodiments of such methods, the second dose of mifepristone comprises about the same amount of mifepristone as the first dose of mifepristone. In embodiments of such methods, the second dose of mifepristone comprises a greater amount of mifepristone than the first dose of mifepristone. In embodiments, such methods further comprise administering a subsequent dose of ketoconazole or itraconazole and a second dose of mifepristone, wherein said subsequent dose and said second dose are both administered at a time after the administration of both the reduced dose of ketoconazole or itraconazole and of the first dose of mifepristone. In embodiments of such methods, the second dose of mifepristone comprises about the same amount of mifepristone as the first dose of mifepristone, and said subsequent dose of ketoconazole or itraconazole comprises about the same amount of ketoconazole or itraconazole as the reduced dose of ketoconazole or itraconazole. In embodiments of such methods, the subsequent dose of ketoconazole or itraconazole comprises a lesser amount of ketoconazole or itraconazole than the amount of said reduced dose of ketoconazole or itraconazole. In embodiments of such methods, the second dose of mifepristone comprises a greater amount of mifepristone than the amount of said first dose of mifepristone. In embodiments of such methods, the second dose of mifepristone comprises a greater amount of mifepristone than the amount of said first dose of mifepristone, and said subsequent dose of ketoconazole or itraconazole comprises about the same amount of ketoconazole or itraconazole as the reduced dose of ketoconazole or itraconazole.

In embodiments, such methods further comprise administration of a third dose of mifepristone, wherein said third dose of mifepristone is administered at a time after the administration of the second dose of mifepristone. In embodiments, the third dose of mifepristone is a lesser amount of mifepristone than would be administered in the absence of ketoconazole or itraconazole. In embodiments of such methods, the third dose of mifepristone comprises a lesser amount of mifepristone than the second dose of mifepristone. In embodiments of such methods, the third dose of mifepristone comprises about the same amount of mifepristone as the second dose of mifepristone. In embodiments of such methods, the third dose of mifepristone comprises a greater amount of mifepristone than the second dose of mifepristone.

In embodiments, such methods further comprise administration of a third dose of mifepristone, wherein said third dose of mifepristone is administered at a time after the administration of the second dose of mifepristone. In embodiments, the third dose of mifepristone is a lesser amount of mifepristone than would be administered in the absence of ketoconazole or itraconazole. In embodiments of such methods, the third dose of mifepristone comprises about the same amount of mifepristone as the amount of said second dose of mifepristone. In embodiments of such methods, the third dose of mifepristone comprises a lesser amount of mifepristone than the amount of said second dose of mifepristone. In embodiments of such methods, the third dose of mifepristone comprises a greater amount of mifepristone than the amount of said second dose of mifepristone. In embodiments, such methods comprise administration of a dose of ketoconazole or itraconazole administered at the time as the administration of the third dose of mifepristone.

Applicant further discloses herein methods for treating a patient who is suffering from Cushing's syndrome with mifepristone, the patient also receiving concomitant administration of ketoconazole or itraconazole, said method comprising: to the patient concomitantly receiving ketoconazole or itraconazole, orally administering a dose of mifepristone that is a smaller dose of mifepristone than the dose that is an effective mifepristone dose when the patient receives only mifepristone. An effective dose of mifepristone when the patient receives only mifepristone for treating Cushing's syndrome is termed a "lone dose" of mifepristone. For example, the dose of mifepristone that is effective for the treatment of a Cushing's syndrome patient not concomitantly receiving ketoconazole or other treatment for Cushing's syndrome is a "lone dose" of mifepristone. In embodiments of the methods disclosed herein, for Cushing's syndrome patient receiving concomitant administration of ketoconazole or itraconazole, the dose of mifepristone is reduced by at least about 5% as compared to the lone dose of mifepristone. Accordingly, Applicant discloses herein a method for treating a Cushing's syndrome patient who is receiving ketoconazole or itraconazole, said method comprising: administering a reduced dose of mifepristone to said patient, wherein said reduced dose of mifepristone is a dose of mifepristone that is less than the lone dose of mifepristone as defined herein; whereby the patient is administered both ketoconazole or itraconazole and the reduced dose of mifepristone. In embodiments, such a reduced dose of mifepristone is an amount of mifepristone that is less than the lone dose of mifepristone by an amount that is at least about 5% of the lone dose. In embodiments of such methods, the reduced dose of mifepristone comprises an amount of mifepristone that is effective to aid in the treatment of Cushing's syndrome, whereby the patient is administered both a reduced dose of mifepristone and a dose of ketoconazole or itraconazole. In embodiments of such methods, the administration of ketoconazole or itraconazole and of mifepristone comprises concomitant administration of the reduced dose of mifepristone and the dose of ketoconazole or itraconazole. In embodiments of such methods, the administration of mifepristone comprises oral administration of mifepristone. In embodiments of such methods, the reduced dose of mifepristone is less than said lone dose of mifepristone by an amount that is about 10%, about 15%, about 25%, about 25%, about 30%, about 35%, about 40%, about 45%, about 50%, about 60%, about 75%, or about 90% less than the lone dose. In embodiments of such methods, the reduced dose of mifepristone is a daily dose selected from about 900 mg, greater than 800 mg, about 600 mg, about 300 mg, or is a dose of mifepristone selected from about 300 mg mifepristone administered every other day, a dose of about 300 mg mifepristone administered every third day, and a dose of mifepristone of about 300 mg administered every fourth day.

Compositions

Applicant discloses herein compositions comprising a glucocorticoid receptor modulator (GRM), such as a glucocorticoid receptor antagonist (GRA) such as, e.g., mifepristone, which may be used in the treatment of a patient suffering from excess cortisol, e.g., in a patient suffering from Cushing's syndrome. In embodiments, the compositions comprising a GRM may be provided in an amount effective to control hyperglycemia secondary to hypercortisolism, and may be provided in an amount effective control hyperglycemia secondary to hypercortisolism in a patient suffering from endogenous Cushing's disease. In embodiments, the compositions comprising a GRM may be provided in an amount effective to control hyperglycemia secondary to hypercortisolism in a patient suffering from endogenous Cushing's disease, where the patient has failed surgery, or is not a candidate for surgery.

Applicant also discloses herein compositions comprising a GRM and ketoconazole or itraconazole. These compositions comprising a GRM and ketoconazole or itraconazole may be used in the treatment of a Cushing's syndrome patient.

The compositions as disclosed herein can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions disclosed herein can be administered by inhalation, for example, intranasally. Additionally, the compositions of the present invention can be administered transdermally. The compositions disclosed herein can also be administered by intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995).

In embodiments disclosed herein, the compositions include pharmaceutical compositions including a pharmaceutically acceptable carrier or excipient, a GRM, and a CYP3A inhibitor. CYP3A inhibitors include, for example, strong CYP3A inhibitors such as ketoconazole, itraconazole, nefazodone, ritonavir, nelfinavir, indinavir, atazanavir, amprenavir and fosamprenavir, clarithromycin, conivaptan, lopinavir/ritonavir, posaconazole, saquinavir, telithromycin, and voriconazole. In embodiments disclosed herein, the compositions include pharmaceutical compositions including a pharmaceutically acceptable carrier or excipient, a GRM, and a steroidogenesis inhibitor (SI). SIs include, for example, ketoconazole, levoketoconazole, metyrapone, aminoglutethimide, etomidate, LCI699 (Osilodrostat), and others.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Mack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of ketoconazole or itraconazole and/or the GRM.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain ketoconazole and/or the GRM mixed with a filler or binders such as lactose or starches, lubricants such as talc or magnesium stearate, and, optionally, stabilizers. In soft capsules, ketoconazole and/or the GRM may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and ketoconazole and/or the GRM are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving ketoconazole and/or the GRM in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending ketoconazole and/or the GRA in a vegetable oil, such as *arachis* oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

Administration

The compositions disclosed herein can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the GRM and ketoconazole. In embodiments, the GRM is mifepristone. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The GRM and CYP3A inhibitor or steroidogenesis inhibitor can be co-administered or administered separately The GRM and ketoconazole or itraconazole can be co-administered or administered separately. Concomitant administration includes administering the CYP3A inhibitor or steroidogenesis inhibitor within 0.5, 1, 2, 4, 6, 8, 10, 12, 16, 20, or 24 hours of the GRM. Concomitant administration also includes administering the GRM and the CYP3A inhibitor or steroidogenesis inhibitor simultaneously, approximately simultaneously (e.g., within about 1, 5, 10, 15, 20, or 30 minutes of each other), or sequentially in any order. Moreover, the GRM and the CYP3A inhibitor or steroidogenesis inhibitor can each be administered once a day, or two, three, or more times per day so as to provide the preferred dosage level per day. In embodiments, the GRM is mifepristone.

In some embodiments, concomitant administration can be accomplished by co-formulation, i.e., preparing a single pharmaceutical composition including both the GRM and the CYP3A inhibitor or steroidogenesis inhibitor. Suitable co-formulations include single pharmaceutical compositions including a GRM, the CYP3A inhibitor or steroidogenesis inhibitor, and a pharmaceutically acceptable excipient. In embodiment, the GRM is mifepristone.

In other embodiments, the GRM and the CYP3A inhibitor or steroidogenesis inhibitor can be formulated separately.

The CYP3A inhibitor or steroidogenesis inhibitor can be present in any suitable amount, and can depend on various factors including, but not limited to, weight and age of the subject, state of the disease, etc. Suitable dosage ranges for the CYP3A inhibitor or steroidogenesis inhibitor in combination with the GRM, include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the CYP3A inhibitor or steroidogenesis inhibitor in combination with the GRM, include about 1 mg, 5, 10, 20, 30, 40, 50, 60, 70, 80, 90, 100, 200, 300, 400, 500, 600, 700, 800, 900 or 1000 mg. In embodiments, the GRM is mifepristone.

Similarly, the GRM can be present in combination with the CYP3A inhibitor or steroidogenesis inhibitor in any suitable amount. The amount of GRM can depend on various factors including, but not limited to, weight and age of the subject, state of the disease, etc. Suitable dosage ranges for the GRM in combination with the CYP3A inhibitor or steroidogenesis inhibitor include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the GRM in combination with the CYP3A inhibitor or steroidogenesis inhibitor include, but are not limited to, about 1 mg, 5, 10, 20, 30, 40, 50, 60, 70, 80, 90, 100, 200, 300, 400, 500, 600, 700, 800, 900 or about 1000 mg. In embodiments, the GRM is mifepristone, The CYP3A inhibitor or steroidogenesis inhibitor and the GRM can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The CYP3A inhibitor or steroidogenesis inhibitor and the GRM can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of ketoconazole and the GRM are suitable in the compositions and methods disclosed herein. In embodiments, the GRM is mifepristone.

The composition can also contain other compatible therapeutic agents. The compounds described herein can be used in combination with one another, or with adjunctive agents that may not be effective alone, but may contribute to the efficacy of the active agent.

Kits

Applicant further provides kits including compositions as disclosed herein. Kits may also include instructions for the use of the compositions.

In embodiments, a kit includes: a pharmaceutical composition containing a CYP3A inhibitor or steroidogenesis inhibitor (e.g. ketoconazole or itraconazole) and a pharmaceutical composition containing a GRM. In embodiments, the GRM is mifepristone.

In embodiments, a kit includes: a pharmaceutical composition containing a CYP3A inhibitor or steroidogenesis inhibitor; and a pharmaceutical composition containing a GRM; and instructions for the use (e.g., administration) of the CYP3A inhibitor or steroidogenesis inhibitor and the GRM. In embodiments, the GRM is mifepristone, and the instructions include instructions for the administration of mifepristone. In embodiments, the instructions include instructions regarding one or more of the number of pharmaceutical compositions to be taken each day, the timing of such administration, whether or not the pharmaceuticals are to be taken with food or in a fasted state, contraindications, possible side effects, activities to be avoided during treatment with the pharmaceutical compositions (if any), and foods to be avoided during treatment with the pharmaceutical compositions (if any).

In embodiments, a kit includes: a pharmaceutical composition containing a CYP3A inhibitor or steroidogenesis inhibitor and a GRM. In embodiments, the GRM is mifepristone, and the pharmaceutical composition contains ketoconazole and mifepristone.

In embodiments, a kit includes: a pharmaceutical composition containing a CYP3A inhibitor or steroidogenesis inhibitor and a GRM; and instructions for the use (e.g., administration) of the pharmaceutical composition. In embodiments, the GRM is mifepristone. In embodiments of the kits disclosed herein, the pharmaceutical composition includes CYP3A inhibitor or steroidogenesis inhibitor and mifepristone, and the instructions include instructions for the administration of the pharmaceutical containing a CYP3A inhibitor or a steroidogenesis inhibitor and mifepristone. In embodiments, the instructions include instructions regarding one or more of the number of pharmaceutical compositions to be taken each day, the timing of such administration, whether or not the pharmaceutical composition is to be taken with food or in a fasted state, contraindications, possible side effects, activities to be avoided during treatment with the pharmaceutical composition (if any), and foods to be avoided during treatment with the pharmaceutical composition (if any).

EXAMPLES

The following examples are presented by way of illustration of embodiments of the methods disclosed herein, and serve to illustrate, but not to limit, the present disclosure of methods of treating patients suffering from Cushing's syndrome, including Cushing's Disease; or from prostate cancer and other androgen-sensitive cancers; or from breast cancer, ovarian cancer, or other cancer hormone-sensitive cancer (e.g., cancer sensitive to estrogen or progesterone); and patients suffering from other diseases, disorders, or syndromes.

Example 1

A study was performed in order to determine the effect of oral ketoconazole at a dose of 400 mg once per day (OD) or 200 mg twice per day (BID) on the plasma pharmacokinetics of a 300 mg single dose of mifepristone given to a fasted subject, in comparison to previous study data. This study was an open-label study in healthy male subjects.

Healthy male volunteers between the ages of 18 to 45 years of age with a body mass index (BMI) ranging between 19 and 32 kg/m2 and a weight of at least 60 kg (132 lbs) were enrolled. Subjects had no clinically significant abnormal findings on the physical examination, ECG, blood pressure, heart rate, medical history, or clinical laboratory results during screening. The QTc interval at screening was less than 450 msec.

In cohort 1, six subjects received ketoconazole 400 mg OD for 14 days. The cohort 1 subjects participated in a screening visit to assess eligibility, and in a check-in day during which eligibility was re-confirmed and the first dose of 400 mg oral ketoconazole given at approximately 8 PM (12 hours prior to expected time of Day 1 mifepristone dose).

The morning of Day 1, subjects received 400 mg oral ketoconazole fasted, 0.5 hour prior to receiving the 300 mg single dose of mifepristone fasted. Subjects remained in the clinic on Days 2 and 3 to receive 400 mg OD oral ketoconazole fasted, and for safety evaluation and collection of blood pharmacokinetic (PK) samples. Subjects were discharged from the clinic on Day 4 following administration of 400 mg OD oral ketoconazole fasted, and returned to the clinic the mornings of Days 5 through 13 to receive 400 mg OD oral ketoconazole fasted.

In cohort 2, six subjects received ketoconazole 200 mg BID for 14 days. The 300 mg single dose of mifepristone was given to all subjects on day 1. All 12 subjects completed the study. Cohort 2 subjects participated in a Screening visit to assess eligibility and a check-in Day (Day −1) during which eligibility was re-confirmed. On Day 0, subjects received 200 mg BID oral ketoconazole: the morning dose after an overnight fast and the evening dose 12 hours prior to expected time of Day 1 Mifepristone dose. The morning of Day 1, subjects received 200 mg oral ketoconazole fasted, 0.5 hour prior to receiving the 300 mg single dose of Mifepristone fasted. The evening of Day 1, subjects received 200 mg oral ketoconazole. Subjects remained in the clinic on Days 2, 3 and 4 to receive 200 mg BID oral ketoconazole, and for safety evaluation and collection of blood pharmacokinetic (PK) samples. Subjects were discharged from the clinic on Day 4 following evening administration of 200 mg oral ketoconazole, and returned to the clinic the morning and evening of Days 5 through 13 to receive 200 mg BID oral ketoconazole. Morning doses of ketoconazole on Days 0-13 were administered in the fasted state.

Subjects in both cohorts had blood sampling for determination of plasma concentrations of mifepristone and its metabolites within 30 minutes before mifepristone dosing and at hours 0.5, 1, 2, 4, 6, 8, 12, 24, 36, 48, 60, 72 (Day 4), 120 (Day 6), 192 (Day 9), 264 (Day 12), and 336 (Day 15) post mifepristone dose. Subjects in both cohorts returned to the study center on Day 15 for safety monitoring, and completion of the Termination Visit procedures, followed by discharge from the study. Safety was assessed by spontaneously reported adverse events, physical examinations, and routine clinical laboratory tests. To the extent possible, any adverse events deemed study drug-related and that were ongoing at the time of discharge from the study were followed-up to resolution or until a determination is made that the unresolved event was stable.

No subject experienced a serious adverse effect (SAE), or an adverse event (AE) that resulted in discontinuation from the study. Three subjects (25%) experienced at least 1 treatment-emergent adverse event (TEAE). All TEAEs were mild in intensity. No TEAE was considered by the investigator to be related to mifepristone. One TEAE of insomnia was considered by the investigator to be related to ketoconazole.

Minimal changes in laboratory test results were observed during the course of the study. No laboratory test result was considered by the investigator to be a TEAE. Any abnormal values or shifts from baseline were considered not clinically significant. No clinically significant changes in any electrocardiogram (ECG) parameter were observed.

Pharmacokinetics (PK): Blood samples were drawn within 30 minutes before mifepristone dosing and at hours 0.5, 1, 2, 4, 6, 8, 12, 24, 36, 48, 60, 72 (Day 4), 120 (Day 6), 192 (Day 9), 264 (Day 12), and 336 (Day 15) post mifepristone dose. Pharmacokinetic parameters were calculated for plasma concentrations of mifepristone and its metabolites following the single dose at Day 1. Descriptive statistics (count, mean, median, standard deviation, minimum, maximum, and % coefficient of variation) were provided. Mifepristone/metabolite concentrations were listed and summarized. Comparisons with previous study data were made. The mean PK parameters from this study are presented in Table 1 ("MIFE" indicates mifepristone). The abbreviations and symbols used in Table 1 have the following meanings: "Tmax" indicates time to maximum observed plasma concentration; "Tmin" indicates time to minimum observed concentration within the 24 hour dosing interval; "$C_{max}$" indicates maximum observed plasma concentration; "$C_{min}$" indicates minimum observed concentration within the 24 hour dosing interval; "$C_{avg}$" indicates average steady-state concentration and is defined as drug input rate (Ro) divided by drug removal rate (CLss) ($C_{avg}$=Ro/CLss, where f (the fraction absorbed) cancels out (f is a factor of both Ro and CLss); this equation reduces to $C_{avg}$=AUCtau/tau); "$AUC_{0-24}$" indicates area under the plasma concentration versus time curve from time 0 to 24 hours post-dose, calculated using the linear trapezoidal rule (this is the same as AUCtau where tau is 24 hours or 1 day); "% Fluct" indicates percent fluctuation in drug concentrations at steady-state computed as % Fluct=100×($C_{max}$−$C_{min}$)/$C_{avg}$.

PHARMACOKINETIC (PK) RESULTS: Mifepristone plasma concentrations showed a rapid initial decline followed by a slow decline over time. At later time points, concentrations showed an accelerated decline indicative of non-linear kinetics. Metabolites peaked later relative to parent mifepristone as would be expected. Mifepristone metabolite RU 42633 exposure was similar or even greater than that for mifepristone, while RU 42698 (a mifepristone metabolite) exposure was approximately 0.74 to 0.94 relative to mifepristone and RU 42848 (also a mifepristone metabolite) exposure was 0.53 to 0.68 relative to mifepristone. With increase in time interval, the fraction of AUC relative to mifepristone accounted for by metabolite increased.

Cohort 2 $C_{max}$ (where $C_{max}$ is the maximum observed plasma concentration) and AUCinf (where AUCinf is the area under the concentration-time curve from time of last dose to infinity) were similar to corresponding parameters in Cohort 1. The geometric mean ratio (GMR) for $C_{max}$ was 1.15 and that for AUCinf was 1.05. However, the 90% confidence intervals around the GMR were higher than the standard 80:125 reference interval. Thus, there may be a small increase in mifepristone exposure with a divided ketoconazole dose (200 mg BID vs. 400 mg OD), but this was minor. Terminal half-life was approximately the same in Cohort 2 versus Cohort 1 and Tmax was shorter for Cohort 2 versus Cohort 1.

SAFETY RESULTS: Among 12 subjects who received mifepristone, 3 (25%) experienced at least one treatment emergent adverse event (TEAE). All TEAEs were mild in intensity. No TEAE was considered by the investigator to be related to Mifepristone. One TEAE of insomnia was considered by the investigator to be related to ketoconazole. No subject experienced an SAE or an AE that resulted in discontinuation from the study. Minimal changes in laboratory test results were observed for subjects during the course of the study. No laboratory test result was considered by the investigator to be a TEAE. Any abnormal values or shifts from Baseline values were considered not clinically significant. No clinically significant changes in any ECG parameter were observed.

While PK parameters in Cohort 2 were similar to those in Cohort 1, the 90% confidence intervals around the GMR were higher than the standard 80:125 reference interval used for bioequivalence testing. Thus, there may be a small and minor increase in mifepristone exposure with a divided ketoconazole dose (200 mg BID vs. 400 mg OD). Terminal half-life was approximately the same in Cohort 2 versus Cohort 1 and Tmax was shorter for Cohort 2 versus Cohort 1. Mifepristone 300 mg was safe and well tolerated in healthy volunteers under the following treatment regimens: single-dose fasted with ketoconazole 400 mg OD for 14 days or ketoconazole 200 mg BID for 14 days.

Example 2

The primary objective of this study was to determine the effect of a 400 mg single dose of ketoconazole on the PK of an 8-day regimen of 300 mg or 600 mg OD mifepristone given following a moderate fat (34%) breakfast. This was an open-label study in healthy male subjects. In cohort 1, six subjects received mifepristone 300 mg OD for 8 days. In cohort 2, six subjects received mifepristone 600 mg OD for 8 days. The 400 mg single dose of ketoconazole was given to all subjects on day 8. Three subjects discontinued early from the study: one subject in cohort 1 due to new onset sinus bradycardia, and two subjects in cohort 2 due to withdrawn consent.

METHODOLOGY: Twelve subjects were enrolled, six in Cohort 1 and 6 in Cohort 2. Three subjects discontinued early from the study, one subject in Cohort 1 due to an adverse event of sinus bradycardia, and two subjects in Cohort 2 due to withdrawn consent.

Cohort 1: Subjects participated in a Screening visit to assess eligibility, and returned to the clinic on Days 1-6 to receive 300 mg oral mifepristone following a moderate fat breakfast. On Day 7 subjects were admitted to the clinic in the fasted state for a pre-dose PK blood draw, after which they received 300 mg oral mifepristone following a moderate fat breakfast. Subjects had serial blood sampling for determination of mifepristone and its metabolites at hours 0.5, 1, 2, 4, 6, 8, and 12 post Day 7 dose. On Day 8, a pre-dose PK sample was drawn within 30 minutes prior to ketoconazole dosing for determination of plasma concentrations of mifepristone and its metabolites and ketoconazole. Following a moderate fat breakfast on Day 8, subjects received 400 mg ketoconazole 0.5 hours prior to 300 mg mifepristone and had serial blood sampling at hours 0.5, 1, 2, 4, 6, 8, 12, 24, 36, 48, 60, 72, and 120 post mifepristone dose for determination of plasma concentrations of mifepristone and its metabolites; and at hours 0.5, 1, 1.5, 2, 3, 4, 6, 8, 12, 24, 36, and 48 post ketoconazole dose for determination of plasma concentrations of ketoconazole. Subjects were discharged on Day 11.

Cohort 2: Subjects participated in a Screening visit to assess eligibility and returned to the clinic on Days 1-6 to receive 600 mg oral mifepristone following a moderate fat breakfast. On Day 7 subjects were admitted to the clinic in the fasted state for a pre-dose PK blood draw, after which they received 600 mg oral mifepristone following a moderate fat breakfast. Subjects had serial blood sampling for determination of mifepristone and its metabolites at hours 0.5, 1, 2, 4, 6, 8, and 12 post Day 7 dose. On Day 8, a pre-dose PK sample was drawn within 30 minutes prior to ketoconazole dosing for determination of plasma concentrations of mifepristone and its metabolites and ketoconazole. Following a moderate fat breakfast on Day 8, subjects received 400 mg ketoconazole 0.5 hours prior to 600 mg mifepristone and had serial blood sampling at hours 0.5, 1, 2, 4, 6, 8, 12, 24, 36, 48, 60, 72, and 120 post mifepristone dose for determination of plasma concentrations of mifepristone and its metabolites; and at hours 0.5, 1, 1.5, 2, 3, 4, 6, 8, 12, 24, 36, and 48 post ketoconazole dose for determination of plasma concentrations of ketoconazole. Subjects were discharged on Day 11. Subjects in both cohorts returned to study center on Day 13 for safety monitoring, collection of the 120-hour PK draw, and completion of the Termination Visit procedures, followed by discharge from the study. To the extent possible, any adverse events deemed study drug-related and that were ongoing at the time of discharge from the study were followed-up to resolution or until a determination was made that the unresolved event was stable.

DIAGNOSIS AND MAIN CRITERIA FOR INCLUSION: Healthy male volunteers between the ages of 18 to 45 years of age with a body mass index (BMI) ranging between 19 and 32 kg/m2 and a weight of at least 60 kg (132 lbs) were enrolled. Subjects had no clinically significant abnormal findings on the physical examination, ECG, blood pressure, heart rate, medical history, or clinical laboratory results during screening. The QTc interval at screening was less than 450 msec.

DURATION OF TREATMENT: Up to a total of 28 days, including up to 2 weeks screening, dosing on Days 1-8, safety observation, and PK sample collection through Day 13. For measuring the pharmacokinetics of mifepristone, samples were collected within 30 minutes before Day 7 mifepristone dose and at hours 0.5, 1, 2, 4, 6, 8, and 12 post Day 7 mifepristone dose; within 30 minutes before Day 8 ketoconazole dosing and at hours 0.5, 1, 2, 4, 6, 8, 12, 24, 36, 48, 60, 72, and 120 post Day 8 mifepristone dose. For measuring the pharmacokinetics of ketoconazole, samples were collected predose on Day 8 (24 hr sample from Day 7), and at hours 0.5, 1, 1.5, 2, 3, 4, 6, 8, 12, 24, 36, and 48 hours post ketoconazole dose.

Safety was assessed by spontaneously reported adverse events, physical examinations, and routine clinical laboratory tests. Adverse event data were tabulated. Physical findings and laboratory test results were listed by subject.

SAFETY RESULTS: No subject experienced an SAE. Among twelve subjects who received mifepristone, six subjects (50%) experienced at least 1 TEAE. TEAEs were predominantly mild in intensity. The majority of subjects (5/6) with TEAEs were in Cohort 2 and onset of the majority of TEAEs occurred on or after Day 8 during treatment with both ketoconazole and mifepristone 600 mg. TEAEs considered possibly or probably related to mifepristone administration in four subjects in Cohort 2 were dizziness, nausea, vomiting, dry mouth, and rash. One TEAE of headache was considered by the investigator to be possibly related to both ketoconazole and mifepristone administration. One subject in Cohort 1 with a TEAE of nodal arrhythmia on Day 8 was withdrawn by the investigator. The event was considered mild in severity and not considered related to study medication. The corresponding ECG abnormality noted as "sinus bradycardia" was considered not clinically significant. No subject experienced an SAE.

Minimal changes in laboratory test results were observed for subjects during the course of the study. No laboratory test result was considered by the investigator to be a TEAE. There were no clinically significant changes or abnormalities in vital signs, physical examinations or body weights during the study. Abnormal ECGs occurred in four subjects and no abnormality was considered clinically significant.

STATISTICAL METHODS: Pharmacokinetics (PK): Pharmacokinetic parameters $C_{max}$, $C_{trough}$, and interdosing interval AUC were calculated for plasma concentrations of mifepristone and its metabolites following dose on Days 7 and 8. Descriptive statistics (count, mean, median, standard deviation, minimum, maximum, and % coefficient of variation) were provided. mifepristone/metabolite concentrations were listed and summarized. GM means of $C_{max}$ and $AUC_{0-24}$ were compared for Day 8 to Day 7 in this study and also to combined data of 300 mg OD mifepristone in previous multiple dose studies. Additionally, comparisons were made between the PK results of cohort 1 and 2. Pharmacokinetic parameters $C_{max}$, T½ and total AUC were calculated for plasma concentrations of ketoconazole following the single dose on Day 8. Descriptive statistics (count, mean, median, standard deviation, minimum, maximum, and % coefficient of variation) were provided. Ketoconazole concentrations were listed and summarized. GM means of $C_{max}$ and total AUC were compared for the single dose in this study to the combined data of reported 400 mg single doses of ketoconazole of healthy subjects from the literature.

The mean (±SD) age of subjects was 29.4±6.8 years, and the mean BMI at screening was 25.61±3.27 kg/m2. Seven of twelve subjects (58.3%) were White, and 5/12 (41.7%) were Black/African American. Five of the 12 subjects (41.7%) were of Hispanic or Latino ethnicity.

PHARMACOKINETIC (PK) RESULTS: PK data for mifepristone and metabolites was available for eleven of the 12 enrolled subjects and data for ketoconazole PK analyses was available for 10 subjects. Concentrations of mifepristone and each metabolite were above the limits of detection during the entire sampling duration from Day 7 predose to Day 13 (end of study). mifepristone plasma concentrations showed a rapid initial decline followed by a slow decline over time and metabolites peaked later relative to parent mifepristone as expected. Mean RU 42633 and RU 42848 exposure was similar or even greater than that for mifepristone, while RU 42698 exposure was lower. Ketoconazole PK after a single dose on Day 8 was readily computed. Co-administration of ketoconazole increased mifepristone and metabolite exposure. In the presence of 400 mg ketoconazole on Day 8, Cohort 1 mifepristone $C_{max}$ and AUC0-24 increased by 20% and 25% relative to the prior Day 7 without ketoconazole. This effect was slightly greater at 600 mg OD mifepristone in Cohort 2, where $C_{max}$ and $AUC_{0-24}$ increased by 39% and 28% between Day 7 and Day 8. A dose of 600 mg OD mifepristone (Cohort 2) resulted in higher mifepristone and metabolite exposure relative to a dose of 300 mg OD (Cohort 1) both alone and in the presence of 400 mg ketoconazole. This increase was less than proportionate to the two-fold dose increment. On Day 7 without ketoconazole, mifepristone $C_{max}$ and $AUC_{0-24}$ at 600 mg OD were 42% and 48% greater than at 300 mg OD. This dose effect was greater in the presence of 400 mg ketoconazole. Day 8 mifepristone $C_{max}$ and $AUC_{0-24}$ were 65% and 52% greater at 600 mg OD than at 300 mg OD. mifepristone half-life on Day 8 in the presence of 400 mg ketoconazole was similar between the two mifepristone dose levels. Day 8 half-life was 13% greater at 600 mg OD than at 300 mg OD. Ketoconazole exposure following a single 400 mg dose on Day 8 of a regimen of 600 mg OD mifepristone was 37% and 36% higher ($C_{max}$ and AUCinf) relative to a mifepristone regimen of 300 mg OD. Ketoconazole half-life on either mifepristone regimen was not appreciably different. The addition of a single dose of 400 mg ketoconazole to 300 mg or 600 mg OD mifepristone on Day 8 resulted in exposure increases in $C_{max}$ and $AUC_{0-24}$ that were similar to historical values at 600 mg or 1200 mg OD in the fasted state and 1200 mg OD in the fed state, respectively. Although the increase in exposure due to the addition of ketoconazole was only between 20% and 39% in absolute terms, the resulting exposure was similar to that of a dose 2 to 3 times greater. This is believed to be due to a lack of dose-proportional kinetics for mifepristone.

The mean PK parameters and results from this study are presented in Table 2.

The abbreviations and symbols used in Table 2 have the following meanings:

"Tmax" indicates time to maximum observed plasma concentration; "Tmin" indicates time to minimum observed concentration within the 24 hour dosing interval; "$C_{max}$" indicates maximum observed plasma concentration; "$C_{min}$" indicates minimum observed concentration within the 24 hour dosing interval; "$C_{avg}$" indicates average steady-state concentration and is defined as drug input rate (Ro) divided by drug removal rate (CLss) ($C_{avg}$=Ro/CLss, where f cancels out; this equation reduces to $C_{avg}$=AUCtau/tau); "$AUC_{0-24}$" indicates area under the plasma concentration versus time curve from time 0 to 24 hours post-dose, calculated using the linear trapezoidal rule (this is the same as AUCtau where tau is 24 hours or 1 day); "% Fluct" indicates percent fluctuation in drug concentrations at steady-state computed as % Fluct=100×($C_{max}$−$C_{min}$)/$C_{avg}$.

Drug-drug interaction (DDI) effects of ketoconazole on mifepristone and of mifepristone on ketoconazole were studied. A single 400 mg dose of ketoconazole caused a detectable increase in mifepristone exposure at mifepristone doses of 300 and 600 mg OD, and mifepristone at these doses caused a detectable increase in ketoconazole exposure. Although the increase in mifepristone exposure due to the addition of ketoconazole was only between 20% and 39% in absolute terms, the resulting exposure was similar to that of a dose 2 to 3 times greater. This is believed to be due to a lack of dose-proportional kinetics for mifepristone. Predominantly mild AEs occurred and were observed primarily in subjects administered ketoconazole and mifepristone 600 mg.

Example 3

A Phase 1, single-center, open-label study was performed to study the effect of oral twice-daily doses of 200 mg of ketoconazole given with multiple oral once-daily doses of 600 mg of mifepristone in healthy male volunteers, during which all drug administrations were given after a typical meal (34% fat content). An objective of this study was to determine the effect of ketoconazole 200 mg twice daily on the PK of mifepristone 600 mg once daily when both drugs were administered with food. A single dose of ketoconazole was administered on Day −1. During multidose administration, mifepristone was administered on Days 1-17 and ketoconazole on Days 13-17; follow-up continued on Days 18-31. Sixteen subjects were enrolled (mean age 31.9 years; 8 black, 6 white, 2 other), and two subjects discontinued before starting the mifepristone/ketoconazole combination treatment.

The study was a two period study design. In Period 1: 600 mg mifepristone was administered once daily from Day 1 to Day 12; pharmacokinetic samples were taken before each dose for assay of mifepristone and active metabolites (mono-demethylated metabolite, RU 42633; hydroxylated metabolite, RU 42698; and di-demethylated metabolite, RU 42848) to confirm that steady-state was achieved, and for a dose-interval concentration-profile on Day 12. In Period 2: 600 mg mifepristone once daily was continued in combination with 200 mg ketoconazole twice daily from Days 13 to 17; pharmacokinetic samples were taken for assay of both mifepristone and metabolites, and ketoconazole before dosing on Days 13 to 17, and on Day 17 for a dose-interval concentration-time profile A secondary objective was to determine if the effect of 200 mg BID ketoconazole on the PK of co-administered 600 mg OD mifepristone at steady-state exceeded exposure to mifepristone and metabolites compared to that of 1200 mg OD mifepristone with food, the labeled dosing regimen with the highest mean observed exposure in healthy subjects.

Effects of Co-Administration with Ketoconazole on Mifepristone and Metabolites: The concentrations of mifepristone and the hydroxylated metabolite, RU 42698, were higher on Day 17 (600 mg mifepristone daily co-administered with 200 mg ketoconazole twice daily) than on Day 12 (mifepristone alone). Concentrations of RU 42633 and RU 42848 were similar on Day 17 and Day 12. Results of the formal statistical analysis are shown in Table 3.

For mifepristone, the geometric mean ratio of test to reference for $C_{max}$ was 127.59% (90% CI: 116.66, 139.54, where "CI" means "confidence interval" and "90% CI" means "90% confidence interval") and for $AUC_{0-24}$ was 138.01% (90% CI: 127.12, 149.84). The lower bound of the 90% confidence intervals exceeded 100% and the upper bound exceeded 125%. Thus, co-administration with ketoconazole increased mifepristone exposure. Similarly, for metabolite RU 42698, the lower bounds of the 90% confidence intervals exceeded 100% and both geometric mean ratios and the upper bound of the 90% confidence interval exceeded 125%, and thus exposure to this metabolite was increased by ketoconazole.

For metabolites RU 42848 and RU 42633, the calculated geometric mean ratios and 90% confidence intervals of exposure ratios were within the standard 80:125 comparison interval and thus not affected by ketoconazole.

Effects of Co-administration with mifepristone on Ketoconazole: The plasma concentration-time profiles of ketoconazole given twice daily with mifepristone on Day 17 were much higher than for ketoconazole given as a single dose alone on Day −1. Results of the formal statistical analysis are shown in Table 4.

The geometric mean ratio of test to reference for $C_{max}$ was 252.71% (90% CI: 214.85, 297.26) and for AUC was 365.36% (90% CI: 333.78, 399.93). Thus, the geometric mean ratio and both lower and upper bounds of the 90% confidence intervals were entirely above the standard 80:125 comparison interval and exposure on Day 17 (with mifepristone) was higher than on Day −1 (ketoconazole alone).

Comparison of Mifepristone Exposure with mifepristone Labeled Doses: The concentration-time plots showed that mean mifepristone concentrations on Day 17 in the present study were less than those in the fed condition in a previous "historic" study in which subjects received 1200 mg mifepristone daily for seven days. Mifepristone was administered to the subjects within thirty minutes following a typical meal (34% fat) in both the present study and in the historic study. Results of the formal statistical analysis are shown in Table 5.

For mifepristone, the geometric mean ratio of test to reference for $C_{max}$ was 84.64% (90% CI: 72.92, 98.23); for $AUC_{0-24}$ it was 87.27% (90% CI: 74.72, 101.94). The 90% confidence intervals were below and overlapping the standard 80:125 comparison interval. The mean mifepristone concentrations in subject receiving 600 mg mifepristone following a 34% fat meal were less than the mifepristone concentrations in the historic study. As shown in Table 5, administration of 600 mg mifepristone in the fed state with ketoconazole resulted in mifepristone concentrations that were less than the mifepristone concentrations measured in subjects receiving 1200 mg mifepristone daily in the absence of ketoconazole. The Geometric Mean Ratio (GMR) values in Table 5 suggest that mifepristone 600 mg co-administered with ketoconazole yields mifepristone exposure 13-15% less than that of 1200 mg mifepristone in the absence of ketoconazole; for the metabolites, corresponding values range from an 18-19% decrease to a 17-18% increase. Thus, administration of 600 mg mifepristone daily with ketoconazole resulted in mifepristone concentrations that were not higher than the mean observed exposure at 1200 mg mifepristone; both treatments given following typical 34% fat meal. The value of 87% for GMR of the AUCs suggests that 900 mg mifepristone in the presence of ketoconazole would better match the exposure of a subject to 1200 mg mifepristone alone than would 600 mg mifepristone in the presence of ketoconazole. Thus, these data also support the use of 900 mg mifepristone, and higher doses as well, in the presence of ketoconazole.

For metabolite RU 42633, the 90% confidence intervals were within the standard interval for $C_{max}$ (geometric mean ratio 96.31%) and just overlapping the lower bound of the standard interval for $AUC_{0-24}$ (geometric mean ratio 91.34%). For metabolite RU 42698, confidence intervals for both $C_{max}$ and $AUC_{0-24}$ were overlapping and above the standard interval (geometric mean ratio $C_{max}$:116.55%; $AUC_{0-24}$:118.18%). For metabolite RU 42848, the 90% confidence intervals were overlapping and below the standard interval for $C_{max}$ (geometric mean ratio 82.45%) and $AUC_{0-24}$ (ratio 81.43%).

RU 42698 is a relatively minor metabolite and comprises 9% of the total steady-steady $AUC_{0-24}$ of mifepristone, RU42633, RU42698, RU42848 alone and 13% of the total steady-steady $AUC_{0-24}$ in the presence of ketoconazole. Therefore, the increase in RU 42698 $AUC_{0-24}$ in the presence of ketoconazole is considered to be minor.

FIG. 1 illustrates the results of measurements of plasma levels of mifepristone, RU42633, RU42698, and RU 42848. These measurements were made prior to the daily administration of mifepristone to the subject; thus the mifepristone and metabolite concentrations are "trough" concentrations. These results show that trough concentrations of mifepristone and RU42848 were increasing day-by-day through the start of ketoconazole administration (Day 13). This indicates that steady state conditions may not have been attained at the time of ketoconazole administration (which began on day 13).

Figure 2:
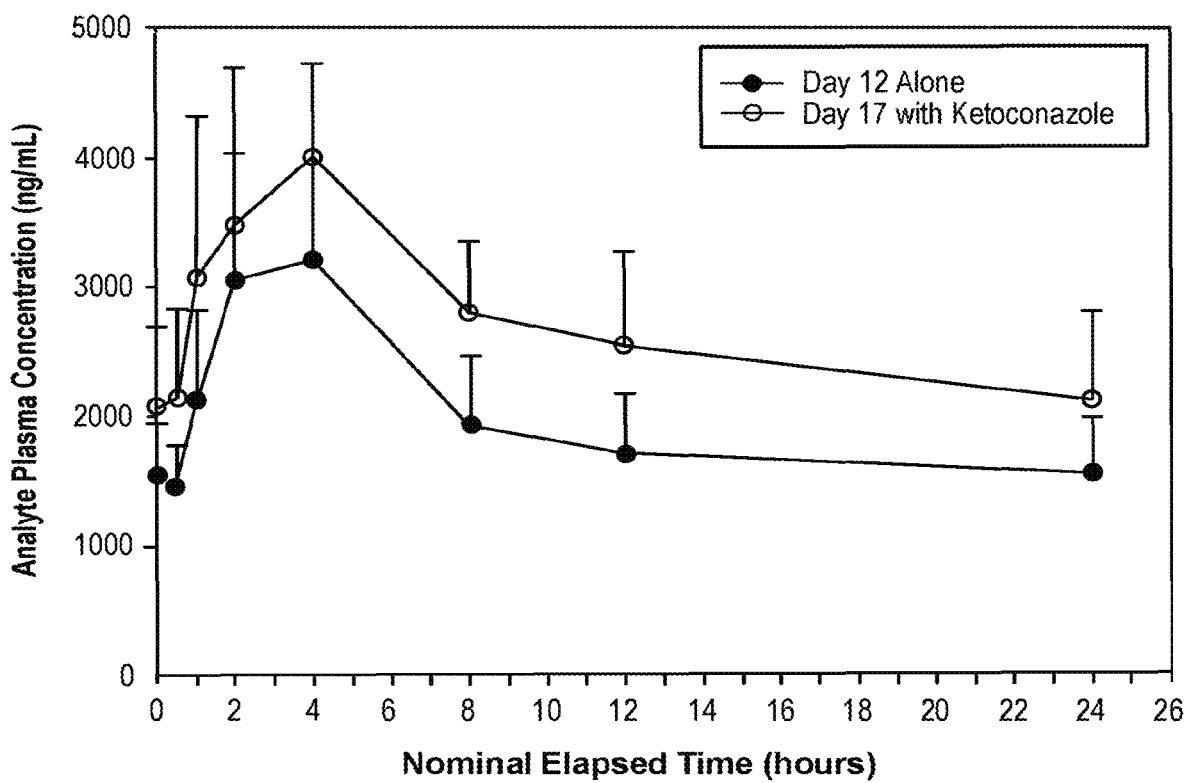
FIG. 2 shows the plasma concentration profile of mifepristone measured in healthy male volunteers on day twelve (before administration of ketoconazole) and on day seventeen (the fifth day of ketoconazole administration).

FIG. 2 shows the plasma concentration profile of mifepristone before and after inhibition of CYP3A by ketoconazole. Applicant notes that the time 0 values (pre-dose) differ by ~500 ng/ml, a difference that is maintained relatively constant throughout much of the 24-hour sampling interval. Thus, if the daily increase in trough concentrations between days 7 and 12 persevered through day 17, an unknown fraction of the increased AUC (and $C_{max}$) between Day 12 and Day 17 could be due to further mifepristone administration rather than by an effect of ketoconazole alone. Thus, the values reported in Table 3 may overstate the impact of CYP3A inhibition on exposure to mifepristone (and RU42848).

CONCLUSIONS: Co-administration of 600 mg mifepristone once daily with 200 mg ketoconazole twice daily resulted in a mean increase in exposure to mifepristone of approximately 28% ($C_{max}$:geometric mean ratio 127.59% [90% CI: 116.66, 139.54]) and 38% ($AUC_{0-24}$:geometric mean ratio 138.01% [90% CI:127.12, 149.84]). These exposures are approximately 85% of those observed following the highest labeled dose of mifepristone (1200 mg daily).

The mean increase in exposure to the hydroxylated metabolite, RU 42698 (approximately 70%), was somewhat greater than the increase in exposure to parent, resulting in exposure that was approximately 15 to 20% higher than that following the highest labeled dose of mifepristone. In contrast, co-administration with ketoconazole resulted in little change in exposure to the mono-demethylated metabolite, RU 42633, or di-demethylated metabolite, RU 42848; exposure to these metabolites was similar to or slightly lower than exposure following the highest labeled dose.

The results presented in this example indicate that, with inhibition of CYP3A (e.g., by co-administration of a strong CYP3A inhibitor such as ketoconazole), a subject administered 900 mg mifepristone daily would experience corresponding increases in mifepristone Cmax and AUC of 27.59% and of 38.01%, respectively, which should yield systemic exposures similar in magnitude to those previously attained with 1200 mg daily. Thus, the results of these measurements indicate that a subject, previously receiving a dose of 1200 mg mifepristone daily, may be safely administered a dose of 900 mg mifepristone daily when a strong CYP3A inhibitor such as ketoconazole is added to the regimen. Similarly, the results of these measurements indicate that a subject, previously receiving a dose of 900 mg mifepristone daily, may be safely administered a dose of 600 mg mifepristone daily when a strong CYP3A inhibitor such as ketoconazole is added to the regimen. In addition, the results of these measurements indicate that a subject, previously receiving a dose of 600 mg mifepristone daily, may be safely administered a dose of 300 mg mifepristone daily when a strong CYP3A inhibitor such as ketoconazole is added to the regimen.

No deaths or SAEs were reported during the study. Two subjects discontinued due to AEs (moderate hypertension in one subject and moderate bilateral rash on the upper arms and thighs in the other subject, both during the mifepristone-only treatment period). At least one TEAE was reported in 55.6% (9 of 16) of the subjects during treatment with mifepristone alone, in 57.1% (8 of 14) of the subjects during the mifepristone/ketoconazole treatment period, and in 7.1% (1 of 14) of the subjects during the washout period.

The majority of TEAEs were mild. Four subjects reported moderate TEAEs: three subjects during treatment with mifepristone alone (1 each reporting hypertension, rash, and vomiting) and 1 subject during treatment with mifepristone/ketoconazole (headache). All four moderate AEs were considered possibly or probably related to mifepristone treatment. Only 1 of the moderate AEs was considered to be possibly related to ketoconazole treatment. No severe TEAEs were reported.

Three subjects had elevated laboratory test results that were reported as drug-related TEAEs. Mildly elevated liver enzymes were noted for one subject starting on the morning of Day 14, and mildly elevated creatinine levels were noted for two subjects starting on the morning of Day 14. Dosing was not interrupted for any of the subjects, and the events resolved without sequelae.

No clinically significant effects of multiple-dose mifepristone treatment with or without multiple-dose ketoconazole treatment were observed on hematology or urinalysis parameters, vital signs, or ECGs.

Example 4

This Example describes a Phase 1, single-center, open-label, fixed-sequence, drug-drug interaction study that studied the effect of multiple daily doses of oral itraconazole 200 mg, a strong inhibitor of CYP enzymes, given with mifepristone 900 mg once per day (OD), in healthy male subjects. This study was conducted in accordance with Good Clinical Practice under the guidance of an Institutional Review Board and in accordance with applicable local legal and regulatory requirements. The schedule used during this study is shown in Table 6.

KORLYM® was supplied in 300 mg tablets for oral administration. Three or four tablets were administered once daily (OD) to provide either the 900 mg or 1200 mg per day dose.

Itraconazole was supplied
  in 100 mg capsules for oral administration. Two capsules were administered once daily (OD) to provide the 200 mg per day dose.

All drug administrations were oral and were given after the morning meal. Mifepristone, when given alone (1200 mg on days 1 to 14; 900 mg on days 15 to 28), was administered within 30 minutes after breakfast; itraconazole (200 mg) was administered within 30 minutes after breakfast, and then mifepristone (900 mg) was administered approximately 5 minutes after the administration of itraconazole (days 29 to 42).

The inclusion criteria required, among other criteria, that the subjects be healthy male subjects between the ages of 18 and 65, weigh more than 110 pounds, and have a body mass index (BMI) of 18 to 32 kg/m². The design included a Screening Period of up to 3 weeks (subjects were screened at a time between days −21 to −1 prior to the first treatment period), three 14-day treatment periods, and a Follow-Up (FU) Period of 14 days for safety observation.

Subjects meeting the inclusion criteria (n=22) were administered drug daily and blood samples were taken on the days indicated below during Periods 1-3 and on day 43 of the follow-up period. Subjects were confined to the clinical research unit on days −1 to 1 (prior to and including the day of administration of the first mifepristone dose); on days 13-15; on days 27-29; and on days 42-43.

Treatment regimens and durations were as follows:
Period 1, Days 1-14: mifepristone 1200 mg once daily (OD) after a meal.
  (days 1, 2, 4, 6, 8, 11, 12, and 13); PK samples were taken 30 minutes prior to drug
  (day 14) 24-hour PK sampling profiles were obtained.
Period 2, Days 15-28: mifepristone 900 mg OD after a meal.
  (days 15, 16, 18, 20, 22, 25, 26, and 27); PK samples were taken 30 minutes prior to drug
  (day 28) 24-hour PK sampling profiles were obtained
Period 3, Days 29-42: mifepristone 900 mg OD plus itraconazole 200 mg OD after a meal.
  (days 29, 30, 32, 34, 36, 39, 40, and 41); PK samples were taken 30 minutes prior to drug (day 42) 24-hour PK sampling profiles were obtained Subjects presented at the Clinical Research Unit (CRU) after an 8-hour overnight fast, then predose PK samples were taken and other evaluations (predose electrocardiograms (ECGs), plasma cortisol and ACTH, serum chemistry tests) were performed. Subjects consumed a breakfast meal, and the drug(s) (mifepristone monotherapy or in combination with itraconazole) was/were administered within about 30 minutes after consumption of breakfast. On the specific days indicated above, additional blood draws for determining 24-hour PK profiles were performed.

Safety and tolerability was assessed by adverse events (AEs) monitoring, measurement of vital signs, 12-lead ECG recordings, physical examinations, and by clinical laboratory safety tests.

Pharmacokinetic (PK) parameters measured and computed included AUC (area under the concentration–time curve), $AUC_{0-24}$ (AUC values from time 0 to 24 hours postdose), $C_{max}$ (maximum concentration), and Css (average steady-state concentration, calculated as $AUC_{0-24}/24$).

PK parameters were computed for mifepristone and its three major metabolites (RU-42633, RU-42698, and RU-42848) using a non-compartmental analysis method in which $AUC_{0-24}$ was computed using the linear trapezoid rule.

Figure 3:
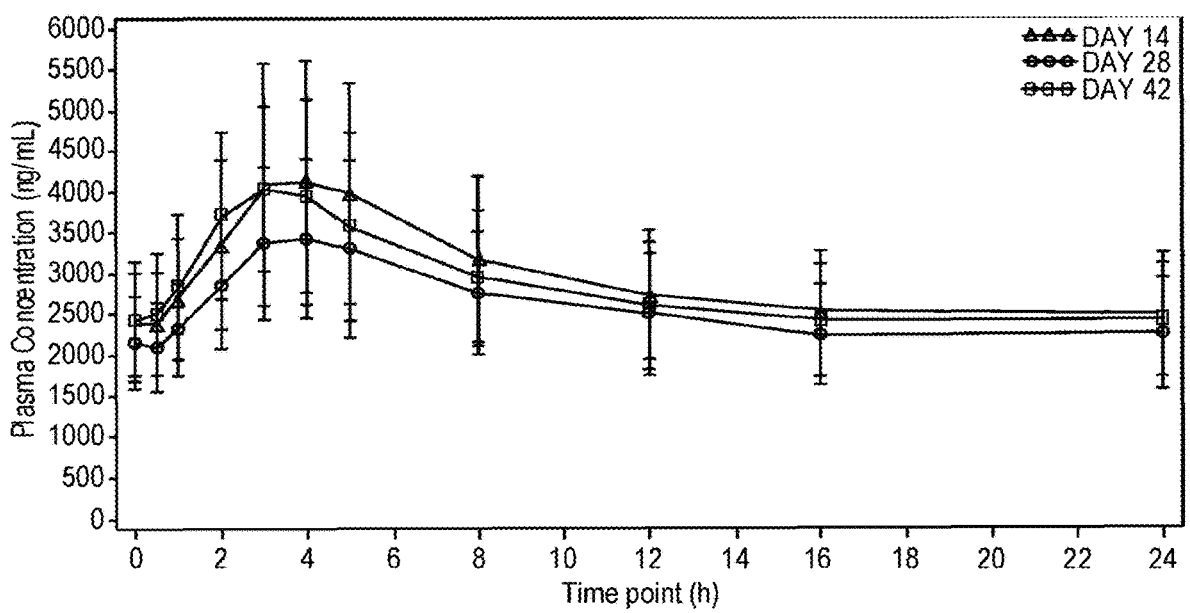
FIG. 3 shows the plasma concentration profile of mifepristone measured in healthy male volunteers over the course of twenty four hours since dosing on day 14 of the study (administration of 1200 mg mifepristone once-per-day; triangles); on study day 28 (administration of 900 mg mifepristone once-per-day; circles); and on study day 42 (administration of 900 mg mifepristone once-per-day and of 200 mg itraconazole once-per-day; squares).

FIG. 3 shows the plasma concentration profile of mifepristone measured in healthy male volunteers over the course of twenty four hours since dosing on day 14 (Visit 1; once-daily administration of 1200 mg mifepristone alone; triangles); on day 28 (Visit 2; once-daily administration of 900 mg mifepristone alone; circles); and on day 42 (Visit 3; once-daily administration of 900 mg mifepristone and of 200 mg itraconazole; squares). The maximum exposure (mifepristone plasma concentration) was observed at about 4 hours after drug administration for mifepristone alone and also for mifepristone administered with itraconazole.

Administration of itraconazole along with mifepristone increased exposure (plasma levels) of mifepristone as compared to mifepristone alone, so that, as expected, the maximum exposure for 900 mg mifepristone alone was less than the maximum exposure for 1200 mifepristone alone. However, surprisingly, the maximum exposure measured for 900 mg mifepristone with 200 mg itraconazole was not very different than the maximum exposure for 1200 mifepristone alone. This is shown in Table 7, which presents plasma levels of mifepristone and three of its metabolites, RU-42633, RU-42698, and RU-42848, measured in subjects administered 900 mg mifepristone OD with 200 mg itraconazole OD and plasma levels measured in subjects administered 1200 mg mifepristone OD alone. The ratios (as percent) of $C_{max}$ and $AUC_{0-24}$ for (900 mg mifepristone+200 mg itraconazole)/(1200 mg mifepristone) are presented in the column labeled "Ratio (%)" (the ratio of the $C_{max}$ and $AUC_{0-24}$ geometric means determined within the limits of the 90% confidence interval).

The geometric mean ratio (%) for $C_{max}$ (mifepristone $C_{max}$ observed for subjects receiving 900 mg mifepristone OD and 200 mg itraconazole OD) divided by (mifepristone $C_{max}$ observed for subjects receiving 1200 mg mifepristone OD alone) was about 98%. The AUC geometric mean ratio (%) of (mifepristone $AUC_{0-24}$ observed for subjects receiving 900 mg mifepristone OD and 200 mg itraconazole OD) divided by (mifepristone $AUC_{0-24}$ observed for subjects receiving 1200 mg mifepristone OD alone) was about 97%. These data demonstrate that the mifepristone maximum exposure for 900 mg mifepristone OD with 200 mg itraconazole OD was not greater than, but was nearly equivalent to, the mifepristone maximum exposure for 1200 mg mifepristone OD.

Thus surprisingly, the maximum exposure for 900 mg mifepristone OD when administered with 200 mg itraconazole OD was about the same as the maximum exposure for 1200 mg mifepristone OD alone. This shows that concomitant administration of itraconazole did not cause extremely high levels of mifepristone.

Table 8 presents plasma levels of mifepristone and three of its metabolites, RU-42633, RU-42698, and RU-42848, measured in subjects administered 900 mg mifepristone OD with 200 mg itraconazole OD and plasma levels measured in subjects administered 900 mg mifepristone OD alone. Table 8 also includes a column labeled "Ratio (%)" presenting the geometric mean ratios determined within the limits of the 90% confidence interval for mifepristone and its metabolites, thus providing relative measures of the plasma levels of mifepristone and its metabolites (plasma levels obtained with 900 mg mifepristone OD with 200 mg itraconazole OD divided by plasma levels obtained with 900 mg mifepristone OD).

Table 8 presents this geometric mean ratio (%) data for mifepristone and the three mifepristone metabolites RU-42633, RU-42698, and RU-42848 comparing the geometric mean plasma levels measured in subjects administered 900 mg mifepristone OD with 200 mg itraconazole OD with the geometric mean plasma levels measured in subjects administered 900 mg mifepristone OD alone. The ratio of mifepristone $C_{max}$ was about 120% ($C_{max}$ measured in subjects administered 900 mg mifepristone OD with 200 mg itraconazole OD divided by $C_{max}$ measured in subjects administered 900 mg mifepristone OD alone). The ratio of mifepristone $AUC_{0-24}$ was about 110% ($AUC_{0-24}$ measured in subjects administered 900 mg mifepristone OD with 200 mg itraconazole OD divided by $AUC_{0-24}$ measured in subjects administered 900 mg mifepristone OD alone).

As indicated in Tables 7 and Table 8 for mifepristone and for the mifepristone metabolites RU-42633, RU-42698, and RU-42848, the plasma levels obtained for 900 mg mifepristone OD and 200 mg itraconazole OD were close to those obtained by 1200 mg mifepristone OD alone, and were only about 20% higher (or less) than those levels obtained by 900 mg mifepristone OD alone. Thus, administration of 900 mg of mifepristone OD with 200 mg OD of a strong CYP3A inhibitor such as itraconazole provides about the same plasma mifepristone levels as does administration of 1200 mg mifepristone alone.

1200 mg OD mifepristone is a safe dose approved for use by the U.S. Food and Drug Administration (FDA). The similarity in plasma levels for mifepristone and its metabolites obtained with 900 mg mifepristone OD with 200 mg itraconazole OD, as compared to those plasma levels obtained with 1200 mg mifepristone OD alone, indicates that 900 mg mifepristone OD may be safely administered with itraconazole.

Since itraconazole is a strong CYP3A inhibitor, and since itraconazole is considered an exemplar strong CYP3A inhibitor and may be used to determine the effects of the class of strong CYP3A inhibitors (see FDA "Clinical Drug Interaction Studies—Study Design, Data Analysis, and Clinical Implications Guidance for Industry", pages 10-11 (https://www.fda.gov/downloads/drugs/guidances/ucm292362.pdf), these results indicate that mifepristone may also be safely administered with other strong CYP3A inhibitors (such as, e.g., ketoconazole, itraconazole, nefazodone, ritonavir, nelfinavir, indinavir, atazanavir, amprenavir and fosamprenavir, clarithromycin, conivaptan, lopinavir/ritonavir, posaconazole, saquinavir, telithromycin, and voriconazole). In addition, since less strong CYP3A inhibitors would be expected to have smaller effects on plasma levels of mifepristone and its metabolites, these results indicate that mifepristone may also be safely administered with other CYP3A inhibitors in addition to those listed above, including CYP3A inhibitors that are not strong CYP3A inhibitors (such as, e.g., fluconazole, cimetidine, boceprevir, and telaprevir).

Example 5

The treatment regimen of a patient suffering from excess cortisol, who is receiving treatment with mifepristone at a daily dose of 1200 mg mifepristone, is altered to include concomitant administration of an effective amount of ketoconazole and a reduced daily dose of mifepristone, where the reduced daily dose of mifepristone is 900 mg, so that the patient receives concomitant administration of ketoconazole and mifepristone. A measurement indicates that the liver function of the patient is not significantly compromised by the concomitant administration of ketoconazole and the reduced dose of mifepristone.

Example 6

The treatment regimen of a patient suffering from excess cortisol, who is receiving treatment with mifepristone at a daily dose of 900 mg mifepristone, is altered to include concomitant administration of an effective amount of ketoconazole and a reduced daily dose of mifepristone, where the reduced daily dose of mifepristone is 600 mg, so that the patient receives concomitant administration of ketoconazole and mifepristone. A measurement indicates that the liver function of the patient is not significantly compromised by the concomitant administration of ketoconazole and the reduced dose of mifepristone.

Example 7

The treatment regimen of a patient suffering from excess cortisol, who is receiving treatment with mifepristone at a daily dose of 600 mg mifepristone, is altered to include concomitant administration of an effective amount of ketoconazole and a reduced daily dose of mifepristone, where the reduced daily dose of mifepristone is 300 mg, so that the patient receives concomitant administration of ketoconazole and mifepristone. A measurement indicates that the liver function of the patient is not significantly compromised by the concomitant administration of ketoconazole and the reduced dose of mifepristone.

Example 8

The treatment regimen of a patient suffering from excess cortisol, who is receiving treatment with mifepristone at a daily dose of 1500 mg mifepristone, is altered to include concomitant administration of an effective amount of ketoconazole and a reduced daily dose of mifepristone, where the reduced daily dose of mifepristone is 1200 mg, so that the patient receives concomitant administration of ketoconazole and mifepristone. A measurement indicates that the liver function of the patient is not significantly compromised by the concomitant administration of ketoconazole and the reduced dose of mifepristone.

All patents, patent applications, and publications identified herein are hereby incorporated by reference herein in their entireties.

TABLE 1

| Product ID/ Batch No. (NME) | Study Objective | Study Design | No. Subjects Enter/ Complete (M/F) | Age: Mean Range | Treatments | | MIFEPRISTONE Mean PK Parameters (SD) | | | | | Mean Ratio Confidence Interval | |
|---|---|---|---|---|---|---|---|---|---|---|---|---|---|
| | | | | | Substrate | Interacting Drug | $C_{max}$ ng/mL | $T_{max}$ h | $AUC_{tot}$ ng·h/mL | $AUC_\tau$ ng·h/mL | $T_{1/2}$ h | $C_{max}$ ng/mL | $AUC_{total}$ ng·h/mL |
| Mifepristone 300 mg Tablet | Effect of ketoconazole 400 mg OD (or 200 mg BID) on PK of 300 mg single Mifepristone given fasted | Phase 1, open-label, parallel group, single MIFE dose, multiple keto doses, in healthy subjects | 12/12 (12 M) | 28 20-44 | MIFE 300 mg C1 | 400 mg/d Keto 400 mg OD | 3398 (6.77) | median 2.00 | 116939 (26850) | 38111 (8768) | 37.1 (9.77) | 1.15 0.81-1.63 (C2/C1) | 1.05 0.72-1.54 (C2/C1) |
| Keto 200 mg Tablet | | | | | MIFE 300 mg C2 | 400 mg/d Keto 200 mg BID | 4143 (1736) | median 1.00 | 130925 (60942) | 40625 (16524) | 37.4 (18.5) | | |

MIFE = mifepristone,

Keto = ketoconazole, $AUC_{tot}$ = $AUC_{total}$, $AUC_\tau$ = $AUC_{0-24}$ hours following single dose of MIFE C1 = Cohort 1, C2 = Cohort 2

TABLE 2

| Product ID/Batch # (NME) | Study Objective | Study Design | # Subjects Enter/Complete (M/F) | Age: Mean Range | Treatments Substrate | Treatments Interacting Drug | MIFEPRISTONE Mean PK Parameters (SD) $C_{max}$ ng/mL | $T_{max}$ h | $AUC_{tot}$ ng·h/mL | $AUC_t$ ng·h/mL | $T_{1/2}$ h | Mean Ratio Confidence Interval $C_{max}$ ng/ml | Mean Ratio Confidence Interval $AUC_\tau$ ng·h/mL |
|---|---|---|---|---|---|---|---|---|---|---|---|---|---|
| Mifepristone 300 mg Tablet Keto 200 mg Tablet | Effect of 400 mg single dose of ketoconazole on PK an 8 day regimen of 300 mg OD Mifepristone (or 600 mg OD Mifepristone) given with moderate fat (34%) breakfast | Phase 1, open-label, parallel group, crossover within group with multiple MIFE doses, and single keto dose, in healthy subjects | 12/10 (12 M) | 29.8 20-43 | MIFE 300 mg/d C1 Day 7 | | 2700 (534) | median 3.0 | $NC^a$ | 37734 (11905) | | 1.19 0.93-1.53 C1 Day 8/ Day 7 | 1.25 0.88-1.76 C1 Day 8/ Day 7 |
| | | | | | MIFE 300 mg/d C1 Day 8 | 400 mg Keto single dose | 3240 (760) | median 2.1 | $NC^a$ | 47357 (17239) | 84.9 (46.6) | | |
| | | | | | MIFE 600 mg/d C2 Day 7 | | 3818 (703) | median 4.0 | $NC^a$ | 54174 (7305) | | 1.39 1.13-1.70 C2 Day 8/ Day 7 | 1.28 1.09-1.49 C2 Day 8/ Day 7 |
| | | | | | MIFE 600 mg/d C2 Day 8 | 400 mg Keto single dose | 5264 (795) | median 4.0 | $NC^a$ | 69112 (9077) | 96.2 (45.4) | 1.42 1.13-1.78 Day 7 C2/C1 1.65 1.30-2.08 Day 8 C2/C1 | 1.48 1.13-1.94 Day 7 C2/C1 1.52 1.14-2.02 Day 8 C2/C1 |

MIFE = mifepristone,
Keto = ketoconazole
C1 = Cohort 1,
C2 = Cohort 2
$AUC_\tau = AUC_{0-24}$ hours following Day 7 or Day 8 dose of MIFE
$^a AUC_{tot} = AUC_{total}$, not computed (NC) for multiple dosing

TABLE 3

Effects of Co-Administration with Ketoconazole on Mifepristone and Metabolites Test: Day 17 - 600 mg mifepristone OD + 200 mg Ketoconazole BID Reference: Day 12 - 600 mg mifepristone OD

| Analyte | Parameter | N | Ratio % Test/Reference | Lower 90% CI | Upper 90% CI |
|---|---|---|---|---|---|
| Mifepristone | $C_{max}$ | 13 | 127.59 | 116.66 | 139.54 |
| | $AUC_{0-24}$ | 13 | 138.01 | 127.12 | 149.84 |
| RU 42633 | $C_{max}$ | 13 | 105.73 | 95.92 | 116.54 |
| | $AUC_{0-24}$ | 13 | 102.33 | 94.31 | 111.03 |
| RU 42698 | $C_{max}$ | 13 | 169.13 | 156.36 | 182.94 |
| | $AUC_{0-24}$ | 13 | 166.86 | 155.06 | 179.57 |
| RU 42848 | $C_{max}$ | 13 | 95.48 | 90.82 | 100.38 |
| | $AUC_{0-24}$ | 13 | 94.88 | 91.33 | 98.56 |

TABLE 4

Effects of Co-Administration with Mifepristone on Ketoconazole Test: Day 17 - 600 mg mifepristone OD + 200 mg Ketoconazole BID Reference: Day -1 - 200 mg Ketoconazole Single Dose

| Parameter | N | Ratio % Test/Reference | Lower 90% CI | Upper 90% CI |
|---|---|---|---|---|
| $C_{max}$ | 14 | 252.71 | 214.85 | 297.26 |
| AUC | 14 | 365.36 | 333.78 | 399.93 |

TABLE 5

Cross-study Comparison of Exposure to Mifepristone and Metabolites
Test: Present Study Day 17 - 600 mg mifepristone OD + 200 mg Ketoconazole BID
Reference: Historic Study Day 7 - 1200 mg mifepristone OD alone

| Analyte | Parameter | Ratio % Test/Ref | Lower 90% CI | Upper 90% CI |
|---|---|---|---|---|
| Mifepristone | $C_{max}$ | 84.64 | 72.92 | 98.23 |
|  | $AUC_{0-24}$ | 87.27 | 74.72 | 101.94 |
| RU 42633 | $C_{max}$ | 96.31 | 80.83 | 114.75 |
|  | $AUC_{0-24}$ | 91.34 | 76.95 | 108.43 |
| RU 42698 | $C_{max}$ | 116.55 | 97.47 | 139.38 |
|  | $AUC_{0-24}$ | 118.18 | 97.90 | 142.66 |
| RU 42848 | $C_{max}$ | 82.45 | 70.31 | 96.70 |
|  | $AUC_{0-24}$ | 81.43 | 69.71 | 95.11 |

All doses given within 30 minutes after typical (34%) fat meal

TABLE 6

MIFEPRISTONE with and without ITRACONAZOLE
Study Drug Dosing and PF Sampling Schedule

| | Period 1— Mifepristone 1200 mg QD | | Period 2— Mifepristone 900 mg QD | | Period 3— Mifepristone 900 mg QD Plus ITZ 200 mg QD | | Follow-Up to End of Study | |
|---|---|---|---|---|---|---|---|---|
| Day | Out-patient 1[a]-12 | Con-fined 13-14[b] | Out-patient 15[a]-26 | Con-fined 27-28[c] | Out-patient 29-41 | Con-fined 42 | Con-fined 43 | Outpatient/ Termination 44-55/56 ± 1 |
| | | | Study Treatment | | | | | |
| ITZ | | | | | X | X | | |
| MIFE | X | X | X | X | X | X | | |
| | | | PK Sampling | | | | | |
| MIFE | PK trough D 1, 2, 4, 6, 8, 11, 12 | PK trough D 13 PK profile 24-h[d] D 14 | PK trough D 15, 16, 18, 20, 22, 25, 26 | PK trough D 27 PK profile 24-h[e] D 28 | PK trough D 29, 30, 32, 34, 36, 39, 40, 41 | PK trough | PK trough 24-h[f] | |
| ITZ | | | | | PK trough D 29, 30, 32, 34, 36, 39, 40, 41 | PK trough | PK trough | |

ITZ = itraconazole,
MIFE = mifepristone.
Note:
dosing windows on Days 13 and 14, 27, and 28, and 41 and 42 are ±30 min; on other days, dosing windows are ±2 h.
[a] Outpatient status on Days 1 and 15 begin after PK sampling is complete.
[b] For the 24-h PK profile on Day 14, subjects are admitted on the morning of Day 13 and are discharged the morning of Day 15.
[c] For 24-h PK profile on Day 28, subjects are admitted on the morning of Day 27 and will remain in confinement through the morning of Day 43.
[d] 24-h sample is taken predose on Day 15.
[e] 24-h sample is taken predose on Day 29.
[f] 24-h sample is taken predose on Day 43.

TABLE 7

MIFEPRISTONE and its METABOLITES: EXPOSURE DATA
900 mg Mifepristone + 200 mg Itraconazole compared to 1200 mg Mifepristone

| | | Geometric Means | | Geometric Mean Ratio (%) (ratio of analyte with/without Itraconazole coadministration) | |
|---|---|---|---|---|---|
| | | 900 mg Mife + 200 mg Itraconazole | 1200 mg Mifepristone | Ratio (%) | 90% Confidence Interval (%) |
| Mifepristone | Cmax | 4,260 | 4,360 | 97.69 | 87.43-109.16 |
|  | AUC(0-24) | 65,400 | 67,700 | 96.62 | 89.33-104.52 |

TABLE 7-continued

MIFEPRISTONE and its METABOLITES: EXPOSURE DATA
900 mg Mifepristone + 200 mg Itraconazole compared to 1200 mg Mifepristone

|  |  | Geometric Means | | Geometric Mean Ratio (%) (ratio of analyte with/without Itraconazole coadministration) | |
|---|---|---|---|---|---|
|  |  | 900 mg Mife + 200 mg Itraconazole | 1200 mg Mifepristone | Ratio (%) | 90% Confidence Interval (%) |
| RU-42633 | Cmax | 1,970 | 2,160 | 90.95 | 84.56-97.83 |
|  | AUC(0-24) | 41,900 | 45,800 | 91.58 | 85.48-98.12 |
| RU-42698 | Cmax | 897 | 853 | 105.16 | 96.49-114.61 |
|  | AUC(0-24) | 18,600 | 16,900 | 110.14 | 103.31-117.42 |
| RU-42848 | Cmax | 1,520 | 1,770 | 86 | 79.61-92.91 |
|  | AUC(0-24) | 32,800 | 36,500 | 89.82 | 84.26-95.74 |

TABLE 8

MIFEPRISTONE and its METABOLITES: EXPOSURE DATA
900 mg Mifepristone + 200 mg Itraconazole compared to 900 mg Mifepristone

|  |  | Geometric Means | | Geometric Mean Ratio (%) (ratio of analyte with/without Itraconazole coadministration) | |
|---|---|---|---|---|---|
|  |  | 900 mg Mife + 200 mg Itraconazole | 900 mg Mifepristone | Ratio (%) | 90% Confidence Interval (%) |
| Mifepristone | Cmax | 4,260 | 3550 | 120.17 | 107.55-134.28 |
|  | AUC(0-24) | 65,400 | 59600 | 109.72 | 101.43-118.68 |
| RU-42633 | Cmax | 1,970 | 1970 | 99.89 | 92.87-107.45 |
|  | AUC(0-24) | 41,900 | 40,300 | 104.00 | 97.07-111.43 |
| RU-42698 | Cmax | 897 | 755 | 118.83 | 109.03-129.51 |
|  | AUC(0-24) | 18,600 | 15,100 | 123.09 | 115.46-131.24 |
| RU-42848 | Cmax | 1,520 | 1,630 | 93.61 | 86.66-102.13 |
|  | AUC(0-24) | 32,800 | 33,900 | 96.68 | 90.70-103.06 |

What is claimed is:

1. A method of controlling hyperglycemia secondary to hypercortisolism in a patient with endogenous Cushing's syndrome, said patient taking an original once-daily dose of 1200 milligrams (mg) per day of mifepristone, the method comprising the steps of:
reducing said original once-daily dose to an adjusted once-daily dose of 900 mg per day of mifepristone, and
administering the adjusted once-daily dose of 900 mg per day of mifepristone to the patient when the patient is receiving concomitant administration of a strong CYP3A inhibitor,
wherein said strong CYP3A inhibitor is selected from the group consisting of ketoconazole, itraconazole, nefazodone, ritonavir, nelfinavir, indinavir, boceprevir, clarithromycin, conivaptan, lopinavir, posaconazole, saquinavir, telaprevir, cobicistat, troleandomycin, tipranivir, paritaprevir, and voriconazole.

2. The method of claim 1, wherein said strong CYP3A inhibitor is selected from the group consisting of nefazodone, ritonavir, nelfinavir, boceprevir, clarithromycin, conivaptan, lopinavir, saquinavir, telaprevir, cobicistat, troleandomycin, tipranavir, and paritaprevir.

3. The method of claim 1, wherein said strong CYP3A inhibitor is ketoconazole.

4. The method of claim 1 wherein said strong CYP3A inhibitor is itraconazole.

5. The method of claim 1, wherein said strong CYP3A inhibitor is clarithromycin.

6. A method of controlling hyperglycemia secondary to hypercortisolism in a patient with endogenous Cushing's syndrome, said patient taking an original once-daily dose of 900 milligrams (mg) per day of mifepristone, the method comprising the steps of:
reducing said original once-daily dose to an adjusted once-daily dose of 600 mg per day of mifepristone, and
administering the adjusted once-daily dose of 600 mg per day of mifepristone to the patient when the patient is receiving concomitant administration of a strong CYP3A inhibitor,
wherein said strong CYP3A inhibitor is selected from the group consisting of ketoconazole, itraconazole, nefazodone, ritonavir, nelfinavir, indinavir, boceprevir, clarithromycin, conivaptan, lopinavir, posaconazole, saquinavir, telaprevir, cobicistat, troleandomycin, tipranivir, paritaprevir, and voriconazole.

7. The method of claim 6, wherein said strong CYP3A inhibitor is selected from the group consisting of nefazodone, ritonavir, nelfinavir, boceprevir, clarithromycin, conivaptan, lopinavir, saquinavir, telaprevir, cobicistat, troleandomycin, tipranavir, and paritaprevir.

8. The method of claim 6, wherein said strong CYP3A inhibitor is ketoconazole.

9. The method of claim 6, wherein said strong CYP3A inhibitor is itraconazole.

10. The method of claim 6, wherein said strong CYP3A inhibitor is clarithromycin.

11. A method of controlling hyperglycemia secondary to hypercortisolism in a patient with endogenous Cushing's syndrome, said patient taking an original once-daily dose of 1200 milligrams (mg) per day of mifepristone, the method comprising the steps of:
reducing said original once-daily dose to an adjusted once-daily dose of 600 mg per day of mifepristone, and
administering the adjusted once-daily dose of 600 mg per day of mifepristone to the patient when the patient is receiving concomitant administration of a strong CYP3A inhibitor,
wherein said strong CYP3A inhibitor is selected from the group consisting of ketoconazole, itraconazole, nefazodone, ritonavir, nelfinavir, indinavir, boceprevir, clarithromycin, conivaptan, lopinavir, posaconazole, saquinavir, telaprevir, cobicistat, troleandomycin, tipranivir, paritaprevir, and voriconazole.

12. The method of claim 11, wherein said strong CYP3A inhibitor is selected from the group consisting of nefazodone, ritonavir, nelfinavir, boceprevir, clarithromycin, conivaptan, lopinavir, saquinavir, telaprevir, cobicistat, troleandomycin, tipranavir, and paritaprevir.

13. The method of claim 11, wherein said strong CYP3A inhibitor is ketoconazole.

14. The method of claim 11, wherein said strong CYP3A inhibitor is itraconazole.

15. The method of claim 11, wherein said strong CYP3A inhibitor is clarithromycin.

16. The method of claim 6, further comprising, at least one week after the first once-daily administration of said adjusted once-daily dose of 600 mg per day of mifepristone,
upwardly titrating said adjusted once-daily dose of 600 mg per day of mifepristone to an upwardly titrated once-daily dose of 900 mg per day of mifepristone, and
administering the upwardly titrated once-daily dose of 900 mg per day of mifepristone to the patient when the patient is receiving concomitant administration of a strong CYP3A inhibitor.

17. The method of claim 1, wherein said mifepristone administration comprises oral administration of mifepristone.

18. The method of claim 6, wherein said mifepristone administration comprises oral administration of mifepristone.

19. The method of claim 11, wherein said mifepristone administration oral administration of mifepristone.

20. The method of claim 16, wherein said mifepristone administration oral administration of mifepristone.

* * * * *